United States Patent
Miyamoto et al.

(10) Patent No.: US 6,197,574 B1
(45) Date of Patent: Mar. 6, 2001

(54) BACTERIUM DETECTOR

(75) Inventors: Toshihiko Miyamoto; Youji Ikeno; Nobuo Shimoshiro, all of Hachioji; Atsushi Takamatsu, Tachikawa; Kazunori Hochito, Hachioji; Yoshihiko Abe, Hachioji; Jun-ichi Satake, Hachioji, all of (JP)

(73) Assignee: SRL, Inc., Tokyo (JP)

( * ) Notice: Subject to any disclaimer, the term of this patent is extended or adjusted under 35 U.S.C. 154(b) by 0 days.

(21) Appl. No.: 09/101,269

(22) PCT Filed: Nov. 9, 1997

(86) PCT No.: PCT/JP97/04066

§ 371 Date: Jan. 25, 1999

§ 102(e) Date: Jan. 25, 1999

(87) PCT Pub. No.: WO98/20107

PCT Pub. Date: May 14, 1998

(30) Foreign Application Priority Data

Nov. 7, 1996 (JP) .................................... 8-309889
Feb. 20, 1997 (JP) .................................... 9-051119
May 30, 1997 (JP) .................................... 9-156094

(51) Int. Cl.$^7$ .............................. C12M 1/30; C12Q 1/24
(52) U.S. Cl. .................................... 435/287.6; 435/288.2; 435/309.1; 435/30; 435/31; 435/32
(58) Field of Search .................................... 435/32, 34, 39, 435/30, 287.4, 287.6, 287.7, 288.1, 288.2, 304.1, 309.1, 810

(56) References Cited

U.S. PATENT DOCUMENTS 3,910,410 * 10/1975 Shaw .
4,717,661 1/1988 McCormick et al. .
4,743,537 5/1988 McCormick et al. .

FOREIGN PATENT DOCUMENTS 0 223 745   5/1987   (EP) .
62-171671   7/1987   (JP) .
62-228147  10/1987   (JP) .
7-308184   11/1995   (JP) .

* cited by examiner

*Primary Examiner*—William H. Beisner
(74) *Attorney, Agent, or Firm*—Wenderoth, Lind & Ponack, L.L.P.

(57) ABSTRACT

An object of the present invention is to offer a microorganism-detecting apparatus where the microorganism causing a food poisoning can be detected/identified by a simple operation and also a disposal treatment can be conducted safely and surely. An apparatus for achieving the object is as follows: The apparatus for detecting microorganism as mentioned below is portable and enables one to selectively incubate and detect the microorganism (particularly those which are a cause of food poisoning) without skillfulness and the detecting apparatus containing pathogenic microorganism (such as that which is a cause of food poisoning) can be safely and surely disposed. The apparatus is characterized in having at least (a) a container (1) for holding a medium which is used for culturing the microorganism to be detected during the period of the incubation of said microorganism; (b) a microorganism-collecting part (6); (c) a structure (3) for making possible a process of receiving, in a noncontact manner with the microorganism-collecting part, the medium used for culturing the microorganism to be detected until the incubating stage of the microorganism; and (d) a structure (9) for disinfecting the medium after incubation.

49 Claims, 61 Drawing Sheets

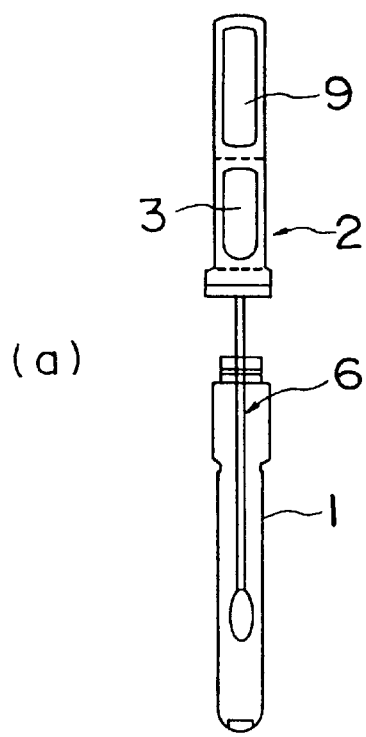
FIG. 2
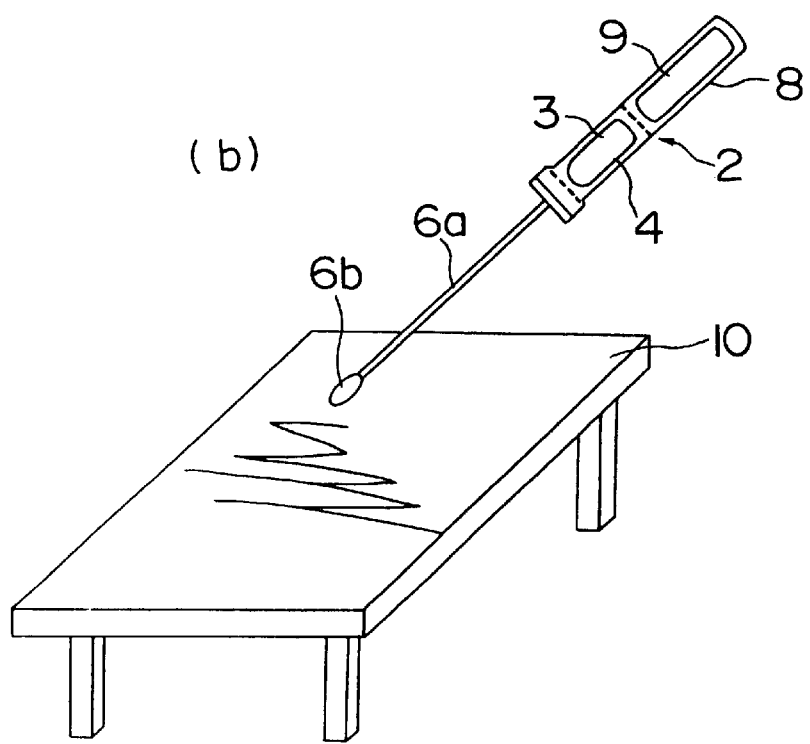

BACTERIUM DETECTOR

TECHNICAL FIELD

The present invention relates to an apparatus for selectively detecting microorganisms whereby pathogenic microorganisms, particularly food poisoning microorganisms and drug-resitant microorganisms such as methicillin-resistant *Staphylococcus aureus* (MRSA) can be easily and simply detected and/or identified. More particularly it relates to an apparatus for a selective detection of microorganisms which is particularly suitable even for private and domestic use where its storage for a long time can be expected, which can be immediately used at any time when needed, which has a portable form such that it can be conveniently and easily carried, which is capable of safely detecting and identifying a food poisoning microorganism or the like by performing a simple operation, and which can be disposed of safely, surely and easily after its use.

BACKGROUND ART

Pathogenic microorganisms which are present in the living environment have been considerably overcome due to a high development in medical service and progress in therapy in recent years, particularly inventions and developments in antibacterial and antibiotics and, moreover, due to an improvement in hygiene. However, once they break out, big damage and fatal problems may result, and thus pathogenic microorganisms remain causes of big problems.

Examples of the pathogenic microorganisms which cause troubles when present around us are those causing food poisoning and those resistant to antibiotics, such as methicillin-resistant *Staphylococcus aureus* (MRSA) and the like. Thus, there are problems such as the occurrence of a lot of patients infected by these microorganisms, and hospital infection as well.

Taking food and beverage or the "eating" action is essential for animals including human beings and, therefore, in spite of progress in science and high development in technique in recent years, it is still difficult to completely prevent "food poisoning" caused by taking food and beverage. On the other hand, prevention of food poisoning as such has been more and more important because of the Product Liability Law which has been inaugurated recently.

Food poisoning is roughly classified into three types depending upon its cause, i.e. that by natural poison (toxin) (such as swellfish poison (Tetraodontidae toxin) and mushroom poison), that by putrefaction of food and beverage (such as by decomposed products of food and beverage), and that by contamination by or proliferation of bacteria (such as Staphylococcus, Salmonella and *Vibrio parahaemolyticus*) in food and beverage. Among them, food poisoning by natural poison can be easily avoided by preventing the intake of food/beverage containing the causing poison. In addition, detection of putrefaction of food/beverage by means of checking the changes in appearance, smell, etc. is usually easy. Therefore, prevention of food poisoning due to putrefaction of food/beverage is relatively easy in many cases.

In contrast to those two types of food poisoning, contamination by or proliferation of the microorganisms is usually invisible in the case of food poisoning by bacteria (that is, the bacterial food poisoning) and, moreover, detection of this contamination or proliferation is very difficult without participation of professional people. Accordingly, the bacterial food poisoning is a food poisoning which is most difficult to avoid.

Occurrence of food poisoning associated restaurants, caterers for luncheon and feeding facilities affects are significantly many people and, in addition, the symptoms is serious such as severe vomiting, diarrhea, abdominal pain, high fever, etc., whereby it is apt to result in a particularly serious problem such as stoppage of business of the food provider for a long term. A further problem is that, since the microorganism causing such food poisoning produces toxic substances such as enterotoxin in the body of infected patients, it is necessary to conduct a therapy after infection and, moreover, this therapy is very often accompanied by a difficulty.

Accordingly, it is quite necessary that the microorganism which is a cause of such a symptom is found at an early stage and that a preventive measure such as disinfection is conducted for preventing the poisoning.

As a result of the use of antibacterials and antibiotics, occurrence of diseases, especially infectious diseases such as contagious disease, has significantly decreased. On the other hand, however, many resistant microorganisms have appeared as a secondary phenomenon resulting in a big problem. There is a problem that, when a powerful antibiotic substance is developed, resistance thereto occurs immediately and, in addition, hospital infection by such resistant microorganisms have become a big problem too. Since patients including those suffering from severe disease and aged people has an decreased resistance, microorganisms which are resistant to antibiotics cause a intractable infectious disease whereby, even when the infection is found, there will be no effective therapy and that is a big problem. For preventing the hospital infection caused by such resistant microorganisms, it is necessary to specify the causing microorganism in an early stage of infection, to find its presence at an early date and to effectively and appropriately prevent the infection by means of disinfection, etc. Accordingly, it is necessary for hospitals to periodically check whether such microorganisms appear in the medical environment.

Up to now, there has been no method other than common preventing measures (such as keeping the cooking utensils, e.g. kitchen knife and chopping board, clean and also keeping hand and fingers of the persons participating in cooking clean) for preventing the food poisoning. Even at present, when food poisoning occurs, only an ex posto facto measure (i.e. the causing microorganism is detected and confirmed by a search (by incubation of the suspected microorganism found in the food/beverage) of the public health center controlling the place where the poisoning occurred) is available. In addition, detection and confirmation of the causing microorganism by the center as such usually require quite a long period (e.g., around one to two weeks). Further, the search by the public health center needs a "prescribed procedure" and, moreover, in view of honor or reputation (such as an entire loss of customers by "rumor"), such a procedure is not always fully activated. Additionally, it is not always possible to detect and confirm the causing microorganism so simply.

In the investigation at the professional organizations such as public health centers and hospitals, a method which has been adopted is that various samples as mentioned above and those collected from patients and from a medical environment are incubated on agar plates using a selective medium, and the colonies formed on the medium are observed by the naked eye, or the microorganism incubated as such is confirmed by other detecting and confirming measures. Recently, a judging method using polymerase chain reaction (PCR) has been adopted as well. However, the operations are troublesome in all of such conventional methods and, in judging the colonies grown on the agar medium, professional technique and skillfulness are needed for identification. In addition, professional technique and skillfulness as well as specific devices or the like are required for the operations from collection of the sample to its incubation and there is a disadvantage that total cost for the detection is high. Further, in the case of a method utilizing a PCR, it is again necessary to apply professional technique and skillfulness and there is another problem that, for certain microorganisms, discrimination of them from nonpathogenic ones is very difficult.

For a device for solving these problems, an apparatus accommodating a liquid medium enclosed in a capsule and a tampon for collecting microorganisms in a capsule-container is proposed, for example, in Unexamined Japanese Patent Publication Sho 62-171671 (JP Sho 62-171671 A). Because such an apparatus contains pathogenic microorganisms after incubation, however, it is difficult to discard it. Therefore, in the prior art the used apparatus has been discarded after disinfecting steps, including opening the used container followed by addition of a disinfectant solution to the medium containing the microorganisms.

Because the apparatus has been brought into an open system, for example, by taking off a stopper, etc., in oder to discard the incubation system containing the pathogenic microorganisms, such a treatment is not only troublesome and risky but also requires professional technique and great skill, even installations. Furthermore, since, in addition to the container for incubation, it is always necessary to prepare a disinfectant solution for the treatment, it is troublesome in view of portability and convenience in use.

SUMMARY OF THE INVENTION

An object of the present invention is to provide an apparatus (or device) for detecting microorganisms whereby pathogenic microorganisms such as those causing food poisoning and resistant microorganisms can be detected and identified by simple operations and, after use, the apparatus can be safely and conveniently disposed.

Another object of the present invention is to provide an apparatus for detecting microorganisms which can be not only used in hospitals but also used privately or at home and which can be disposed by anyone easily and safely.

Still another object of the present invention is to provide an apparatus for detecting microorganisms where its handling is simple whereby it can be used at any time, previous or spontaneous countermeasure to pathogenic microorganisms can be made very easy and disposal of the apparatus after use can be made easily and safely.

The present inventors have conducted an intensive study and found that the following constitution is very effective in achieving the above-mentioned objects. A characteristic feature of a relatively convenient microorganism-detecting apparatus (wherein a medium which is to give an incubating condition suitable for the pathogenic microorganisms to be detected (such as specific microorganisms for food poisoning and microorganisms which are resistant to specific antibiotics) upon contacting the microorganisms, and a microorganism-collecting part are located in a noncontact manner relative to each other and, when incubation for detecting the microorganism is conducted, the specific medium and microorganism-collecting part are contacted with each other) is more fully utilized and, in addition, disposal (in some cases, disinfecting treatment) of the apparatus after use can be conducted safely and easily.

The apparatus for the detection of microorganisms in accordance with the present invention is based upon the above finding.

In one of its aspects, the present invention provides:

(1) an apparatus for detecting a microorganism, characterized in that, the apparatus comprises at least:
   (a) a container for holding a medium which is used for culturing the microorganism to be detected during the period of the incubation of the microorganism,
   (b) a part where the microorganism is collected,
   (c) structure for allowing a person to hold the medium for culturing the microorganism to be detected, in a noncontact manner with the microorganism-collecting part (b), until the incubating stage of the microorganism, and
   (d) structure for disinfecting the medium after incubation;

(2) the apparatus for detecting the microorganism according to the above (1) wherein the structure (d) (structure for disinfecting the medium after incubation) includes structure for allowing a disinfectant to be held, without contact with the microorganism, until the completion of the incubation for the microorganism to be detected;

(3) the apparatus for detecting the microorganism according to the above (1) or (2) wherein the medium and the disinfectant are made in such a manner that they can unitedly contact each other, by the action of a force applied from outside, after incubation of the microorganism;

(4) the apparatus for detecting the microorganism according to any of the above (1) to (3) wherein the microorganism-collecting part (b) and the medium used for culturing the microorganism to be detected are made in such a manner that they can unitedly contact each other, by the action of a force applied from outside, during the incubation of the microorganism;

(5) the apparatus for detecting the microorganism according to any of the above (1) to (4) wherein the apparatus contains;
   (a) a hollow container having an opening at one of its ends,
   (b) a microorganism-collecting part located in the hollow container,
   (c) a medium for culturing the microorganism, the medium being located so as to contact the microorganism-collecting part during the incubation of the microorganism, and
   (d) a disinfectant being located so as to contact the medium for culturing the microorganism after the incubation of the microorganism;

(6) the apparatus for detecting the microorganism according to any of the above (1) to (5) wherein the antibiotic substance is added to the medium;

(7) the apparatus for detecting the microorganism according to any of the above (1) to (6) wherein an antibiotic substance is contained, at least part of the antibiotic substance coming unitedly into contact with the medium, by the action of an external force, during the incubation of the microorganism, and at least the antibiotic substance and the medium being located in the holding container in a noncontact manner;

(8) the apparatus for detecting the microorganism according to any of the above (1) to (7) wherein the microorganism is detected through incubating the microorganism in a medium and observing the changes in the medium, characterized in that the apparatus comprises
   (i) a microorganism-collecting part,
   (ii) an antibiotic substance, (iii) a medium and (iv) a disinfectant, wherein at least a part of (i) the microorganism-collecting part, (ii) the antibiotic substance and (iii) the medium can unitedly contact each other, by the action of a force from outside, during the incubation of the microorganism, at least the above-mentioned antibiotic substance (ii) and the above-mentioned medium (iii) being located in a storage container in a noncontact manner, and wherein, after incubation of the microorganism, at least the incubated microorganism and the disinfectant (iv) can unitedly contact each other by the action of a force from outside, at least the above-mentioned disinfectant (iv) and the above-mentioned medium (iii) being located in the storage container in a noncontact manner;

(9) the apparatus for detecting the microorganism according to any of the above (1) to (5) and (7) to (8) wherein the antibiotic substance is (1) located in the above-mentioned container, (2) given to the above mentioned microorganism-collecting part or (3) coated on the inner wall of the above-mentioned container;

(10) the apparatus for detecting microorganism according to any of the above (1) to (5) and (7) to (9) wherein the antibiotic substance is given to other materials located in the hollow container;

(11) the apparatus for detecting the microorganism according to any of the above (1) to (5) and (7) to (9) wherein the microorganism-collecting part has a multiple structure containing at least an inside material and an outside material and the antibiotic substance is located in the inside material;

(12) the apparatus for detecting the microorganism according to any of the above (1) to (11) wherein the medium contains a substance capable of changing its color according to the change caused by growth of the microorganism;

(13) the apparatus for detecting the microorganism according to any of the above (1) to (12) wherein the container has a cover for tight closing of the container and the medium is located in the cover in such a manner that it is enclosed in a bag-shaped member or vessel;

(14) the apparatus for detecting the microorganism according to the above (13) wherein a perforated member is located between the bag-shaped member and the hollow container;

(15) the apparatus for detecting the microorganism according to the above (14) wherein a guide member which can promote a fall of the medium descending along the microorganism-collecting part is located under the perforated member;

(16) the apparatus for detecting the microorganism according to any of the above (1) to (15) wherein the apparatus has a incubation selectivity for at least one microorganism selected from the group consisting of pathogenic *Escherichia coli, Staphylococcus aureus, Vibrio parahaemolyticus* and Salmonella;

(17) the apparatus for detecting the microorganism according to any of the above (1) to (16) wherein the apparatus has a structure for allowing a person to disinfect the medium used for the incubation under a tightly closed state; and

(18) the apparatus for detecting the microorganism according to any of the above (1) to (17) wherein the apparatus has a structure for allowing a person to conduct at least (i) addition of a medium into a container, (ii) incubation, (iii) visual detection of the microorganism cells, and (iv) disinfecting treatment of the incubated medium under a tightly closed state after collecting of the microorganism by the microorgansim-collecting part.

The present invention further contemplates:

(19) an apparatus for detecting a microorganism, characterized in that, the apparatus consists of (i) a container having a space wherein a medium is received and the microorganism is cultured and (ii) a cover which engages with an opening of the container to tightly close (fasten or seal) the opening of the container from the surrounding atmosphere (outside), the cover being a receptacle body having (A) a first bag-shaped member or vessel for holding (enclosing) the medium and (B) a second bag-shaped member or vessel for holding (enclosing) a disinfectant;

(a) the receptacle body being bestowed with a function for breaking the inner bag-shaped member by the action of a force applied from outside in order to remove the contents from the first bag-shaped member, (b) the second bag-shaped member capable of being broken independently of the first bag-shaped member whereby the contents in the second bag-shaped member are removed therefrom;

(c) at or near a connecting portion of the cover engaged with the opening of the container, a partition being formed or a partition member being disposed for keeping the bag-shaped members in the cover;

(d) the partition or the partition member being equipped with a microogranism-collecting part which is positioned in a protruding manner at the side of a space of the container for receiving the medium and culturing the microorganism therein;

(e) wherein the end of the microorganism-collecting part can contact the medium in such manner that it is possible to culture the microorganism when the container receives the medium; and (f) wherein one or more through holes are formed in the partition or the partition member so that the medium and the disinfectant can flow between the cover and the container;

(20) the apparatus for detecting the microorganism according to the above (19), characterized in that, each of the first and the second bag-shaped members is a glass ampule, the cover is made of a flexible material and, even when a force from outside (an external force) is applied to the cover for breaking the first bag-shaped member to remove the medium which is a content therein, the second bag-shaped member is not damaged and the disinfectant which is a content therein can be kept as stored;

(21) the apparatus for detecting the microorganism according to the above (19), characterized in that, the cover is composed of a first section for receiving the first bag-shaped member and a second section for receiving the second bag-shaped member, the first section being installed with a first pushing-down member for breaking the first bag-shaped member and the second section being installed with a second pushing-down member for breaking the second bag-shaped member.

(22) the apparatus for detecting the microorganism having a structure as shown in any of FIGS. 6 to 11 or characterized in having substantially the same function concerning the bactericidal treatment of the incubated microorganism culture;

(23) An apparatus for detecting the microorganism according to the above (19), characterized in that
the cover is composed of:
(a) a first cover-constituting member which constitutes a first section for receiving the first bag-shaped member,
(b) a second cover-constituting member which constitutes a second section for receiving the second bag-shaped member, and
(c) a cap member being located at one end of the second cover-constituting member and at the opposite side of the fitting side (of the second cover-constituting member) for the first cover-constituting member and slidably fitted into the second cover-constituting member,
wherein, at or near each end of the first and second cover-constituting members, each end being at the side of the container having a space for receiving the medium to culture the microorganism therein, a partition is formed or a member for the partition is disposed for preventing each of the bag-shaped members from entering the container;
the first cover-constituting member being slidably engaged with one end of the second cover-constituting member wherein the first bag-shaped member can be broken to release the medium contained therein by sliding the second cover-constituting member to the side of the first cover-continuing member by a force from outside (external force),
wherein the second bag-shaped member can be broken to release a disinfectant contained therein by sliding the cap member to the side of the second cover-constituting member by a force from outside (external force), and
wherein one or more through holes are formed in the partition or the partition member in a manner that the medium and the disinfectant can be communicated with the container;

(24) the apparatus for detecting the microorganism according to the above (23), characterized in that,
an engagement of the first cover-constituting member with one end of the second cover-constituting member is achieved by use of a screw thread and a force is generated by rotating the second cover-constituting member against the first cover-constituting member by a force from outside (external force) whereby the first bag-shaped member can be broken to release the medium which is a content therein;

(25) the apparatus for detecting the microorganism according to the above (23), characterized in that,
an engagement of the second cover-constituting member with the cap member is achieved by use of a screw thread and an external force is generated by rotating the cap member against the second cover-constituting member whereby the second bag-shaped member can be broken to release the disinfectant which is a content therein;

(26) the apparatus for detecting the microorganism according to the above (24), characterized in that,
the first and second cover-constituting members are constituted from a cylindrical body;

(27) the apparatus for detecting the microorganism having an arrangement as shown in FIG. 12 or FIG. 13 or characterized in having substantially the same function concerning the bactericidal treatment of the cultured microorganism;

(28) the apparatus for detecting the microorganism according to the above (19), characterized in that,
the cover is composed of:
(a) a first cover-constituting member which has a first section housing a first bag-shaped member and a second section receiving a second cover-constituting member housing a second bag-shaped member,
(b) the second cover-constituting member and
(c) a cap member which is slidably engaged with one end of the second cover-constituting member and is located thereon at the opposite side of the container having a space for receiving the medium to culture the microorganism therein;
wherein, at or near each end of the first and second cover-constituting members, each end being at the side of the container having a space for receiving the medium to culture the microorganism therein, a partition is formed or a member for the partition is disposed for preventing each of the bag-shaped members from entering the container;
the first cover-constituting member being slidably engaged with one end of the second cover-constituting member wherein the first bag-shaped member can be broken to release the medium contained therein by sliding the second cover-constituting member to the side of the first cover-constituting member by a force from outside (external force),
wherein the second bag-shaped member can be broken to release a disinfectant contained therein by sliding the cap member to the side of the second cover-constituting member by a force from outside (external force), and
wherein one or more through holes are formed in the partition or the partition member in a manner that the medium and the disinfectant can be communicated with the container;

(29) the apparatus for detecting the microorganism according to the above (28), characterized in that,
an engagement of the first cover-constituting member with a portion of the second cover-constituting member is achieved by use of a screw thread and a force is generated by rotating the second cover-constituting member against the first cover-constituting member by a force from outside (external force) whereby the first bag-shaped member can be broken to release the medium which is a content therein;

(30) the apparatus for detecting the microorganism according to the above (28), characterized in that,
an engagement of the second cover-constituting member with the cap member is achieved by use of a screw thread and an external force is generated by rotating the cap member against the second cover-constituting member whereby the second bag-shaped member can be broken to release the disinfectant which is a content therein;

(31) the apparatus for detecting the microorganism according to the above (28), characterized in that,
the first and second cover-constituting members are constituted from a cylindrical body;

(32) the apparatus for detecting the microorganism according to the above (28), characterized in that;
most of the second cover-constituting member is housed in the first cover-constituting member;

(33) the apparatus for detecting the microorganism as shown in FIG. 14 or characterized in having a function substantially equivalent thereto concerning the bactericidal treatment of the incubated microorganism;

(34) the apparatus for detecting the microorganism according to the above (19), characterized in that,
the cover is composed of:
(a) a receptacle body receiving both of a first bag-shaped member and a second bag-shaped member in a parallel and
(b) two tools for breaking the bag-shaped members, the tools being slidably engaged with the top of the receptacle body at the opposite side of the container having a space for receiving the medium to culture the microorganism,
wherein the tools are independently pushed into the receptacle body by sliding via a force from outside where, first, the first tool can break the first bag-shaped member to release the medium contained therein and then the second tool can break the second bag-shaped member to release the disinfectant contained therein, and
wherein through holes are made in the partition or the partition member so that the medium and the disinfectant can be communicated with the container;

(35) the apparatus for detecting the microorganism according to the above (34), characterized in that,
the tools are disposed in such a manner that they can be pushed into the top of the receptacle body via a force from outside;

(36) the apparatus for detecting the microorganism according to the above (34), characterized in that,
the tools are disposed in such a manner that they can be pushed into the top of the receptacle body in a screwing manner.

(37) the apparatus for detecting the microorganism according to the above (34), characterized in that,
the outer appearance of the receptacle body is of a structure similar to a rectangular parallelepiped.

(38) the apparatus for detecting the microorganism as shown in FIG. 15 or characterized in having a function substantially equivalent thereto concerning the bactericidal treatment of the incubated microorganism;

(39) the apparatus for detecting the microorganism according to the above (19), characterized in that
the cover consists of:
a receptacle body receiving a first bag-shaped member and a second bag-shaped member in parallel,
the receptacle body consisting of a holding member which constitutes a holding section capable of regulating the position of the bag-shaped members and a movable material which constitutes a movable section being rotatable by a force from outside against the holding section,
wherein a tool for breaking the bag-shaped member is installed on the inner side of the receptacle body,
wherein, when the movable member is rotated, any of the first bag-shaped member and said second bag-shaped member can be independently broken by the tool, and
wherein through holes are made in the partition or the partition member so that the medium and the disinfectant can be communicated with the container;

(40) the apparatus for detecting the microorganism according to the above (39), characterized in that,
a tool is installed on the inner side of the movable member in the receptacle body;

(41) the apparatus for detecting the microorganism according to the above (39), characterized in that,
the receptacle body is of a cylindrical shape and,
when the movable member of the receptacle body is rotated, any of the first bag-shaped member and the second bag-shaped member can be independently broken depending upon the direction of rotation; and

(42) the apparatus for detecting the microorganism as shown in FIG. 16 or characterized in having substantially the same function concerning the bactericidal treatment of the incubated microorganism.

The present invention further provides:
(43) an apparatus for detecting a microorganism, characterized in that the apparatus comprises:
(a) a hollow container in a cylindrical shape for holding a medium used for culturing the microorganism to be detected during the incubation of the microorganism,
(b) a microorganism-collecting part comprising a rod-like material and a microorganism-collecting end and
(c) a cover equipped with the microorganism-collecting part wherein the cover stores at least two bag-shaped members where the first bag-shaped member is to receive the medium while the second one is to receive a disinfectant (bactericide), and
wherein (d) the medium enclosed in the first bag-shaped member can contact the microorganism-collecting end without detaching the cover which closes the opening of the hollow container (a) and the disinfectant/bactericide enclosed in the second bag-shaped member can contact the microorganism in the hollow container to perform a disinfecting/bactericidal treatment;

(44) the apparatus for detecting the microorganism according to the above (43), characterized in that,
the cover is constituted from a material which can be easily deformed by a force from outside and the first and second bag-shaped members can be easily broken by a force from outside to discharge the liquid contents there of;

(45) the apparatus for detecting the microorganism according to the above (43), characterized in that,
the cover has a partition member at the side of the connecting part with the hollow container and the partition member has an action of receiving and holding the first and the second bag-shaped members in the cover;

(46) the apparatus for detecting the microorganism according to the above (43), characterized in that,
the partition member is capable of engaging with the cover at the side of the part (of the cover) connecting with the hollow container; and

(47) the apparatus for detecting the microorganism according to the above (43), characterized in that,
the cover is constituted in such a manner that each of the first and second bag-shaped members is independently broken by a force from outside so that the liquid contents thereof can be discharged.

The present invention further provides:
(48) the apparatus for detecting the microorganism according to the above (19), characterized in that,
the cover is composed of:
(a) a first cover-constituting member which constitutes a first section receiving and holding a first bag-shaped member,
(b) a second cover-constituting member which constitutes a second section receiving and holding a second bag-shaped member and (c) a cap member which is rotatably screw-fitted at one end of the second cover-constituting member, the cap member being located at the side thereof opposite to the connected side for the first cover-constituting member, wherein either a partition is formed or a member for the partition is disposed for keeping each of the bag-shaped members at or neat the end of the container, of the first and the second cover-constituting members, having a space for receiving the medium to culture the microorganism therein, wherein the first cover-constituting member is slidably fixed with one end of the second cover-constituting member and the second cover-constituting member can be slid to the side of the first cover-constituting member by a force from outside so that the first bag-shaped member would be broken to release the medium contained therein, wherein the cap member can be rotated by a force from outside to push into the side of the second cover-constituting member so that the second bag-shaped member would be broken to release a disinfectant contained therein, and wherein through holes are formed in the partition or the partition member so that the medium and the disinfectant can be communicated with the space;

(49) the apparatus for detecting the microorganism according to the above (48), characterized in that, an engagement of the first cover-constituting member with one end of the second cover-constituting member is secured by use of an uneven surface (e.g. an indented surface including a recess and a protruding portion) made on the contacting surfaces between the members and, when the body of the second cover-constituting member is slid by a force from outside to the side of the cover-constituting member, the first bag-shaped member can be broken whereby the medium contained therein can be removed.

(50) the apparatus for detecting the microorganism according to the above (48), characterized in that, an engagement of the second cover-constituting member with the cap member is in a screw-fixed manner and, the cap member can be rotated relative to the second cover-constituting member by a force from outside and pushed into a side of the container, whereby the second bag-shaped member would be broken to discharge the disinfectant contained therein;

(51) the apparatus for detecting the microorganism according to the above (48), characterized in that, the first and second cover-constituting members are constituted from a cylindrical body;

(52) the apparatus for detecting the microorganism as shown in FIG. 17 or FIG. 18 or that which is characterized in having substantially the same function concerning the bactericidal treatment of the incubated microorganism;

(53) the apparatus for detecting the microorganism according to the above (52), equipped with a cap member having the structure as shown in FIG. 19 or FIG. 20 or that which is characterized in having substantially the same function;

(54) the apparatus for detecting the microorganism according to the above (52), equipped with a cover-constituting member having the structure as shown in FIG. 22 or FIG. 23 or that which is characterized in having substantially the same function;

(55) the apparatus for detecting the microorganism according to the above (52), equipped with a cover-constituting member having the structure as shown in FIG. 26 or FIG. 27 or that which is characterized in having substantially the same function;

(56) the apparatus for detecting the microorganism according to the above (48), characterized in that, one or more convex parts on the side of the first cover-constituting member are formed as a structure having different installing regions, such as 781, 782, and one or more concave parts suitably engaged with the convex part(s) are formed on the contacting surface of the second cover-constituting members, the contacting surface contacting the first cover-constituting member, wherein, before use, it is possible to engage the first cover-constituting member with the second cover-constituting member in such a manner that the concave part is not inserted into the convex part whereby, the second cover-constituting member would be fixed within the first cover-constituting member in a nonsliding manner, and, upon use, it is possible to move the convex part into the concave part by rotating the second cover-constituting member, to ensure an engagement of the first cover-constituting member with one end of the second cover-constituting member by use of the concavities and convexities made on the contacting surfaces thereof and, to slide the body of the second cover-constituting member to the side of the first cover-constituting member via a force from outside whereby the first bag-shaped member would be broken and the medium contained therein removed;

(57) the apparatus for detecting the microorganism according to the above (56), characterized in being equipped with a cover-constituting member having the structure as shown in FIGS. 36 to 40 or that which has substantially the same function; and

(58) the apparatus for detecting the microorganism according to the above (56), characterized in being equipped with a cover-constituting member having the structure as shown in FIGS. 41 to 44 or that which has substantially the same function.

Still another aspect of the present invention is to provide:

(59) the apparatus for detecting the microorganism according to any of the above (1) to (58), comprising a medium selected from the group consisting of:

(a) a medium for Salmonella having a composition substantially containing an appropriate amount, such as 3 to 7 g, of tryptone, an appropriate amount, such as 1 to 6 g, of yeast extract, an appropriate amount, such as 5 to 15 g, of lysine, an appropriate amount, such as 0.5 to 2 g, of glucose, an appropriate amount, such as 7 to 9 g, of sodium chloride, an appropriate amount, such as 1.0 to 2.0 9, of monopotassium dihydrogen phosphate, an appropriate amount, such as 0.1 to 0.3 g, of sodium thiosulfate, an appropriate amount, such as 0.2 to 0.4 g, of ammonium iron citrate, an appropriate amount, such as 15 to 25 g, of magnesium chloride, an appropriate amount, such as 27 to 33 ml, of 0.4% Malachite Green solution and an appropriate amount, such as 0.01 to 0.03 g, of Bromcresol Purple per 1,000 ml of the medium (pH of the medium being about 5.3 to 5.7);

(b) a medium for *Vibrio parahaemolyticus* having a composition substantially containing an appropriate amount, such as 25 to 40 g, of a salt polymyxin broth (the salt polymyxin broth contains an appropriate amount of yeast extract, an appropriate amount of peptone, an appropriate amount of sodium chloride and an appropriate amount polymyxin B), an appropriate amount, such as 15 to 25 g, of mannitol, an appropriate amount, such as 5 to 10 g, of sodium citrate, an appropriate amount, such as 0.1 to 0.3 g, of sodium thiosulfate and an appropriate amount, such as 0.01 to 0.03 g, of Bromocresol Purple per 1,000 ml of the medium (pH of the medium being about 7.0 to 7.4);

(c) a medium for *Escherichia coli* group having a composition substantially containing an appropriate amount, such as 26 to 43 g, of a lauryl sulfate broth (the lauryl sulfate broth contains an appropriate amount of tryptose, an appropriate amount of lactose, an appropriate amount of monopotassium dihydrogen phosphate, an appropriate amount of dipotassium monohydrogen phosphate, an appropriate amount of sodium chloride and an appropriate amount of sodium lauryl sulfate), an appropriate amount, such as 3 to 8 g, of lactose and an appropriate amount, such as 0.03 to 0.05 g, of Bromthymol Blue or Bromocresol Purple per 1,000 ml of the medium (pH of the medium being about 6.75 to 7.25); and (d) a medium for Staphylococcus having a composition substantially containing an appropriate amount, such as 5 to 15 g, of tryptone, an appropriate amount, such as 2 to 8 g, of yeast extract, an appropriate amount, such as 5 to 15 g, of mannitol, an appropriate amount, such as 2 to 8 g, of dipotassium monohydrogen phosphate, an appropriate amount, such as 5 to 6 g, of lithium chloride, an appropriate amount, such as 12 to 20 g, of glycine, an appropriate amount, such as 10 to 14 g, of sodium pyruvate, an appropriate amount, such as 12 to 18 ml, of 1% aqueous potassium tellurite solution and an appropriate amount, such as 0.02 to 0.03 g, of Phenol Red per 1,000 ml of the medium (pH of the medium being about 7.25 to 7.75);

(60) the apparatus for detecting the microorganism according to any of the above (48) to (58), characterized in using a medium selected from the improved media described in Example 11; and

(61) the apparatus for detecting the microorganism according to the above (1), characterized in that, after collecting the sample for incubation by use of the microorganism-collecting part, all steps:

(a) supply of the medium into a container, (b) incubation of the microorganism on the medium in the container, (c) detection and/or finding of the microorganisms and (d) disinfection and/or sterilization of the medium in the container after incubation can be conducted in a substantially tightly closed system and the apparatus is portable.

Another aspect of the present invention is to provide:

(62) the apparatus for detecting the microorganism according to any of the above (1) to (5) wherein the microorganism is detected through incubating the microorganism in a medium and observing the changes in the medium, characterized in that the apparatus comprises (i) a microorganism-collecting part, (ii) a medium and (iii) a disinfectant, wherein at least a part of (i) the microorganism-collecting part and (ii) the medium can unitedly contact each other, by the action of a force from outside, during the incubation of the microorganism, the above-mentioned microorganism-collecting part (i) and the above-mentioned medium (ii) being at least located in a storage container in a noncontact manner, and wherein, after incubation of the microorganism, at least the incubated microorganism and the disinfectant (iii) can unitedly contact each other by the action of a force from outside, at least the above-mentioned disinfectant (iii) and the above-mentioned medium (ii) being located in the storage container in a noncontact manner;

(63) the apparatus for detecting the microorganism according to any of the above (1) to (62) wherein the container comprises a cover for closing and opening, the cover accommodating a bag-shaped member which encloses the medium;

(64) the apparatus for detecting the microorganism according to any of the above (1) to (63) wherein the container comprises a cover member for closing and opening the container, the cover member accommodating a bag-shaped member which encloses the disinfectant;

(65) the apparatus for detecting the microorganism according to any of the above (1) to (64) wherein the cover has a structure for allowing it to hold and carry at least (i) a first bag-shaped member containing a medium, and (ii) a second bag-shaped member containing a disinfectant independently each other;

(66) the apparatus for detecting the microorganism according to any of the above (1) to (65) wherein the cover comprises at least (i) a first cover-constituting member accommodating the first bag-shaped member, and (ii) a second cover-constituting member accommodating the second bag-shaped member;

(67) the apparatus for detecting the microorganism according to any of the above (1) to (66), comprising structure for protection and engagement, being disposed in the first and second cover-constituting members so as not to break the first bag-shaped member by moving the second cover-constituting member prior to use;

(68) the apparatus for detecting the microorganism according to any of the above (1) to (67), wherein the second cover-constituting member is equipped with a cap member and structure for protection and engagement is disposed in the second cover-constituting member and the cap member so as not to break the second bag-shaped member by moving the cap member prior to use;

(69) the apparatus for detecting the microorganism according to the above (67) or (68), wherein the structure for protection and engagement is a combination of a stopper (1005, 1008) and a guide (1004, 1007);

(70) the apparatus for detecting the microorganism according to any of the above (67) to (69), wherein the guide has a shape selected from the group consisting of shape a, b, c and d as shown in FIG. 70;

(71) the apparatus for detecting the microorganism having a structure as shown in any of FIGS. 53 to 64 or characterized in having substantially the same function concerning the bactericidal treatment of the incubated microorganism culture;

(72) a method for quantitatively measuring the number of viable microorganism cells in a sample or specimen through using the apparatus for detecting the microorganism according to any of the above (1) to (58) and (60) to (70);

(73) the method according to the above (72), wherein the measurement is carried out in a closed system after collecting a microorganism to be measured and transferring it into the apparatus according to any of the above (1) to (58) and (60) to (70); and

(74) the method according to the above (72) or (73), wherein a target is the number of viable microorganism cells prior to incubation.

The above objects and other objects, features, and advantages of the present invention are readily apparent from the following detailed description of the best mode for carrying out the invention when taken in connection with the accompanying drawings.

BRIEF DESCRIPTION OF THE DRAWINGS

Referring to the several drawing figures, wherein like numerals refer to like parts throughout, and wherein:

FIGS. 2a and 2b are schematic views showing an example of how to use the microorganism-detecting apparatus of FIG. 1;

Figure 1:
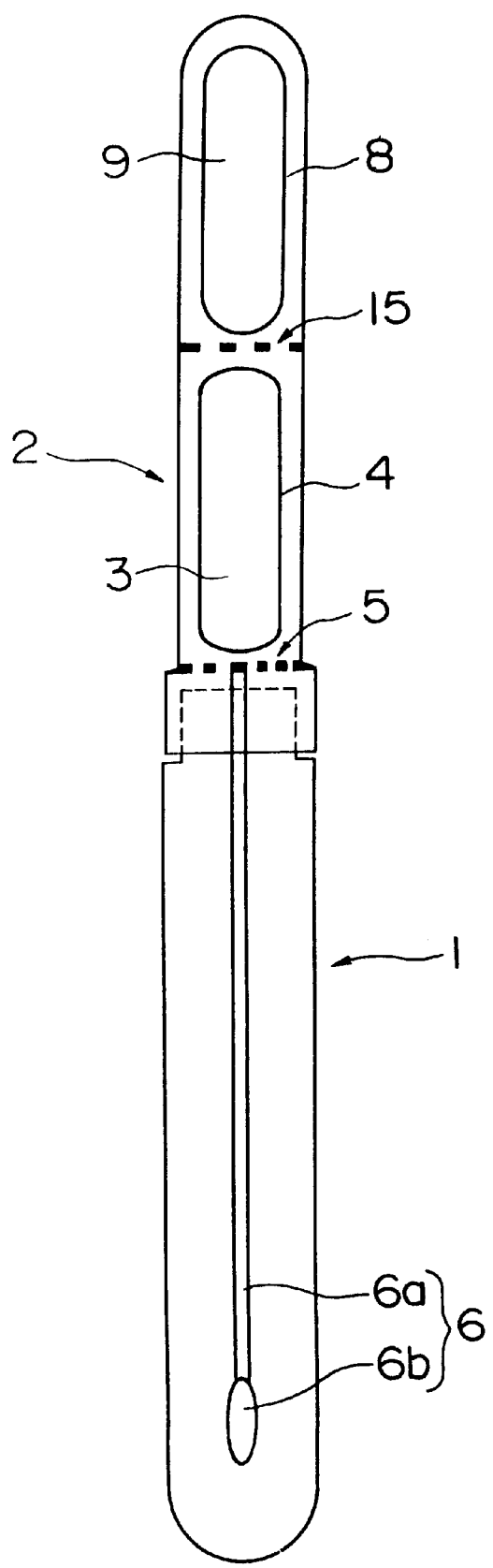
FIG. 1 is a schematic side cross sectional view showing an embodiment of the microorganism-detecting apparatus of the present invention.

Explanation of the symbols (numerals) used is as follows:
1, 21, 41, 61, 81, 101, 241 and 741: main body of container
2, 22, 42, 62, 82, 102 and 242: cover
3: medium
4, 24, 44, 64 (or 68), 84, 104, 244 and 744: first bag-shaped member or vessel
6, 26, 46, 66, 86, 106, 246 and 746: microorganism-collecting member (part)
6a, 26a, 46a, 66a, 86a, 106a, 246a and 746a: rod-shaped element (stem)
5 and 296: first partition member
15 and 235: second partition members
6b, 26b, 46b, 66b, 86b, 106b, 246b and 746b: microorganism-collecting end
7: disk member impregnated with antibiotic substance
9: disinfectant/sterilizer
20: guide member
11, 59, 79, 89, 109, 259 and 776: connecting part of the container with the cover
8, 28, 48, 68 (or 64), 88, 108, 248 and 748: second bag-shaped member or vessel

BEST MODE FOR CARRYING OUT THE INVENTION

The present invention relates to an apparatus for the detection of microorganisms which is particularly portable or is able to be carried easily, the apparatus being capable of initiating the incubation of the microorganism immediately at the place where the microorganism is collected and/or being capable of starting in the incubation of the microorganism without skillfulness. It is understood that the apparatus for detecting microorganisms in accordance with the present invention is relatively small in size, portable and, after incubation of the microorganisms, able to conduct the detecting steps until the disposal of the used apparatus in a substantially tightly closed system containing the incubated microorganism.

The term "substantially tightly closed system" used here means that, although it is possible to incubate, find or detect the microorganism and to disinfect and/or sterilize the incubated microorganism to a disposable extent, the cultured pathogenic microorganism does not diffuse to outside or to the environment during the incubating period and/or the incubated pathogenic microorganism does not come to the outside or environment by diffusion until the completion of its disinfection and/or sterilization, or it does not pollute the outside or environment, and the term further means that such a function can be achieved.

In the microorganism-detecting apparatus of the present invention as mentioned above, the medium which is to give an incubating condition suitable for the incubation of the microorganism, and the microorganism-collecting part are located in a noncontact manner relative to each other upon a non-using stage, and during the incubation for the detection of the microorganism, the specific medium and microorganism-collecting part contact each other whereby the status suitable for proliferation of the microorganism is achieved and, after use, the apparatus can be safely disinfected and/or sterilized.

In the present invention, the medium is further made in an appropriate state where the specific species of the microorganism (food poisoning microorganisms such as *Staphylococcus aureus*) are proliferated but other microorganisms (i.e. those other than *Staphylococcus aureus* such as Salmonella, *Escherichia coli*, *Vibrio parahaemolyticus* and other intestinal microorganisms) are substantially unable to grow. After the detection, a treatment for disposal of the apparatus can be conducted by a simple operation and a safe disposal is made possible at all times.

Accordingly, when an appropriate incubating structure (such as a simple incubator) and detecting structure (such as a pH indicator which detects the changes in pH due to growth of the microorganism) of the microorganism are utilized, it is now possible to easily detect the specific species of microorganisms (such as food poisoning ones) and anyone is able to easily dispose the apparatus after use. When an apparatus which is in such a status that it gives an incubating condition having a selectivity to specific species of microorganisms (for example, food poisoning ones such as *Staphylococcus aureus*) is used, it is now easy to selectively detect and identify (i.e. to discriminate the type of the food poisoning microorganism) the specific species of the microorganisms (such as food poisoning ones) and to disinfect and sterilize the apparatus containing the pathogenic microorganisms without anxiety.

Examples of the pathogenic microorganism are *Staphylococcus aureus*, *Vibrio parahaemolyticus*, Salmonella (such as *Salmonella typhi*, *Salmonella paratyphi A*, *Salmonella schottmuelleri*, *Salmonella enteritidies*, *Salmonella thompson*, *Salmonella narashino*, *Salmonella potsdam*, *Salmonella oranienburg* and *Salmonella senftenberg*), *Clostridium botulinum*, Shigella (such as *Shigella dysenteriae* and *Shigella flexneri*), *Vibrio cholerae*, *Vibrio cholerae* biotype eltor and *Escherichia coli* (such as enteropathogenic *Escherichia coli* represented by *E. coli* O-157).

When the apparatus is used for detection of food poisoning, the apparatus of the present invention can be preferably made in such a mariner that it shows a selective incubating ability for at least one microorganism selected from the group consisting of *Staphylococcus aureus*, *Vibrio parahaemolyticus* and Salmonella, which occupy nearly all (about 99%) of the microorganisms causing food poisoning while the discrimination among those types of microorganism may not be essential. This is because, when the presence of at least one of these three types of microorganisms is confirmed, then it is possible to substantially remove all of the three types of microorganisms from the environment, by applying a certain disinfectant as mentioned later, to the environment. When the food poisoning microorganism can be detected and identified in a manner as mentioned above (such as spontaneously), it is now possible to prevent food poisoning easily and effectively by adopting a measure suitable for removing the food poisoning microorganism (such as by a disinfecting method where cooking devices, etc. are cleaned with "Hibiden" (trade name: SUMITOMO PHARMACEUTICALS CO. LTD., Japan, for a 0.2 to 0.5% solution of chlorohexidine) or with an invert soap followed by wiping and washing with water).

On the other hand, if it is necessary to identify by discriminating each of *Staphylococcus aureus*, *Vibrio parahaemolyticus*, Salmonella and pathogenic *Escherichia coli* O-157 as a microorganism causing the food poisoning for the sake of the countermeasure, it is also possible that a selective incubating ability is given to the microorganism-detecting apparatus used, or a selective identifying ability is given to the detecting function.

If necessary, the apparatus for detecting microorganisms in accordance with the present invention may be constituted in such a manner that a selectivity for incubation of the "big three" food poisoning microorganisms (i.e. *Staphylococcus aureus*, *Vibrio parahaemolyticus* and Salmonella; about 99% of the bacterial food poisoning is caused by any of them) is given. It is also possible to give a selectivity for incubation of enterohaemorrhagic *Escherichia coli* (such as *E. coli* O-157:H7) which has been an increasingly big problem in recent years. It is further possible to give a selectivity for incubation of antibiotic-resistant microorganism such as MRSA.

The present invention will now be further illustrated by, if necessary; referring to the attached drawings.

FIG. 1 and FIGS. 3 to 16 show outer appearances, cross sections along the side of the apparatus, etc. of one of the preferred embodiments of the present invention.

First, an illustration will be made by referring to FIG. 1. The detecting apparatus in this embodiment is constituted from a hollow and cylindrical container (1) having an opening at the upper end and a cover (2) which can be freely inserted into and detached from the opening. At the upper part of the cover (2) (i.e. an opposite side to the container opening of the cover (2)), a first bag-shaped member or vessel is placed which encloses a medium (3) suitable for the incubation of a specific microorganism such as *Staphylococcus aureus*. At the upper part thereof, a second bag-shaped member or vessel (8) is placed which encloses a disinfectant (9) having a sufficient concentration or amount for disinfecting and/or sterilizing the incubated microorganism. The medium (3) further contains a pH indicator (such as Phenol Red, Bromcresol Purple and Bromthylmol Blue) which identifies the pH changes due to proliferation of the microorganism. On the other hand, at the lower side (an opening side of the container) of the first bag-shaped member (4), a partition member (5) having one or more (preferably, more than one) hole(s) is disposed (e.g. embedded) which prevents falling of the first bag-shaped member (4) into an opening of the container. Further, at the lower side (at the side of the first bag-shaped member) of the second bag-shaped member or vessel (4), a partition member (15) having one or more (preferably, more than one) hole(s) is disposed (e.g. embeded) which prevents falling of the second bag-shaped member (8) downward. In order to restrict such a downward movement of the first bag-shaped member (4) and the second one (8), there will be no need of using the partition members (5 and 15) but the structure having the same function, including, for example, an element constituting the cover (2) and having one or more through holes (i.e., a perforated portion in the partition part thereof), will suffice.

Further, at the nearly central part of the bottom side of the cover (2), a microorganism-collecting member (part) (6) extending to an almost vertical direction to the opening side of the above container is placed. The microorganism-collecting part (6) consists of a rod-like material (stem) (6a) located at the side near the cover (2) and a microorganism-collecting end (6b) located at the end (a far side from the cover (2)) of the rod-like material. Usually, the microorganism-collecting end (6b) is received in such a manner that it does not contact with the medium before use. The microorganism-collecting end (6b) is to achieve a selective incubation and, usually, the end is received in such a manner that it does not contact with an antibiotic substance having a function of inhibiting the specific microorganism. However, as will be mentioned below in detail, it may be, if necessary, in such a state that some contact with the antibiotic substance is available or that the antibiotic substance is given at the microorganism-collecting end.

Examples of the antibiotic substance are those having a characteristic nature of effectively inhibiting the proliferation of the microorganisms other than specific ones to be detected (e.g., food poisoning microorganisms such as enteropathogenic *Escherichia coli* and Salmonella and resistant microorganisms such as MRSA). When microorganisms which cause food poisoning (such as *Staphylococcus aureus, Vibrio parahaemolyticus* and Salmonella) are used as the microorganisms to be detected, examples of the antibiotic substance are aztreonam, polymyxin B, fluconazole and a combination thereof. When an antibiotic-resistant microorganism is used as the microorganism to be detected, the examples are oxacillin which inhibits Gram-positive bacteria having no resistance, polymyxin B and aztreonam which inhibits Gram-negative bacteria, polymyxin B as well as a combination thereof.

The antibiotic substance may, as will be mentioned later, be previously added to the medium, coated on the part of the container (1) used for incubation (such as a bottom or the container (1) or a wall near there), present as a powder which is made to be easily dissolved, or coated at the place which is a part of the microorganism-collecting part (such as the place which is just above the microorganism-collecting end (6b)). It is also possible that the antibiotic substance is placed separately from the part used for incubation in the above-mentioned container, the medium (3) or the microorganism-collecting part (6). In an embodiment where the antibiotic substance is placed separately as such, a disk-shaped member (7) (refer to FIG. 5; preferably composed of "porous material") to which the antibiotic substance is given may, if necessary, be placed at the inner area of the container (1) (such as a space between the microorganism-collecting end (6b) and the bottom of the container). Alternatively, the antibiotic substance may be placed in such a manner that it is supplied when the medium (3) enclosed in the first bag-shaped member (4) (which will be mentioned below) falls down into the container. In such an embodiment, it is also possible that the antibiotic substance is placed at the partition member (5) or at the upper side of the guiding material (20) (cf. FIG. 4).

Figure 3:
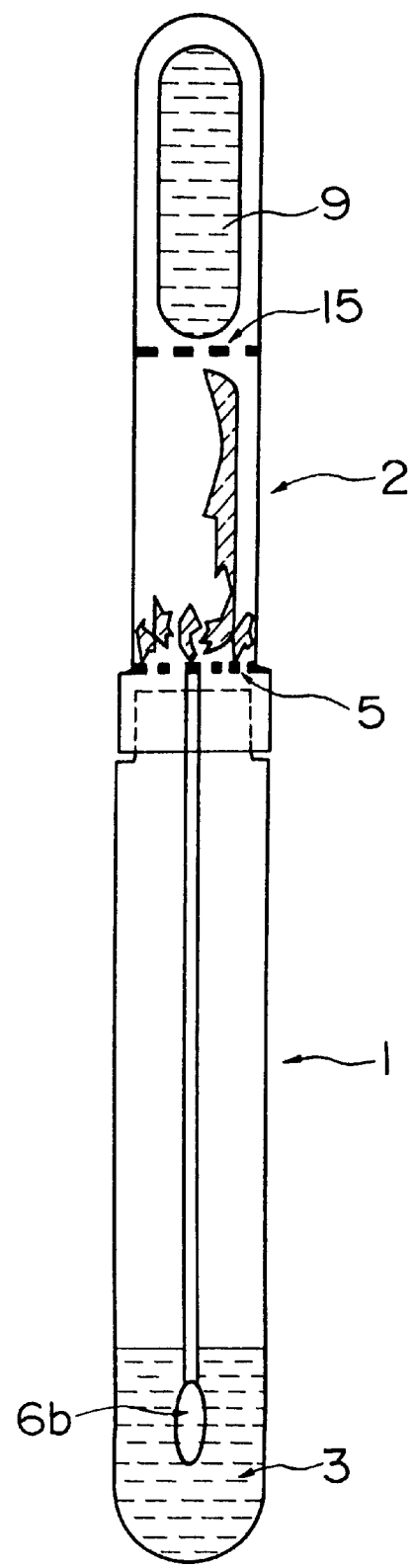
FIG. 3 is a schematic view showing an example of how to use the microorganism-detecting apparatus of FIG. 1.

When a microorganism-detecting apparatus in such an embodiment as shown in FIG. 1 is used, a cover (2) having a microorganism-collecting part (6) is at first taken out from the container as shown in FIG. 2(a). Then, as shown in FIG. 2(b), the microorganism-collecting end (6b) at the end of the microorganism-collecting part (6) is rubbed on an object to be tested (10) (such as a chopping board) and the microorganism existing on the object to be tested (10) is collected on the microorganism-collecting end (6b). Then the cover (2) having the microorganism-collecting part (6) is inserted into the container again and, after that, as shown in FIG. 3, the first bag-shaped member (4) is broken (by, for example, strongly compressing it from outside of the cover (2) using a compressing structure which is not shown here) so that the medium (3) which is enclosed and received in said first bag-shaped member (4) falls down into the container through the holes of the partition member (5). As a result, the microorganism-collecting end (6b) of the microorganism-collecting part (6) is dipped into the medium (3). At that time, falling of the materials other than the medium such as the broken pieces of the first bag-shaped member (4) is inhibited by the partition member (5) and does not fall down into the container.

For example, as mentioned hereinabove, when an antibiotic substance having a specific selectivity is attached to the microorganism-collecting end (6b), proliferation of the microorganisms other than the specific microorganism (such as food poisoning microorganisms including *Staphylococcus aureus* and *Clostridium botulinum*) is substantially inhibited in case the microorganism-collecting end (6b) of the microorganism-collecting part (6) is dipped in the medium (3) as such. Accordingly, when the microorganism-detecting apparatus in such a state is subjected to an incubation by an appropriate incubating structure (such as a simple incubator), the specific microorganism (such as food poisoning microorganism including *Staphylococcus aureus* and *Clostridium botulinum*) is selectively proliferated. There is no particular limitation for the incubating condition at that time but, usually, the condition of 37° C. for about 16 to 24 hours is sufficient. After the above-mentioned incubating operation, a change, if any, of the pH indicator contained in the medium (3) (and also the degree of changes in color) is checked whereby the specific food poisoning microorganism (such as *Staphylococcus aureus*) can be easily detected and identified (i.e. discrimination of the type of the food poisoning microorganism is conducted). For example, the medium containing Phenol Red as a pH indicator shows a pink color (pH: 7.4) in the initial stage of incubation and, when *Staphylococcus aureus* is present, it changes to yellow whereby a detection can be done. In addition, physical and chemical changes in the nature and appearance resulting from the substances which are produced by the proliferated microorganism or obtained due to a decomposition thereby, turbidity of the medium and growth of colony are observed as a change in the medium whereby the presence of the microorganism may be judged as well. From a viewpoint of observation by the naked eye as such, it is preferred that the container (1) has a light-transmitting ability such as that at least the area wherefrom the observation is conducted is transparent. When there is a possibility that the medium, the antibiotic substance, etc. are affected by light to change their nature, then the transparent area may be in such a constitution that it is covered by a light-shielding coat and, upon observation, it is detached.

Finally, the apparatus where the microorganism is incubated and detected is disposed of and, for such a purpose, it is necessary that the incubated cells, cultured products, inner side of the container, etc. are completely disinfected/sterilized. Although not shown in the figures, the second bag-shaped member (8) is broken (by applying a sufficient force for disintegration or by strongly compressing from outside of the cover (2) using, for example, a disintegrating mechanism or compressing device which is not shown) whereby the disinfectant (9) enclosed and received in the second bag-shaped member (8) falls into the container through the holes of the partitions (5 and 15). As a result, the microorganism-collecting end (6*b*) of the microorganism-collecting part (6) and the medium (3) containing the incubated microorganism are dipped in and/or mixed with the disinfectant (9). For a complete disinfection/sterilization at that time, it is preferred to shake the container so that the disinfectant (9) comes throughout the inside of the container (1) and, since a treatment is conducted in a substantially tightly-closed system in the present invention, it is possible to conduct a safe and sure disinfecting/sterilizing operation.

Constitution of each part of the apparatus for detection of microorganisms in accordance with the present invention will be illustrated as follows:

Container

It is preferred that the container is constituted from a transparent or translucent material. To be more specific, the container may be formed using an inorganic material such as glass or an organic material such as plastics (e.g., polyethylene, polypropylene, polystyrene, polyethylene terephthalate (PET), polycarbonate, acryl resin and polyolefin) and, when weight and possibility of breakage upon centrifugal operation, etc. are taken into consideration, it is preferred that the container is constituted from plastics.

There is no particular limitation for the shape of the container so far as it has an opening at the upper end and a cover (2) can be freely attached to and detached from the opening. To be more specific, in addition to the shape of a test tube as shown in the figures, any of shapes in flask, bottle, etc. may be used.

Cover

There is no particular limitation for the material which constitutes the cover (2) but the material may be the same one as that used for the container. In another embodiment, the cover (2) may be preferably constituted from a material which is softer than that used for the container for lowering the possibility of damage of the container and for increasing the contact adherence with said container. To be more specific, both container and cover may be constituted from polypropylene (PP) or, when the container is constituted from hard plastics or hard resin such as polystyrene and PET, the cover (2) may be constituted from soft plastics such as polyolefin or soft resin (this term is intended to use for covering elastic materials or elastomers as well) or, in some cases, that is rather preferred. The cover is a material having a part placed for connecting to a mouth or a wall of the container. The cover may be in such a form that it is fixed to the container by use of either a screw thread or bayonet, or is fixed at the certain position by deformation of a connecting part. It is also possible to place a packing or the like at the connecting part of the cover with the container. All or a part of the material which constitutes the cover may be colored for discrimination or may be printed with letters, signs, pictures, etc.

In preferred specific examples, the cap part at the top of the cover may be of a different color for each microorganism to be tested so that the type, etc. of the microorganism to be tested can be easily understood and the part may be suitably colored or modified with letters, signs, pictures, etc. It is also possible to use a material which has its color by itself.

In the apparatus of the present invention, it is preferred that the cover (2) can receive at least two bag-shaped members as shown in FIG. 1, FIGS. 4 to 7 and FIGS. 10 to 16, where the first bag-shaped member receives a medium while the second one receives a disinfectant/bactericide.

Bag-Shaped Material

A. Medium

There is no particular limitation for the material, shape, etc. of the first bag-shaped member or vessel (4) so long as the first bag-shaped member (4) can surely and stably enclose the medium (3) upon storage and transportation of the microorganism-detecting apparatus, and a predetermined amount of the medium (3) can be surely released upon incubation of the microorganism.

To be more specific, material for the first bag-shaped member (4) may be a hard material such as glass and hard plastics or a soft one such as soft plastics (e.g., polyethylene and polypropylene) and flexible material (e.g., paper) but, in view of ease of confirming the presence of the enclosed medium and the color tone, etc. thereof, it is preferred to use a transparent or translucent material.

In the present invention, there is no particular limitation for the structure for releasing the medium (3) from the fist bag-shaped member (4) so long as the medium (3) is placed at a position appropriate for incubation upon the incubation of the microorganism. To be more specific, upon releasing the medium (3) from the first bag-shaped member (4), the member (4) may be subjected to any of the operations including perforation, cutting and breakage. When perforation, cutting, etc. of the first bag-shaped member (4) is conducted, a tool such as a needle-like member or an edge-like member whereby perforation or cutting is made easy (not shown in figures), may be installed at the inner wall of the cover (2) if necessary. On the other hand, in an embodiment where the medium (3) is released by breaking the first bag-shaped member (4), it is preferred in terms of ease of said breakage that the first bag-shaped member (4) be composed of a hard material such as glass and hard plastics. In a structure where a substantially tight-sealed system can be maintained and a sufficient breaking force from outside can be applied to the bag-shaped member, it is possible to easily apply a strong tension to such a hard material and to break it whereby the contents can be removed therefrom. An example of the preferred structure is that a strong tension is concentrated on a specific area (that may be two or more areas but a considerably narrow area is preferred) of the bag-shaped member made of a hard material. As will be mentioned in detail by referring to FIGS. 6 to 16 hereunder, it is to be understood that such breakage can be achieved by various structures, and it is also possible to adopt a structure where known structures and conventional structures are applied to the microorganism-detecting apparatus, or intalled within the microorganism-detecting apparatus of the present invention.

B. Disinfectant/Bactericide

In the present invention, there is no particular limitation for the material, shape, etc. of the second bag-shaped member or vessel (8) so long as the disinfectant/bactericide (9) can be safely and surely enclosed and received by the second bag-shaped member (8) during the storage/transportation of the microorganism-detecting apparatus until use, and during incubation of the microoganism, and so long as a predetermined amount of the disinfectant/bactericide (9) can be surely released upon disposal of the apparatus after use.

To be more specific, the material of the bag-shaped member can be selected from those which are used for the already-mentioned first bag-shaped member, and it is preferably a transparent or translucent material with the purposes that the receiving disinfectant/bactericide (9) can be stably and surely enclosed and the presence of the predetermined amount of the disinfectant/bactericide can be surely confirmed when the incubated microorganism is sterilized/disinfected, or that confirmation of color tone, etc. can be done in any easy manner from a viewpoint of confirmation that the sterilizing/disinfecting treatment was surely done.

In the present invention, there is no particular limitation for the structure for releasing the disinfectant/bactericide (9) from the second bag-shaped member so long as the disinfectant/bactericide is positioned in a place suitable for the disinfecting/sterilizing treatment upon the disposing stage of the microorganism-detecting apparatus. To be more specific, it is possible to use any structure capable perforating, cutting, breaking, etc. the second bag-shaped member (8) for releasing the disinfectant/bactericide (9) from the second bag-shaped member (8). When perforation, cutting, etc. of the second bag-shaped member (8) is conducted, a tool such as a needle-like member or an edge-like member, whereby perforation or cutting is made easy (not shown in figures), may be installed at an inner wall of the cover (2) if necessary. On the other hand, in an embodiment where the disinfectant/bactericide (9) is released by breaking the second bag-shaped member (8), it is preferred in terms of ease of the breakage that the second bag-shaped member (8) be composed of a hard material such as glass and hard plastics.

In the structure where a substantially tight-sealed system can be maintained and a sufficient breaking force from outside can be applied to the bag-shaped member, it is possible to easily apply a strong tension to such a hard material and to break it, whereby the contents can be removed therefrom. An example of the preferred structure is that a strong tension is concentrated on a specific area (that may be two or more areas but a considerably narrow area is preferred) of the bag-shaped member of a hard material. As mentioned in detail by referring to FIGS. 6 to 16 hereunder, it is to be understood that such a thing can be achieved by various structures and it is also possible to adopt a structure where known structure and conventional structure are applied to the microorganism-detecting apparatus, or installed within the microorganism-detecting apparatus of the present invention. The force from outside may be that utilizing rotational movement, pushing-in movement, twist, etc.

Rod-Like Material

The rod like material (stem) (6a) of the microorganism-collecting part in the present invention is a material having a so-called auxiliary function, whereby a microorganism-collecting end (6b) having a function of direct collection of the microorganism to be tested can be stably supported avoiding a contamination and, in addition, the microorganism-collecting end (6b) is kept at a position suitable for contacting it with the medium (3) upon incubation of the microorganism. There is no particular limitation for the material, length, shape, etc. of the rod-like material (6a) so long as such functions of a stable holding and of a security for the contacting position are substantially achieved. In terms of prevention of contamination and softness upon collection of the microorganism, it is preferred that the rod-like material (6a) be composed of a flexible plastic.

Microorganism-Collecting End

In the present invention, the microorganism-collecting end (6b) of microorganism-collecting part is of a material such that it directly collects the microorganism, is capable of receiving the collected microorganism in a receiving container without contamination after collection of the microorganism, and also contacts with the medium (3) during incubation of the microorganism so that a condition suitable for incubation of the collected microorganism is provided. So long as such collecting and contacting functions are substantially achieved, there is no limitation for its structure but any structure will do and there is no particular limitation for the material, length, shape, etc. of the microorganism-collecting end (6b). To be more specific, the microorganism-collecting end (6b) may be, for example, just an end of the rod-shaped element (6a). However, for an object of easily achieving the above-mentioned collecting and contacting functions, it is preferred that the microorganism-collecting end (6b) has a an increased surface area.

Preferred examples of the "increased surface area" are a surface having one or more concavities (cutting, uneven surface, etc.) (such as an end like an ear pick or spatula) and a porous surface. In an embodiment where the microorganism-collecting end (6b) (at least a surface area thereof) is composed of a porous material, a porous material in a form of xerogel or a fibrous material is preferably used.

With regard to the fibrous material, filter paper, cottom (such as absorbent cotton), punch felt, cloth, knitted goods, nonwoven fabric, etc. may be used without particular limitation. It is also possible to use a structure where rubber or plastic material is used partially, a hollow structure or a plunger structure using an elastic material or a flexible material or a suckable structure together with a rod-shaped element (6a) which constitutes a microorganism-collecting part, whereby the sample can be easily collected when it is liquid. Particularly preferred is one in a shape of an applicator having cotton at its end.

Examples of the object (an object to be tested) wherefrom the microorganism is collected are usually utensils of cuisine, cooking devices, etc., home kitchen, toilet, bathtub, the place where food and beverage are sold, etc. Such an object is, for example, wiped with and dipped into the end of the applicator (microorganism-collecting end (6b)) as mentioned above. It goes without saying that, in that case, collection of the sample is usually conducted making sure that the applicator does not touch an unnecessary part or area. Other examples of the object wherefrom the microorganism is collected are food and food materials.

Medium

There is no particular limitation for the type, composition, etc. of the above-mentioned medium (3) so long as incubation of the expected microorganism to be detected (such as food poisoning microorganism or resistant microorganism) is possible, and known medium for such a microorganism or an improved medium thereof as well as a medium which is modified for better usability may be used. Preferably in the case of a food poisoning microorganism, it is possible to suitably select the medium by taking the compatibility (such as reactivity, intersolubility, etc.) with the later-mentioned antibiotic substances, pH indicator, etc. into consideration.

With regard to a medium for *Staphylococcus aureus,* it is possible to use mannitol-salt (modified) medium, Baird-Parker medium, tellurite-glycine medium, phenylethanol-azide medium, chocolate-agar medium, blood-agar medium, heart infusion agar medium, etc. in the present invention and, in view of the adaptability with the later-mentioned antibiotic substance for selecting *Staphylococcus aureus,* the use of a mannitol-salt (modified) medium is preferred.

As a medium for microorganism resistant to antibiotics such as MRSA, that which is prepared by adding oxacillin, aztreonam, polymyxin B, or the like to the afore-described medium may be preferably used.

As a medium for *Vibrio parahaemolyticus,* it is possible to use salt-polymyxin (modified) medium, cellobiose-polymyxin-colistin medium, thiosulfate-citrate-bile salts-sucrose medium, TCBS medium, MacConkey agar medium, blood-agar medium, etc. and, in view of the adaptability with the later-mentioned antibiotics for selecting *Vibrio parahaemolyticus,* the use of a salt-polymyxin (modified) medium is preferred.

As a medium for Salmonella, it is possible to use xylose-lysine (modified) medium, mannitol-lysine-Crystal Violet Brilliant medium, *Salmonella shigella* medium, deoxycholate-citrate-lactose-sucrose medium, DHL agar medium, MacConkey agar medium, etc. and, in view of the adaptability with the later-mentioned antibiotics for selecting Salmonella, the use of a xylose-lysine (modified) medium is preferred.

As a medium for *Escherichia coli,* it is possible to use BTB-lactose-agar medium, blood-agar medium, deoxycholate medium, LB medium, etc.

With regard to such a medium, it is possible to select from those mentioned in known literatures or from those prepared by modifying/varying the above-mentioned ones. Examples of the known literatures are Examined Japanese Patent Publication Hei-07/73,509 (JP Hei 07/73,509 B), Unexamined Japanese Patent Publication (Laid-Open) Hei-01/296, 998 (JP Hei 01/296,998 A), etc. for a medium for *Vibrio parahaemolyticus;* Laid-Open Japanese Patent Publications Sho-52/134,082 (JP Sho 52/134,082 A), Hei-06/217,760 (JP Hei 06/217,760 A), etc. for a medium for *Staphylococcus aureus;* Laid-Open Japanese Patent Publication Hei-02/65, 798 (JP Hei 02/65,798 A), Hei-05/130,859 (JP Hei 05/130, 859 A), Hei-06/22,791 (JP Hei 06/22,791 A), etc. for a medium for Salmonella; etc. as well as the references cited therein. In the present invention, a medium which is optionally modified/changed for adapting especially as a liquid medium is preferred.

Usually, a medium in a liquid state is preferably used and that filled or received in a tightly-sealable containers such as ampules or capsules is suitably used although it is not limited thereto but, for example, it may by in such a form that it can be supplied to an incubating space of the container separated by a partition or the like which can be easily broken by a force from outside.

The medium may be an agar medium and, for example, it may be in a form that it does not contact an antibiotic substance, being separated by a partition or the like which can be easily broken by a force from outside. It may be in such a form that, upon incubation, the partition is broken by pushing with an end of the microorganism-collecting rod constituted by a hard material; it is broken by hitting an iron piece or the like coated with glass, plastics or the like placed on the partition by means of a magnet placed outside; or, in addition to the above, a capsule of an antibiotic substance solution or a buffer solution is broken to flow the solution on a medium whereby the microorganism at the collecting end, the antibiotic substance and the agar medium are contacted. It may also be in such a form that dry medium or powder medium is received therein instead of the agar medium and is reconstituted to the conventional agar medium using an aqueous liquid such as a buffer solution which is received in various forms in the container of the microorganism-detecting apparatus.

In the case of the food poisoning microorganism, it is possible to detect and identify the microorganism by incubating as colonies (by means for a medium in a form of gel, for example). However, in a viewpoint of easiness of detection and identification of the food poisoning microorganism in usual restaurants and home, it is preferred to use a liquid medium giving a homogeneous incubating system to which a pH indicator or certain chemical substance capable of acting as an indicator after converted to decomposed product or metabolite as a result of decomposition or metabolism by the microorganism for proliferation of the microorganism is added whereby the judgment can be easily conducted by means of changes in color due to pH change or as viewed by the naked eye. The medium (3) may preferably be somewhat viscous so long as the detection/identification of the food poisoning microorganism by means of color change is not substantially disturbed.

Additives

If necessary, various additives may be added to the above-mentioned medium (3). In an embodiment of the present invention where detection of the microorganism to be detected is confirmed by means of pH change due to proliferation of the microorganism, it is preferred that a pH indicator is previously added to the medium. When such a pH indicator is used, pH of the medium changes as a result of production of acidic substances (such as lactic acid) by proliferation of the microorganism whereby the color tone of the indicator changes and, accordingly, confirmation of the proliferation becomes easy.

There is no particular limitation for the pH indicator which is applicable to the present invention. In view of pH change region, color tone, etc., Phenol Red, Cresol Red, Bromthymol Blue, Bromcresol Purple, triphenyltetrazolium, Blue Tetrazolium, etc. can be appropriately used. Such pH indicators may be used either solely or jointly by combining two or more if necessary. It is also preferred to use each of the pH indicators having different color tones (before changed) in each of the media for detecting different types of microorganisms because the microorganism to be detected can be easily recognized at a glance by means of such color tones.

Antibiotic Substances

In the present invention, it is also possible that the medium itself is bestowed with some selectivity to the microorganism but, usually, in order to make the selectivity sure, it is preferred that an antibiotic substance which effectively inhibits the proliferation of the microorganism other than the specific one to be detected and identified is jointly used upon necessity. This antibiotic substance is to achieve a selective incubation of the microorganism to be detected and has a function of inhibiting the proliferation of a microorganism which is other than the specific one to be detected. The type of the antibiotic substance used therefor may be selected depending upon the relation with the microorganism to be detected or may be selected by considering what kind of microorganism selectivity is to be bestowed depending upon the state upon actual use of the apparatus of the present invention.

The "selectivity" upon incubation of the microorganism can be adjusted or selected depending upon the purpose. For example, when a food poisoning microorganism is an object, it is preferred to have an incubation selectivity for one or more microorganisms selected from the group consisting of "*Staphylococcus aureus, Vibrio parahaemolyticus* and Salmonella" which occupy nearly all (around 99%) of the microorganisms causing food poisoning, while discrimination among those three microorganisms is not essential. However, from a viewpoint of a minute countermeasure to each of the characteristics of those food poisoning microorganisms, it is in some cases preferred to have an "incubation selectivity" whereby discrimination among "Staphylococcus aureus, Vibrio parahaemolyticus and Salmonella" is possible. In addition, there is a case where it is preferred to have an "incubation selectivity" whereby enteropathogenic Escherichia coli such as E. coli O-157 can be discriminatively detected.

In the present invention, there is no particular limitation for the antibiotic substance to be used so long as it is capable of effectively inhibiting a microorganism other than specific (one or more) microorganism(s) to be detected such as a food poisoning microorganism. Although the antibiotic substance may be used solely in some cases, preferably, two or more may be used jointly depending upon the purpose. The amount may be suitably decided especially depending upon the amount of the medium used. For example, in detecting a food poisoning microorganism, the following antibiotic substances are preferably used. In the following description, the concentration for each antibiotic substance is a suitable concentration at the incubating stage of the food poisoning microorganism (when unitedly used with the medium).

| <Antibiotic Substances Selective to Staphylococcus aureus> | |
|---|---|
| Aztreonam | 1 to 15 µg/ml |
| Polymyxin B | 1 to 15 µg/ml |
| Fluconazole | 1 to 10 µg/ml |

Combination of the above three antibiotic substances can be used preferably.

| <Antibiotic Substances Selective to Vibrio parahaemolyticus> | |
|---|---|
| Polymyxin B | 1 to 15 µg/ml |
| Fluconazole | 1 to 10 µg/ml |
| Potassium tellurite | 1 to 20 µg/ml |

Combination of the above three antibiotic substances can be used preferably.

| <Antibiotic Substance Selective to Salmonella> | |
|---|---|
| Fluconazole | 1 to 10 µg/ml |

Locating Position of the Antibiotic Substances

There is no particular limitation for the position or the place where the antibiotic substances are located or placed so long as they function unitedly with the medium (3) at the incubating stage of the microorganism. Preferably, it can be held at a disk member (7) as will be mentioned later in detail (cf. FIG. 5) while other methods are possible as well. Thus, to be more specific, the antibiotic substance may be previously added to a medium (3), coated on an inner wall of the container or bestowed at a certain place of the microorganism-collecting part (6) (the place being able to contact with the medium (3) upon incubation). Two or more of such positions may be applied if necessary. It goes without saying that, in those cases, the above-mentioned disk member (7) may be omitted. When the antibiotic substance is previously added to a medium (3), it is preferred, by taking inactivation of the antibiotic substance in the medium into consideration, to add the antibiotic substance in such a little amount that the inactivation (usually, a decrease in the antibiotic activity to an extent of around 30 to 35% when stored at ambient temperature for one year) can be supplemented.

When an antibiotic substance is received in a space which is used for incubation in a container, the antibiotic substance may be received in a powdery form but may be received as capsules or tablets which are easily dissolved upon contacting with a liquid such as a medium or, after its solution is added to a position to be used as a space for incubation in the container as mentioned above, it may be received by coating on an inner wall of the container by means of a vacuum drying or the like. Alternatively, the antibiotic substance in a form of an easily soluble powdery or a solution may be filled in a breakable ampule or capsule and received in a space used for incubation in the container in such a manner that it can be easily added. It may be received in any place of the container and may be received in such a manner that it can contact with the medium by shaking the container, by washing out with a liquid medium or by breaking the ampule by a force from outside before incubation. A preferred receiving method is that, before incubation, it keeps a noncontact state with the medium and, for example, the antibiotic substance may be placed at the partition member (5) or above the guide member (20).

On the other hand, in an embodiment where the antibiotic substance is located at a certain position of the microorganism-collecting part (6), it is preferred that the antibiotic substance is located at the rod-shaped member (6a) (the position where contact with the medium (3) is possible) of the microorganism-collecting part (6) and/or at the microorganism-collecting end (6b) which is an end of the microorganism-collecting part (6). When the antibiotic substance is placed at the microorganism-collecting end (6b), it may be impregnated into the microorganism-collecting end (6b) itself or, after preparing a multi-layered structure consisting of an inner layer (at the side of the rod-shaped element (6a) which is a microorganism-collecting end (6b) and an outer layer (for collecting the microorganism), the antibiotic substance is placed on the inner layer. Alternatively, the antibiotic substance may be impregnated in or coated on the upper half area of the microorganism-collecting end (6b).

Disk Member

Figure 5:
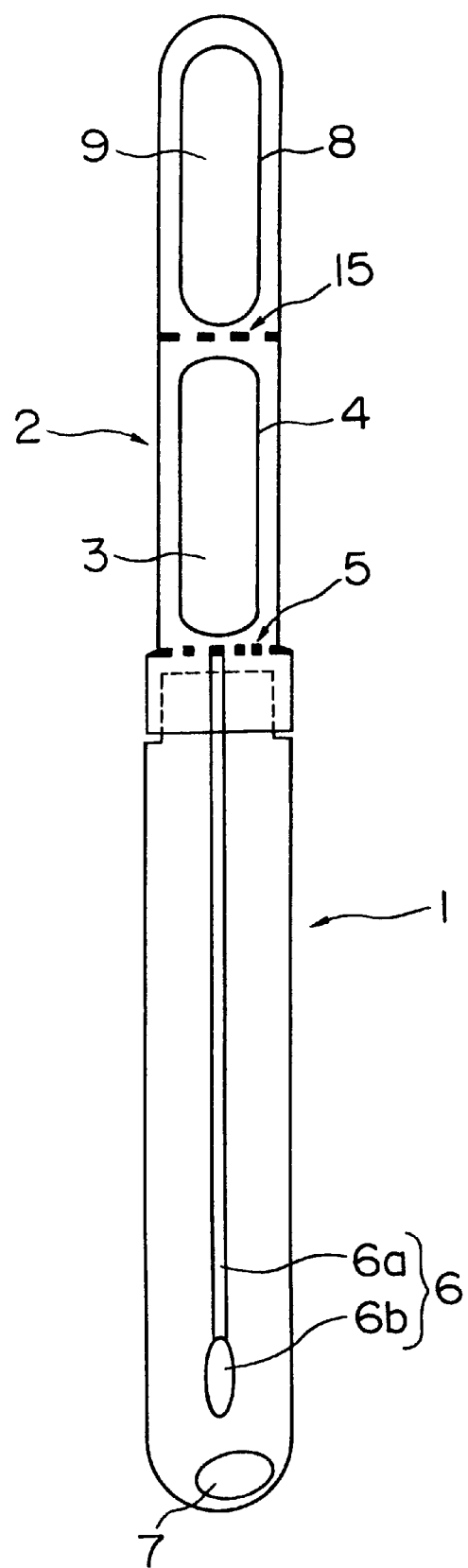
FIG. 5 is a schematic side cross sectional view showing another embodiment of the microorganism-detecting apparatus of the present invention.

A disk member (7) which is optionally used in the present invention is of a material having the functions of holding the antibiotic substance and for offering the condition suitable for incubation of the specific kind of microorganism upon contacting with the medium (3) during the incubation (cf. FIG. 5). There is no particular limitation for the material, length, shape, etc. of the disk member so long as such holding and contacting functions are substantially achieved. To be more specific, the disk member may be a simple board or a flat material but, in view of an easy and effective achievement of the above-mentioned holding and contacting functions, it is preferred that the disk member has an increased surface area. Examples of such "an increased surface area" are a surface with one or more concavities (cutting, uneven surface, etc.) and a porous surface.

In an embodiment where the disk member (at least its surface area) is composed of a porous material, the preferably used one is a xerogel-like porous material or a fibrous material. Examples of the fibrous material which are applicable without limitation are filter paper, cotton (such as absorbent cotton), punch felt, cloth, knitted goods, non-woven fabric, etc.

Examples of a medium which does not need a disk member (7) for holding the antibiotic substance, improves the operation ability of the microorganism-detecting apparatus, and is suitable as a liquid medium as well, are as follows:

(a) Composition of a Medium for Salmonella (per 1,000 ml of the medium):

An appropriate amount of tryptone, preferably 3 to 7 g, for instance, 5 g; an appropriate amount of yeast extract, preferably 1 to 6 g, for instance, 3 g; an appropriate amount of lysine, preferably 5 to 15 g, for instance, 10 g; an appropriate amount of glucose, preferably 0.5 to 2 g, for instance, 1 g; an appropriate amount of sodium chloride, preferably 7 to 9 g, for instance, 8 g; an appropriate amount of monopotassium dihydrogen phosphate, preferably 1.0 to 2.0 g, for instance, 1.6 g; an appropriate amount of sodium thiosulfate, preferably 0.1 to 0.3 g, for instance, 0.2 g; an appropriate amount of ammonium iron citrate, preferably 0.2 to 0.4 g, for instance, 0.3 g; an appropriate amount of magnesium chloride, preferably 15 to 25 g, for instance, 20.3 g; an appropriate amount of 0.4% Malachite Green solution, preferably 27 to 33 ml, for instance, 30 ml; and an appropriate amount of Bromcresol Purple, preferably 0.01 to 0.03 g, for instance, 0.02 g per 1,000 ml of the medium (pH of the medium being about 5.3 to 5.7);

(b) Composition of a Medium for Vibrio such as *Vibrio parahaemolyticus* (per 1,000 ml of the medium):

An appropriate amount of a salt polymyxin broth, for instance, 25 to 40 g (where a salt polymyxin broth contains an appropriate amount of yeast extract, an appropriate amount of peptone, an appropriate amount of sodium chloride and an appropriate amount polymyxin B); an appropriate amount of mannitol, preferably 15 to 25 g, for instance, 20 g; an appropriate amount of sodium citrate, preferably 5 to 10 g, for instance, 8 g; an appropriate amount of sodium thiosulfate, preferably 0.1 to 0.3 g, for instance, 0.2 g; and an appropriate amount of Bromocresol Purple, preferably 0.01 to 0.03 g, for instance, 0.02 g per 1,000 ml of the medium (pH of the medium being about 7.0 to 7.4);

(c) Composition of a Medium for *Escherichia coli* (per 1,000 ml of the medium):

An appropriate amount of lauryl sulfate broth, preferably 26 to 43 g, for instance, 35.6 g (the lauryl sulfate broth contains an appropriate amount of tryptose, an appropriate amount of lactose, an appropriate amount of monopotassium dihydrogen phosphate, an appropriate amount of dipotassium monohydrogen phosphate, an appropriate amount of sodium chloride and an appropriate amount of sodium lauryl sulfate); an appropriate amount of lactose, preferably 3 to 8 g, for instance, 5 g; and an appropriate amount of Bromthymol Blue or Bromocresol Purple, preferably 0.03 to 0.05 g, for instance, 0.04 g per 1,000 ml of the medium (pH of the medium being about 6.75 to 7.25); and (d) Composition of a Medium for Staphylococcus such as *Staphylococcus aureus* (per 1,000 ml of the medium):

An appropriate amount of tryptone, preferably 5 to 15 g, for instance, 10 g; an appropriate amount of yeast extract, preferably 2 to 8 g, for instance, 5 g; an appropriate amount of mannitol, preferably 5 to 15 g, for instance, 10 g; an appropriate amount of dipotassium monohydrogen phosphate, preferably 2 to 8 g, for instance, 5 g; an appropriate amount of lithium chloride, preferably 5 to 6 g, for instance, 5.5 g; an appropriate amount of glycine, preferably 12 to 20 g, for instance, 16.5 g; an appropriate amount of sodium pyruvate, preferably 10 to 14 g, for instance, 12 g; an appropriate amount of 1% aqueous potassium tellurite solution, preferably 12 to 18 ml, for instance, 15 ml; and an appropriate amount of Phenol Red, preferably 0.02 to 0.03 g, for instance, 0.025 g per 1,000 ml of the medium (pH of the medium being about 7.25 to 7.75).

Among the components for the medium, amounts of those which are added as nutrients such as tryptone, yeast extract, lysine, glucose, peptone, mannitol, tryptose and lactose may be either increased or decreased by persons skilled in the art depending upon the object and necessity, and it is to be understood that such a medium is also included in the coverage of the medium of the present invention. Examples of the components related to the selectivity of the microorganism to be detected are sodium chloride, Malachite Green, Bromcresol Purple, sodium thiosulfate, ammonium iron citrate, polymyxin B, sodium lauryl sulfate, Bromthymol Blue, lithium chloride, sodium pyruvate, potassium tellurite and Phenol Red. Since such components have considerable affects on the sensitivity of the microorganism detection, it is requested that the adding amounts are precisely selected. However, it is also acceptable to select the amounts which are out of the above-mentioned ranges after conducting normal tests or the like by incubating the microorganism known in the art and selecting and deciding the due amounts. It is to be understood that the medium with such a modification or improvement is also within a coverage of the present invention.

Those media are liquid ones having a fluidity and are particularly suitable for utilization in the microorganism-detecting apparatus of the present invention. Those media show excellent microorganism-detecting sensitivity and specificity to the microorganism and, at the same time, they have an excellent detectability of the microorganism due to color change of the pH indicator. The amounts of the components constituting the above-mentioned media may be either increased or decreased by a person skilled in the art and it is also possible to add appropriate component(s) provided that the basic characteristics are unaltered. Commercially-available ones may be used as the components to be compounded with the medium. For example, salt-polymyxin broth is available from NISSUI SEIYAKU K.K., Japan, lauryl sulfate broth is available from DIFCO and other components are available from DIFCO, WAKO PURE CHEMICAL INDUSTRIES, LTD., etc.

The apparatus of the present invention for the detection of microorganisms is useful for detecting specific kinds of microorganisms (food poisoning microorganisms such as *Staphylococcus aureus,* Salmonella, *Escherichia coli, Vibrio parahaemolyticus* and other intestinal microorganisms) in cooking environments (such as equipment and utensil at cuisine) and human living environments including kitchen, toilet, bath room and shops where food and beverage are sold. It is also possible to utilize the microorganism-detecting apparatus of the present invention with an object of detecting the afore-described microorganisms in food and food materials containing various components in high concentrations such as for detecting the contamination by food poisoning microorganisms. Food and food materials contain various components such as saccharides, proteins, lipids, organic acids (e.g., acetic acid and citric acid), amino acids, chemical condiments, vitamins, minerals and other chemical substances. As a result thereof, pH, ion strength, etc. of the medium change and, when detection is conducted where the principle of the detection utilizes the color change of the pH indicator for the pH change of the medium due to proliferation of microorganisms, there is a possibility that the above changes in pH and ion strength affect on the pH indicator used there. In that case, it is possible to prepare an appropriate sample depending upon the type of the food and food materials to be tested by, for example, subjecting the sample to a pretreatment (such as adjustment of pH), selecting an appropriate pH indicator, changing the components of the medium or changing the amounts of the components. For example, when the food to be tested is a beverage such as a milk product and an object is to detect *Escherichia coli*, Bromthymol Blue used as a pH indicator may be substituted with Bromcresol Purple.

Aseptic Condition

The microorganism-detecting apparatus of the present invention as mentioned above is preferably in an aseptic condition (at least in its inner area) immediately before the use in view of correctness of the test. In making the apparatus of the present invention aseptic after its manufacture, known physical measures (e.g., sterilization by irradiation of electromagnetic waves such as ultraviolet ray and gamma-ray) and/or chemical measures (e.g., sterilization by gas such as ethylene oxide) may be used without particular limitation. For example, the apparatus can be sterilized by irradiating with gamma-ray at 1 to 30° C. for one minute. When sterilization is conducted by a sterilizer using ethylene oxide, sterilization can be achieved by conducting at, for example, 0 to 70° C. (preferably, at 30 to 50° C.) in a gas consisting of about 10 to 40%; of ethylene oxide and about 60 to 90% of carbon dioxide gas (preferably, about 20% of ethylene oxide and about 80% of carbon dioxide gas) under certain pressure (preferably, at the pressure of about 0.1 to 1 kgw/m$^2$ or, more preferably, at about 0.3 kgw/m$^2$) for about 1 to 48 hours (preferably, about 3 to 10 hours).

After the above-mentioned sterilization, it is preferred that the microorganism-detecting apparatus of the present invention is stored in a bag which is made of film or the like (not shown). At that time, the microorganism-detecting apparatus (FIG. 1) may be unitedly stored in the same bag or, if necessary, each of the container and the cover (2) (and the microorganism-collecting part (6)) may be stored in different enclosures.

With regard to selection and combination of the aforedescribed microorganism-collecting end, various receiving forms concerning the antibiotic substances and various forms concerning the medium, a lot of variations and combinations are allowable provided that they are not out of the objects and characteristic features of the present invention. Especially in the case where both (or at least one of) antibiotic substance and medium (particularly preferably, liquid medium) are/is received in a bag, ampule or capsule made of synthetic resin or glass and, upon actual use, the receiver is broken whereby the antibiotic substance and the medium are unitedly combined, it is preferred that the area of the container receiving the bag, ampule or capsule is made of a material or in a shape whereby such bag, ampule or capsule can be easily broken or destroyed by a breaking device or by a force from outside without such a device. For example, the area is flexible or is a substance having elasticity or flexibility.

Disinfectant/Bactericide

The disinfectant or bactericide which is used for disinfecting and/or sterilizing the incubated pathogenic microorganism in the microorganism-detecting apparatus after use, whereby the used microorganism-detecting apparatus can be safely disposed is added in such a state that it is substantially separated from the outside or from the environment once the incubation of the microorganism to be tested is started so that the area containing the incubated microorganism can be disinfected and/or sterilized. If it is in such a structure, it may be located in the microorganism--detecting apparatus of the present invention in any form but a representative example is that disinfectant/bactericide is present in a form that it is received in the second bag-shaped member (8) which is different from the first bag-shaped member for receiving the medium (3) in a cover (2). With regard to the disinfectant/bactericide, one which is suitably selected from disinfectants and/or bactericides which have been known in the art may be used and the examples are disinfectants/ bactericides of a chlorate type, those of an invert soap type, those of a biguanide type, those of an aldehyde type and those of a phenol or cresol type. Representative examples of the disinfectant/ bactericide are sodium hypochlorite, bleaching powder, chloramine-T, benzalkonium chloride, benzethonium chloride, chlorhexidine salt, polyalkylene biguanidine salt, formaline, glutaraldehyde and pompidon iodine.

The disinfectant (bactericide) used may be selected from those which have been commonly used for disinfecting, sterilizing or washing the area wherefrom pathogenic microorganisms such as food poisoning microorganisms were detected, such as a chopping board, and cooking board or which have been found to be preferred for such an object. Examples of such a detergent (disinfectant) are the abovementioned sodium hypochlorite (WAKO PURE CHEMICAL INDUSTRIES, LTD., Japan), "Tego-51" (10% ; trade name of NIPPON SHOJI K.K., Japan), "Kitchen Kabi-Killer" (trade name of JOHNSON K.K., Japan) and "Kitchen Haiter" (trade name of KAO K.K., Japan).

Such a detergent (disinfectant) may also be that where its disinfecting effect has been well noted by the following test method using, for example, *Staphylococcus aureus* ATCC 25923, *Escherichia coli* ATCC 25922, *Enterobacter faecalis* ATCC 29212 and *Pseudomonas aeruginosa* ATCC 27853.

Method for Testing the Disinfecting (Sterilizing) Effect (1) Preparation of Microorganism Solution Standard strains of *Staphylococcus aureus* ATCC 25923, *Escherichia coli* ATCC 25922, *Enterobacter faecalis* ATCC 29212 and *Pseudomonas aeruginosa* ATCC 27853 incubated for 24 hours were used and prepared into a solution having a McFarland's standard turbidity of No.1 ($3.0 \times 10^8$ CFU/ml) using a sterile physiological saline solution.

(2) Sterilizing Method

Each of the washings was used as an original solution and contacted, in a final concentration of 10%, for five minutes with the microorganism solution prepared in the above (1).

(3) Incubating (Culturing) Method

The microorganism solution contacted with the washing for five minutes as mentioned in the above (2) was used as an original solution, diluted to 10-fold (×10) and 100-fold (×100) with a sterile physiological saline solution and each 0.1 ml of it was inoculated to a blood-agar medium followed by incubating. As a control, a system containing no detergent was prepared and incubated by the same manner as above. Numbers of the colonies grown after incubating at 37° C. for 48 hours were compared with those of the control whereby the disinfecting effect was evaluated.

When sodium hypochlorite (WAKO PURE CHEMICAL INDUSTRIES, LTD., Japan), "Tego-51" (10% ; trade name of NIPPON SHOJI K.K., Japan), "Kitchin Kabi-Killer" (trade name of JOHNSON K.K., Japan) and "Kitchen Haiter" (trade name of KAO K.K., Japan) were used as detergents, all of the standard strains were found to be sterilized within five minutes by those detergents.

Figure 4:
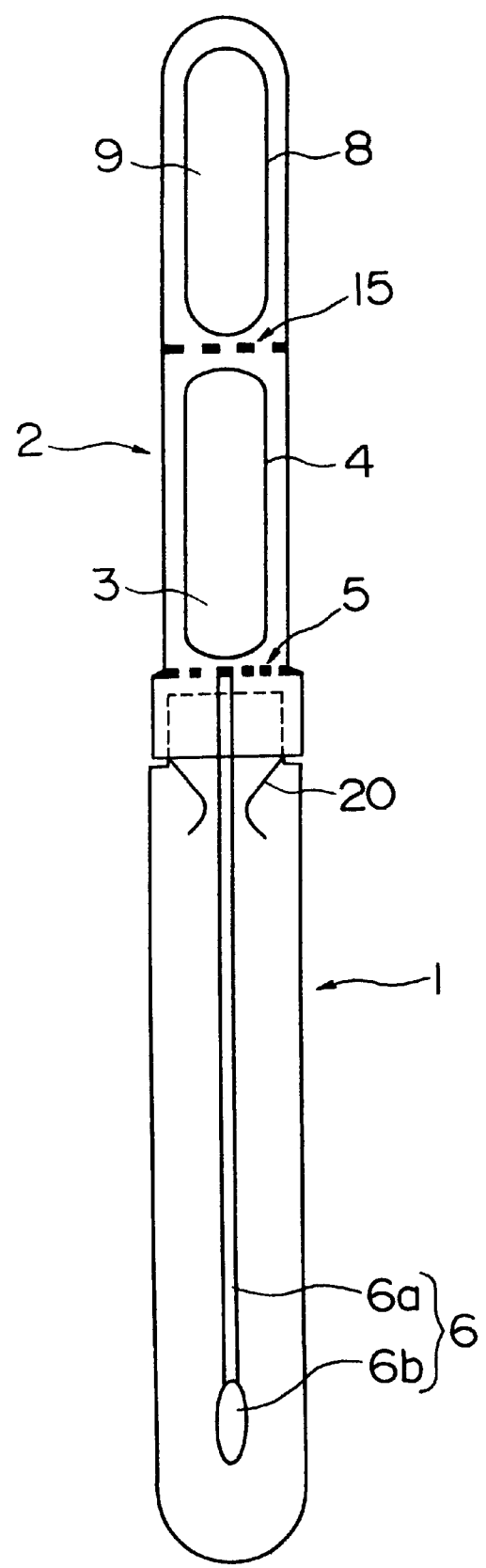
FIG. 4 is a schematic side cross sectional view showing another embodiment of the microorganism-detecting apparatus of the present invention.

FIG. 4 shows another embodiment of the microorganism-detecting apparatus of the present invention. In this embodiment of FIG. 4, a "guide member" (20) has a function of promoting the falling-down of a medium (3) along the rod-shaped element (6a) when the medium (3) falls down into a container (1), and the guide member is disposed at the lower area of the partition member (5). Constitution of FIG. 4 is the same as that of FIG. 1 except that the guide member (20) is installed therein.

There is no particular limitation for the material shape, size, etc. of the guide member (20) so long as the guide member (20) plays a function of promoting the falling-down of the medium (3) along the rod-shaped element (6a). In view of the easiness in promoting the falling-down of the medium (3) along the rod-shaped element (6a), it is preferred that the guide member (20), at least a part thereof, has a smaller inner diameter than that of the container (1).

To be more specific, it is preferred that, as shown in FIG. 4, the guide member (20) is composed of a "fan"-shaped member where the lower end of the guide member is somewhat inclined to the central direction of the container (1) (i.e., in other words, the lower end has a smaller diameter than the inner diameter of the container (1)) although such an "inclination" may be omitted. FIG. 5 shows a microorganism-detecting apparatus of the present invention where the disk member (7) is placed in the container (1).

Figure 6:
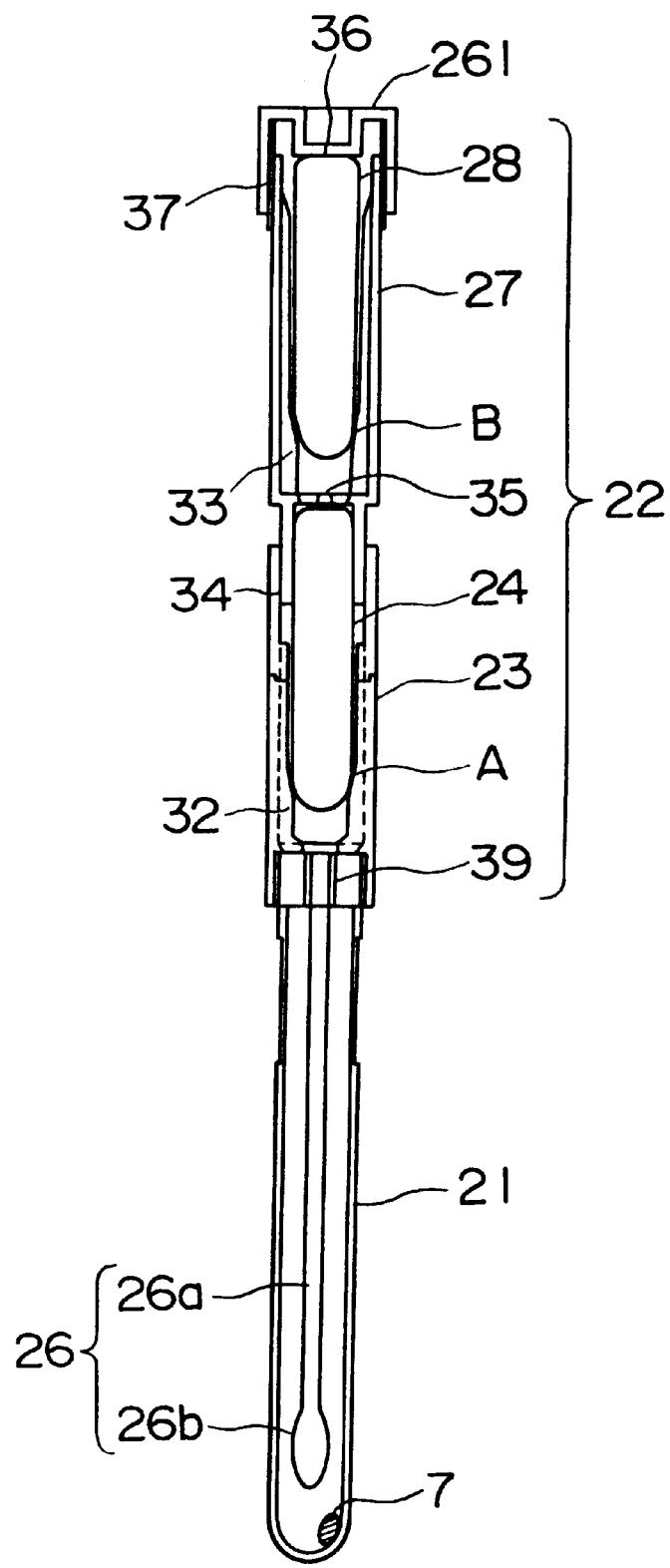
FIG. 6 shows another embodiment of the microorganism-detecting apparatus of the present invention where the cross-sectional shape of the apparatus is mainly illustrated.
Figure 7:
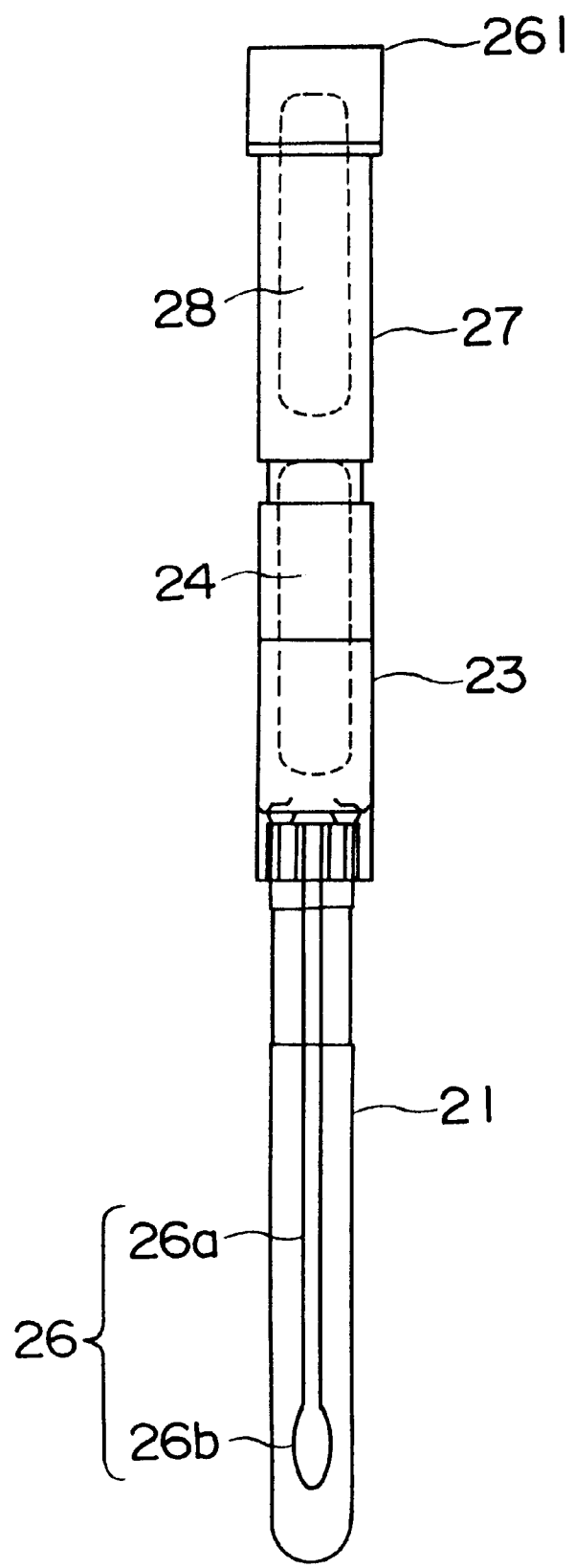
FIG. 7 mainly shows the outer shape of the apparatus of FIG. 6.
Figure 8:
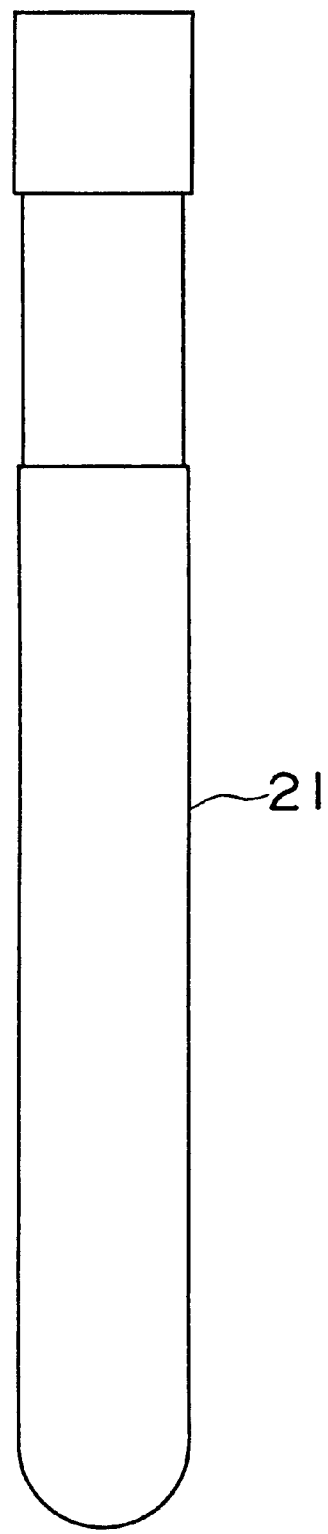
FIG. 8 shows the outer shape of the container part supplying a space for incubation of a microorganism in the apparatus of FIG. 6.
Figure 9:
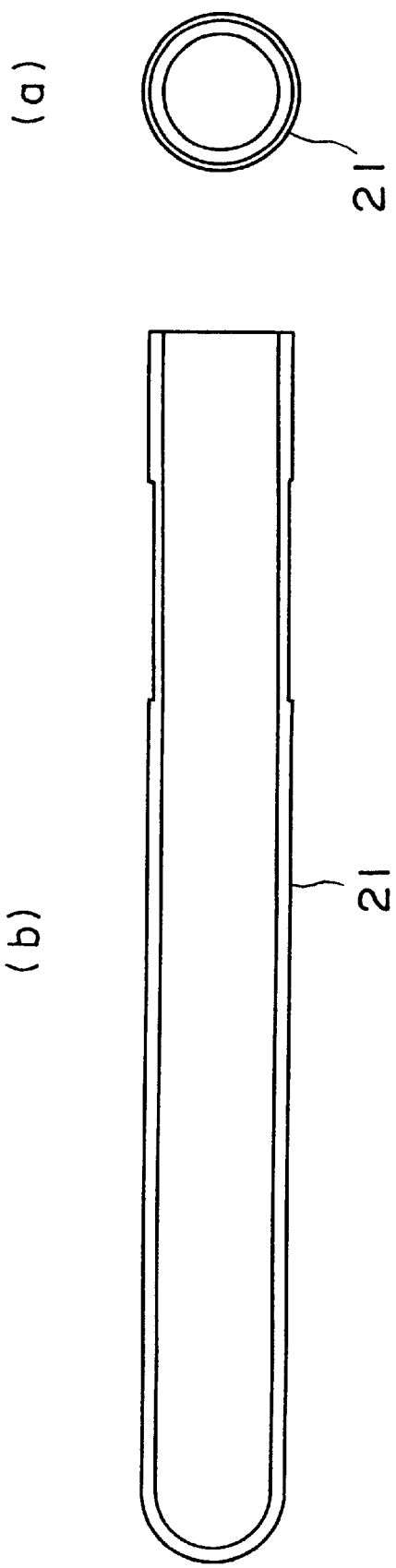
FIGS. 9a and 9b show the cross-sectional structure of the container part supplying the space for incubation of a microorganism in the apparatus of FIG. 6 wherein 9(a) is a shape from its top while 9(b) is a shape from its side.
Figure 10:
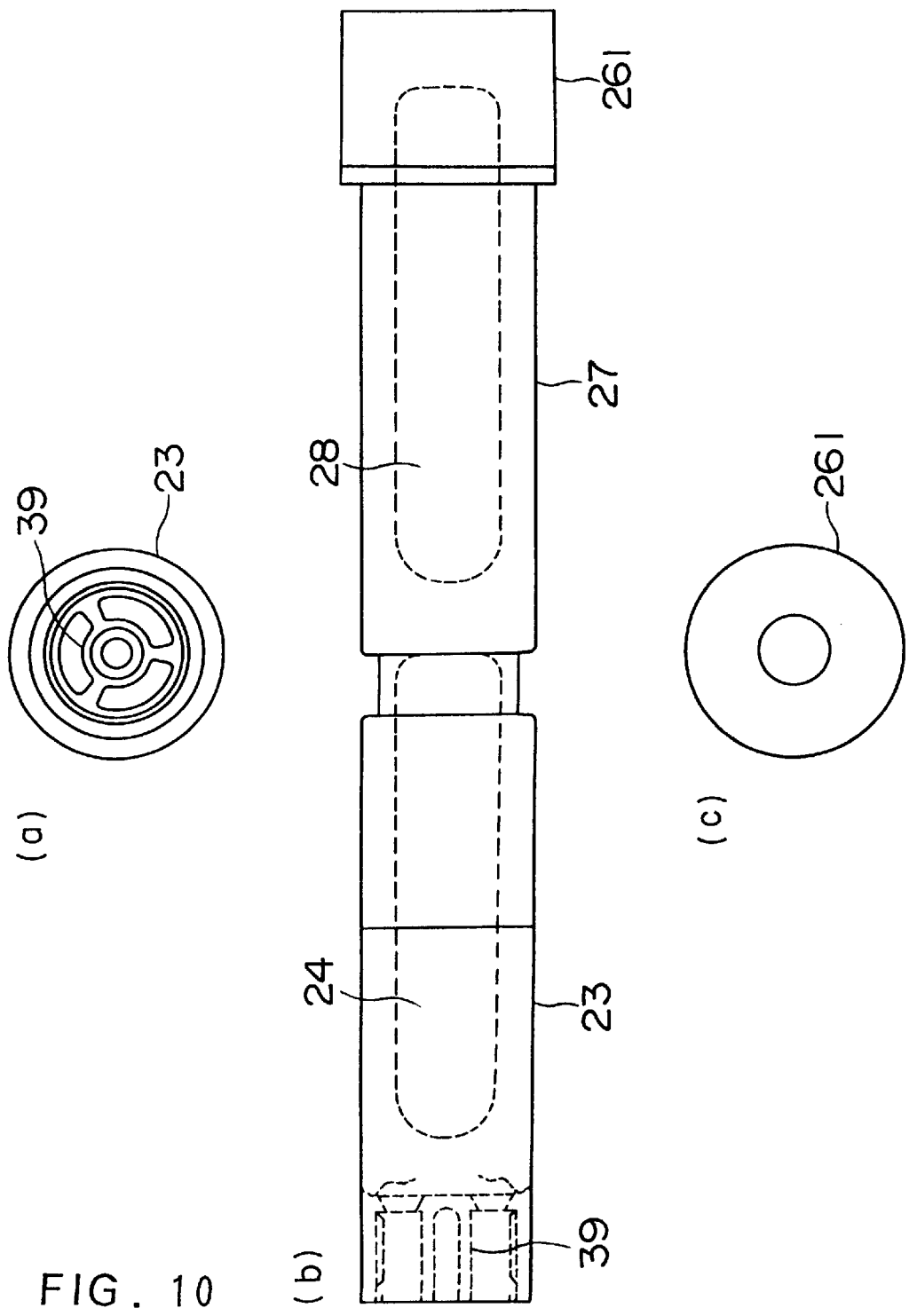
FIGS. 10a, 10b and 10c show an outer shape of the cover part of the apparatus of FIG. 6 wherein 10(a) is a shape from its bottom, 10(b) is a shape from its side, and 10(c) is a shape from its top.
Figure 11:
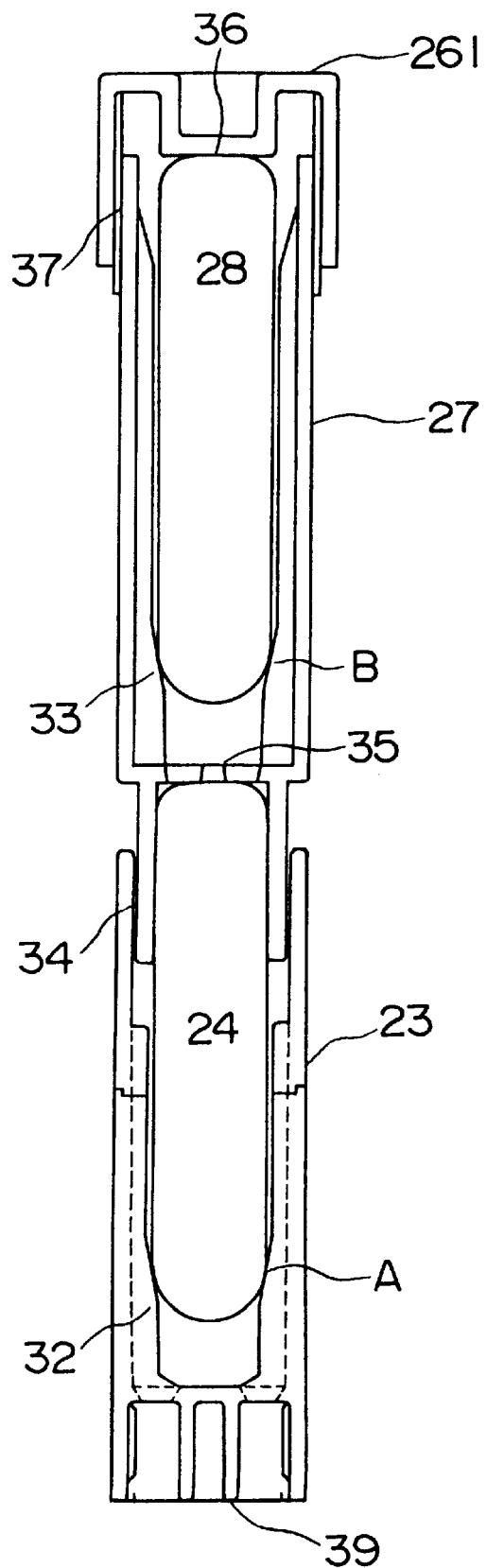
FIG. 11 shows a cross-sectional structure of the cover part of the apparatus of FIG. 6.

FIGS. 6 to 11 show a basic constitution of the microorganism-detecting apparatus of the present invention in another representative embodiment, particularly to show a constitution basically bestowed with structure for disinfecting and/or sterilizing the cultured medium, etc. afer incubation. FIG. 6 mainly sows a cross sectional view of the microorganism-detecting apparatus; FIG. 7 mainly shows an outer appearance of the microorganism-detecting apparatus; FIG. 8 shows an outer appearance of the container (21) for the microorganism-detecting apparatus; FIG. 9a shows a view from the upper side of the container (21) for the microorganism-detecting apparatus; FIG. 9b shows a cross sectional view of the side of the container (21) for the microorganism-detecting apparatus; FIG. 10a is a shape of the cover (22) for the microorganism-detecting apparatus and is the shape observed from the connected side with the container (21); FIG. 10b mainly shows an outer appearance from one side of the cover (22) for the microorganism-detecting apparatus; FIG. 10c is a shape of the cover (22) for the microorganism-detecting apparatus and shows the view from the upper part (from the side of the cap (261)); and FIG. 11 shows the cross section view from the side of the container for the microorganism-detecting apparatus (the microorganism collecting part (member) is omitted in FIG. 10 and FIG. 11).

In FIG. 6, the cover (22) is mainly composed of (i) a cover-constituting member (housing) (23) capable of receiving an ampule (24) in which a medium is contained, (ii) a cover-constituting member (housing) (27) capable of receiving an ampule (28) in which a disinfectant is contained, and (iii) a cap member (261). A protrusion (or projection) (32) is disposed at the bottom side of the cover-constituting member (23), i.e. at the connecting side with cylindrical container (21). The protrusion (32) may be placed throughout the circumference of the cover-constituting member (23) whereby the connecting side portion of the cover-constituting member (23) with the container (21) becomes thick. Alternatively, the protrusion (32) may be sporadically placed in a projecting manner on the inner side of the cover-constituting member (23) such as a projection of a crosspiece (sash bar) or the like. In a preferred embodiment, a screw cutting is done at the top of the cover-constituting member (23), i.e. at the end (34) at the side of the cap-material (261) as to engage with the screw threads made on the cover-constituting member (27) and, when the main body of the cover-constituting member (27) is rotated, a bottom (35) of the area where the ampule (28) in the cover-constituting member (27) is received can be pushed against the side of the container (21). Alternatively, the top of the cover-constituting member (23), i.e. an end (34) at the side of the cap member (261), is tightly engaged with an end of the cover-constituting member (27) at the side of the container (21) and, when the cover-constituting member (27) is pushed by sliding to the side of the container (21), the bottom (35) of the ampule (28)-receiving area of the cover-constituting member (27) can be easily pushed against the side of the container (21) whereby the ampule (24) can be pushed against the side of the container (21).

In the cover-constituting member (27), there are through holes at the bottom (35) of the receiving part for ampules (28) so that the disinfectant in the ampule flows down into the container (21) when the ampule (28) is broken. Like in the cover-constituting member (23), there are protrusions (or projections) (33) at the bottom side of the cover-constituting member (27), i.e. at the side of the ampule (24). Like in the afore-mentioned protrusions (32), the protrusions (33) may be placed throughout the circumference of the cover-constituting member (27) whereby the bottom (35) of the ampule-receiving part of the cover-constituting member (27) becomes thick at the side of the ampule (24). Alternatively, the protrusions (33) may be sporadically placed in a projecting manner on the inner side of the cover-constituting member (27). In a preferred embodiment, a screw cutting is done at the top of the cover-constituting member (27), i.e. at the end (37) at the side of the cap-material (261) so as to engage with the screw threads made on the cover-constituting member (261) and, when the head of the cap member (261) is rotated, a bottom (36) of the cap member (261) can be pushed against the side of the ampule (28). Alternatively, the top of the cover-constituting member (27), i.e. an end (37) at the side of the cap member (261), is tightly engaged with the cap member (261) and, when the cap member (261) is pushed into by sliding to the side of the container (21), the bottom (36) of the ampule (28)-receiving area of the cover-constituting member (261) can be easily pushed against the side of the container (21) whereby the ampule (28) can be pushed against the side of the container (21).

First, when the main part of the cover-constituting member (27) is rotated (or pushed against the container side) and the bottom (35) of the receiving area for the ampule (28) in the cover-constituting member (27) is pushed against the side of the container (21), the bottom (35) pushes down the ampule (24). Such a pushed-down ampule (24) is then supported with the slope of the protrusion (32) disposed on the cover-constituting member (23). As such, when the cover-constituting member (27) is pushed down to the side of the container (21), a tension would occur at a contacting point (A) of the ampule (24) with the slope of the protrusion (32) whereby the lower part of the ampule (24) is broken and the contents therein is allowed to be released. The contents coming out from the ampule (24) flows down into a container (21) due to gravity and contacts with the microorganism-collecting end (26b). (Incidentally, in FIG. 6, through holes, attaching area of the microorganism-collecting part, fine structure of joint portions between the cover and the container, etc. are omitted.)

During the disinfection after incubation of the microorganism, when the top of the cap member (261) is rotated (or pushed against the side of the container) and the bottom (36) of the cap member (261) is pushed against the side of the ampule (28), the bottom (36) of the cap member (261) pushes down the ampule (28). The pushed-down ampule (28) is then supported on the slope of the protrusion (33) placed at the cover-constituting member (27). As such, when the cap member (261) is pushed against the side of the container (21), a tension would occur at a contacting point (B) of the ampule (28) with the slope of the protrusion (33) whereby the lower part of the ampule (28) is broken and the contents therein is allowed to be released. The contents coming out from the ampule (28) flows down into a container (21) through the perforations placed at the bottom (35) of the ampule (28)-receiving part of the cover-constituting member (27) due to gravity and contacts the incubated microorganism. It is preferred in view of the actual use that the ampule is made of a fragile material such as glass or hard plastic and that, when a mechanical force is applied thereto (particularly when the mechanical force is partly applied), the ampule is easily broken.

The medium containing the incubated pathogenic microorganism and the space in the container where there is a high possibility of contamination with the microorganism are disinfected and/or sterilized by a disinfectant. As such, the apparatus can be made into a safely disposable state. It is possible for the incubation system of the apparatus of the present invention that, since the beginning of incubation by supplying the medium into an apparatus (1), certain microorganisms (targets) are found/detected by observing the incubated medium and at last the apparatus is disinfected and/or sterilized to make it disposable while the incubation system is kept in a substantially tightly closed state relative to the outside or to the environment throughout the above steps. The microorganism-detecting apparatus of the present invention is useful with a view that even if the target microorganism to be tested is not limited to pathogenic but ordinary (nonpathogenic), pollution of environment (or possibility thereof) is to be avoided. Further, the microorganism-detecting apparatus has excellent portability and, therefore, the fact that the apparatus can be disinfected/sterilized to such an extent that it can be safely and surely disposed is valuable and appreciated. In addition, it is clear from the structure of the apparatus of the present invention that the microorganism-detecting apparatus can be surely, easily and securely operated even by unskillful persons.

Figure 12:
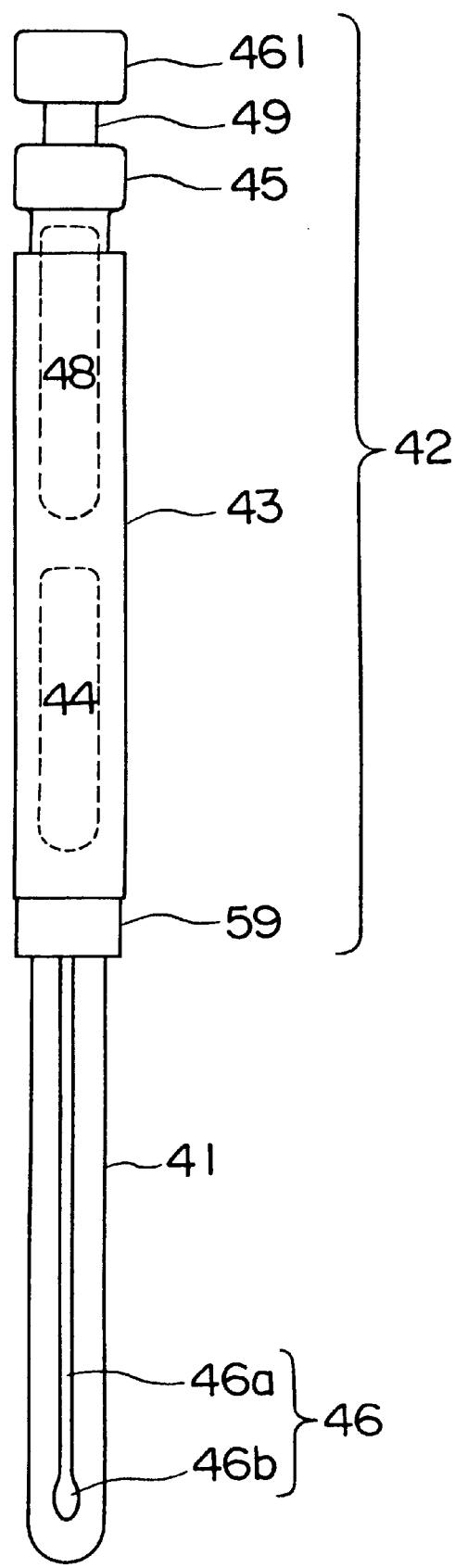
FIG. 12 shows another embodiment of the microorganism-detecting of the present invention where the outer shape is illustrated.
Figure 13:
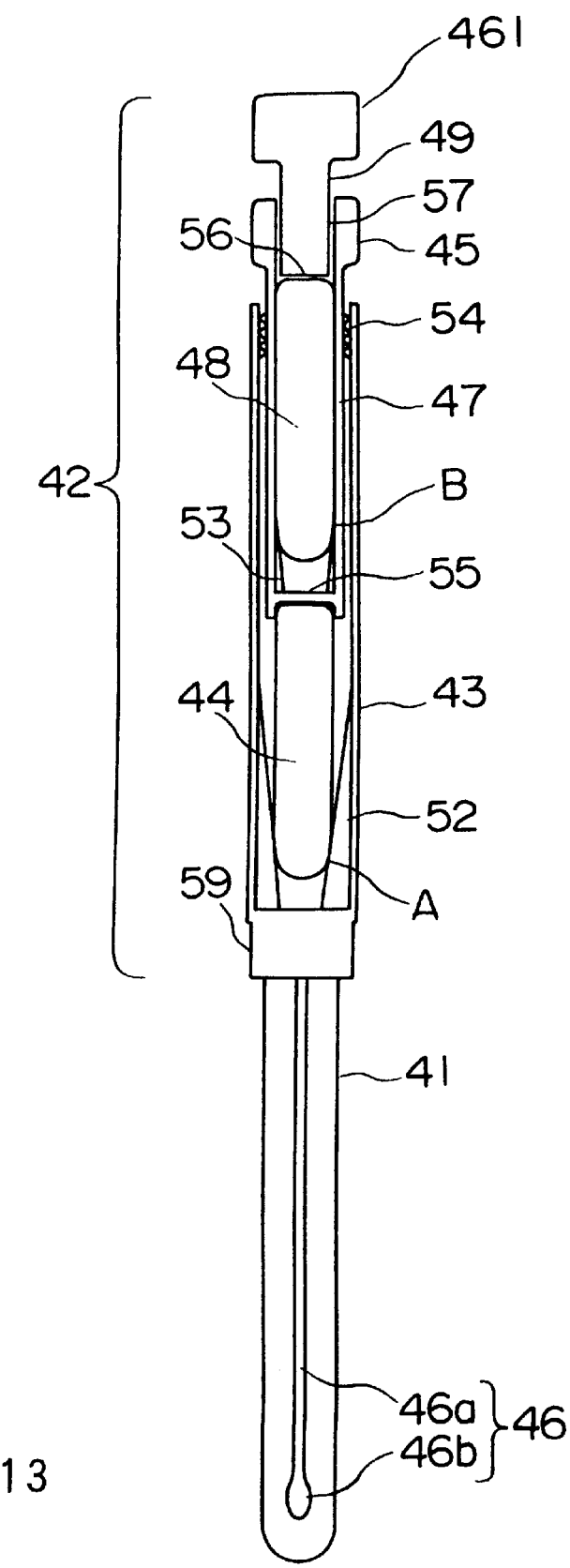
FIG. 13 shows another embodiment of the microorganism-detecting apparatus of the present invention where the cross-sectional shape of the apparatus of FIG. 12 is illustrated.

FIG. 12 and FIG. 13 show a constitution which is fundamentally present in another representative embodiment of the microorganism-detecting apparatus of the present invention, particularly with structure for disinfecting/sterilizing the cultured medium, etc. after incubation.

In FIG. 13, a cover (42) is mainly composed of (i) a cover-constituting member (43) capable of receiving an ampule (44) containing a medium, (ii) a cover-constituting member (47) capable of receiving an ampule (48) containing a disinfectant, and (iii) a cap member (49). At the bottom side of the cover-constituting member (43), i.e. at the side of the junction (59) with the cylindrical container (41), there is a protruding portion (or projection) (52). The protrusion (52) may be placed throughout the circumference of the cover-constituting member (43) whereby the cover-constituting member (43) becomes thick at the engaging side (59) thereof with the container (41), or the protrusion (52) may be sporadically placed in a projecting manner on the inner side of the cover-constituting member (43), such as a protrusion of a crosspiece or the like. In a preferred embodiment, a screw cutting is done at the top of the cover-constituting member (43), i.e. at the end (54) at the side of the cap member (49) so as to engage with the screw threads made on the cover-constituting member (47) and, when a head part (45) of the cover-constituting member (47) is rotated, a bottom (55) of the cover-constituting member (47) can be pushed against the side of the container (41). The bottom part (55) of the cover-constituting member (47) has one or more through holes whereby, when an ampule (48) is broken, the disinfectant contained therein can flow into a container (41) as mentioned below (incidentally, in FIG. 13, the through hole is not shown).

A protruding portion (or projection) (53) is disposed at the bottom side of the cover-constituting member (47), i.e. at the side of an ampule (44), like the cover-constituting member (43). The protrusion (53) may be disposed, like the above protrusion (52), throughout the circumference of the cover-constituting member (47) whereby the cover-constituting member (47) becomes thick at the bottom side (55) of the ampule side (44). Alternatively, the protrusion (53) may be sporadically placed in a projecting manner on the inner side of the cover-constituting member (47). In a preferred embodiment, a screw cutting is done at the top of the cover-constituting member (47), i.e. at the end (57) at the side of the cap member (49) so as to engage with the screw threads made on the cap member (49) and, when a head part of the cap member (49) is rotated, a bottom (56) of the cap member (49) can be pushed against the side of the ampule (48).

First, when a head part (45) of the cover-constituting member (47) is rotated so that the cover-constituting member (47) is pushed against the side of the container (41), a bottom (55) of the cover-constituting member (47) pushes down the ampule (44). The pushed-down ampule (44) is then supported by a slope of the protrusion (or projection) (52) disposed in the cover-constituting member (43). As the cover-constituting member (47) is pushed further against the side of the container (41), a tension becomes higher at the contacting portion (A) between the ampule (44) and a slope of the protrusion (52) whereupon the lower area of the ampule (44) is broken and the content therein is allowed to release. The contents coming out from the ampule (44) flows down into the container (41) because of the force of gravity and comes in contact with the microorganism-collecting end (46b). (Incidentally, in FIG. 13, a through hole at (59), a connecting area for the microorganism-collecting member, the detailed structure of the engagement between the cover and the container, etc. are omitted.)

At the disinfecting stage after incubation, when the bottom (56) of the cap member (49) is pushed against the side of the ampule (48) by rotating the top portion (461) of the cap member (49), a bottom (56) of the cap member (49) pushes down the ampule (48). The pushed-down ampule (48) is then supported by a slope of the protrusion (53) disposed in the cover-constituting member (47). As the cap member (49) is pushed further against the container (41) side, a tension would occur higher at the contacting area (B) of the ampule (48) with the slope of the protrusion (53) whereupon the lower part of the ampule (48) is broken and the contents therein is allowed to release. The contents coming out from the ampule (48) flows down by gravity into a container (41) through a perforated hole (through hole) (not shown) formed in the bottom (55) of the cover-constituting member (47) and comes in contact with the incubated microorganism. It is preferred in terms of actual use that the ampule is made of fragile material including glass, hard plastic material, etc. whereby it can be easily broken upon application (especially, partial application) of mechanical force.

The medium containing the incubated pathogenic microorganisms, etc. and the space of the container having a high possibility of contamination with the microorganisms are disinfected and/or sterilized by a disinfectant. As such, the apparatus can be made safely disposable. It is possible for the incubation system of the apparatus of the present invention that, since the beginning of incubation by supplying the medium into an apparatus (1), a certain microorganism is found/detected by observing the incubated (cultured) medium and, at last, the apparatus is disinfected/sterilized to make it disposable while the incubation system is kept in a substantially tightly closed state relative to the outside (surrounding atmosphere) or to the environment throughout the above steps. The microorganism-detecting apparatus of the present invention is useful and characteristic with a view that the microorganisms to be tested are not limited to pathogenic ones, and pollution of the environment (or possibility thereof) is to be avoided even if the microorganisms to be tested are ordinary ones. Further, the microorganism-detecting apparatus has an excellent portability and an unique arrangement and, therefore, the fact that the apparatus can be disinfected/sterilized to such an extent that it can be safely and surely disposed is valuable and highly appreciated. In addition, it is clear and apparent from the arrangement of the apparatus according to the present invention that the microorganism-detecting apparatus can be surely, securely and readily operated even by unskillful persons.

Figure 14:
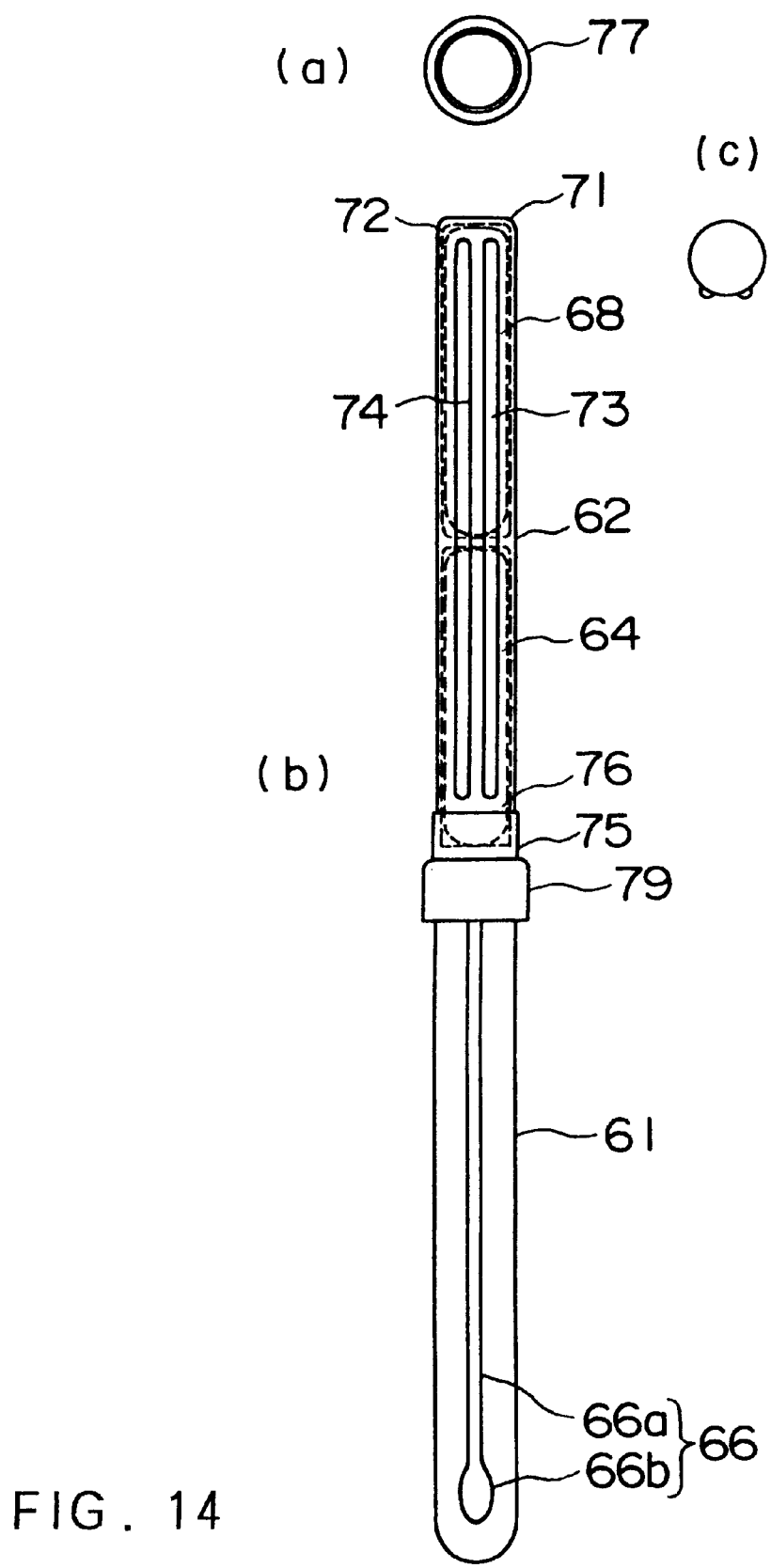
FIGS. 14a, 14b and 14c show another embodiment of the microorganism-detecting apparatus of the present invention where 14(a) is a ring (77), 14(b) is a view from the side of the microorganism-detecting apparatus consisting of container and cover, and 14(c) is a cross-sectional shape of the cover part equipped with (73) and (74)

FIG. 14 shows a constitution which is fundamentally present in one representative embodiment of the microorganism-detecting apparatus of the present invention, like those as shown in FIG. 12 and FIG. 13. It uniquely has structure for disinfecting and/or sterilizing the cultured medium, etc. after incubation.

In FIG. 14, the cover is mainly composed of a cover-constituting member (62) which is capable of receiving and holding (i) an ampule containing a medium and (ii) an ampule containing a disinfectant. At the side contacting with the surface of ampules (64/68), protrusions (or projections) (73 and 74) are installed in a form of grooves (or of ridges) on the inner side of the cover-constituting member (62). Refer, for example, to FIG. 14(c). When a ring (77) (cf. FIG. 14(a)) having a slightly smaller diameter than a diameter (or outer diameter) of the cover-constituting member (62) accommodating the ampule is prepared and passed from a top (71) of the cover-constituting member (62) to the side of a container (61), the ring (77) smoothly passes at the area of (72) in the cover since there is no projection there but, after the area (72), tension due to the protrusions (73 and 74) is applied to the ampule and forces the ampule to be broken from its side. When the protrusions (73 and 74) are made to come closer to the ampule upon coming nearer the container (61), then stronger tension bears on the ampule as the ring (77) passes from the top (71) of the cover (62) to the side of the container (61). Incidentally, in FIG. 14, a perforated hole (through hole) for the medium and the disinfectant each coming out from each ampule (64/68) into a container (61), an area where the microorganism-collecting part is attached, the detailed arrangement of engaging portion between the cover and the container, etc. are omitted.

In another embodiment, the cover is mainly composed of a cover-constituting member (62) capable of receiving and holding (i) an ampule (64) containing the medium and (ii) an ampule (68) containing the disinfectant as same as that mentioned hereinabove. Alternatively, it is also possible that a ring (77) is previously installed on the area (76) of the cover (62) at the container (61) side and the ring (77) is raised to the top (71) side of the cover (62) whereby breaking is started from the lower ampule (64) the same as above.

In still another embodiment, the cover is mainly composed of a cover-constituting member (62) capable of receiving and holding (i) an ampule (64) containing a disinfectant and (ii) an ampule (68) containing the medium. A ring (77) prepared already is passed to a container (61) from the top (71) of the cover (62) so that the ampule (68) is broken from its side. The ring (77) which was moved for breaking the ampule (68) as such is then moved to the middle portion of the cover (62) and either stopped there or moved upward followed by taking away from the top (71). For breaking another ampule (64), a ring (77) (hereinafter, referred to as (77')) (not shown) is previously installed on the area (76) of the cover (62) at the side of the container (61) and said ring (77') is raised to the top side (71) of the cover (62) whereby the ampule (64) is broken from the lower part. Alternatively, it is also possible that the cover is mainly composed of a cover-constituting member (62) capable of receiving and holding (i) an ampule (64) containing the medium and (ii) an ampule (68) containing the disinfectant and that the ring (77) and the ring (77') are moved in a reversed order as compared with the above, whereby the medium is first supplied to the container (61) and, after incubation, the disinfectant is supplied to the container (61).

Figure 15:
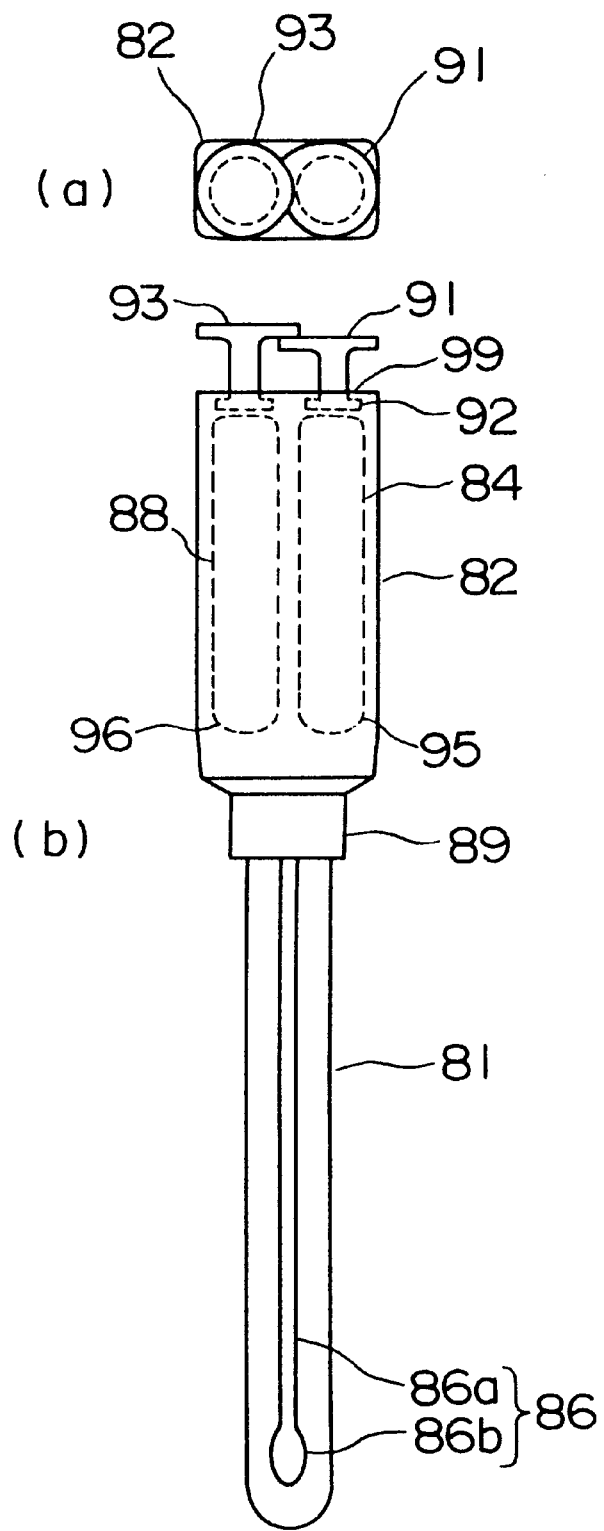
FIGS. 15a and 15b show another embodiment of the microorganism-detecting apparatus of the present invention where 15(a) is a shape from its top while 15(b) is a shape from its side.

FIG. 15 illustrates a fundamental arrangement required in a representative specific embodiment of the microorganism-detecting apparatus according to the present invention, particularly the fundamental arrangement for disinfecting and/or sterilizing the cultured medium, etc. after incubation.

In FIG. 15, the cover (82) is mainly composed of a cover-constituting member capable of receiving and storing (i) an ampule (84) containing a medium and (ii) an ampule (88) containing a disinfectant. In the cover-constituting member (82), there are pushing-down members (91 and 93) at the top (99) which is an opposite side to the container (81). The pushing-down members (91) is equipped with a part (92) having a shape for allowing a force to be applied to the top of the ampule (84) in a stable manner. Similarly, another pushing-down member (93) is equipped with a part (94) (in the drawing, this symbol is omitted) having a shape for allowing a force to be applied to the top of the ampule (88) in a stable manner.

First, when the pushing-down member (91) is pushed in, the ampule (84) is pushed down via the part (92). Then tension would occur at a contacting point (95) of the ampule (84) with a slope (or crosspiece-like projection) (not shown) formed at the side near the container (81) and on the inner side (ampule-receiving side) of the cover (82). The tension forces the lower part of the ampule to be broken whereby the medium is taken out from the ampule and comes into the container (81) by gravity through one or more perforated holes (through hole) (not shown) in the engaging portion (89). When another pushing-down member (93) is pushed in after incubation of the microorganism, the ampule (88) is pushed down via the part (94) whereupon a tension would occur at a contacting point (96) of the ampule (88) with a slope (or crosspiece-like projection) (not shown) located at the side near the container (81) and on the inner side (ampule-receiving and storing side) of the cover (82) and forces the lower part of the ampule to be broken whereby the disinfectant is released from the ampule and comes into the container (81) through the through hole (perforated hole) (not shown) of the engaging portion (89) by gravity.

The pushing-down members (91/93) may be installed at the top (99) of the cover (82) in such a manner that they can be pushed in by a force from outside which is more than a certain degree. The pushing-down members (91/93) may also be engaged with the top member (99) by screw threads and, in that case, the members (91/93) are in such a constitution that they can be pushed against the side of the container (81) by rotating them.

In any event, the constitution is to be in such a manner that, until there is a need of taking out the medium and the disinfectant in use of the microorganism-detecting apparatus according to the present invention, the bag-shaped members such as ampules are sustained freely from being broken and releasing their contents but, once necessary, each of the contents can be freely or optionally released therefrom.

Figure 16:
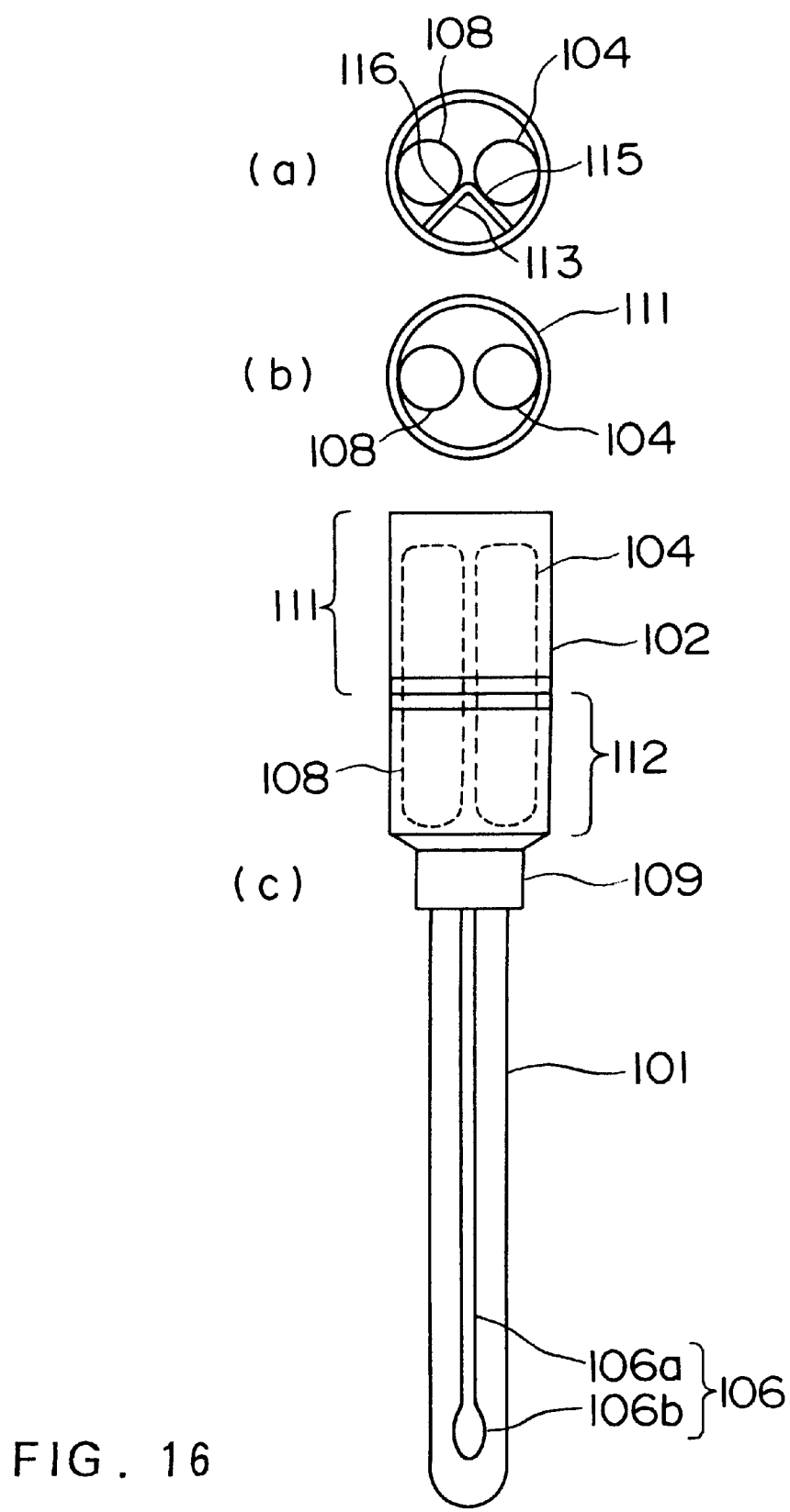
FIGS. 16a, 16b and 16c show another embodiment of the microorganism-detecting apparatus of the present invention where 16(a) is a cross-sectional shape of the part corresponding to the cover-constituting member (112), 16(b) is a cross-sectional shape of the part corresponding to the cover-constituting member (102) and 16(c) is a shape from the side of the microorganism-detecting apparatus.

FIG. 16 illustrates a fundamental arrangement required in a representative specific embodiment of the microorganism-detecting apparatus according to the present invention, particularly the fundamental arrangement for disinfecting and/or sterilizing the cultured medium, etc. after incubation.

In FIG. 16, a cylindrical cover (102) is mainly composed of (i) a cover-constituting member (112) which constitutes an almost lower half of the cover (102) and (ii) another cover-constituting member (111) which constitutes an almost upper half of the cover (102). At least one of the cover-constituting members (112 and 111) is made in such a manner that it can rotate against another by applying a force thereto along the circumference of the cover (102). In the cover (102), both an ampule (104) containing a medium and another ampule (108) containing a disinfectant are received and held. The inner side of the cover-constituting member (112) is equipped with a protrusion (113) which contacts the ampules (104 and 108). The cover-constituting member (111) is equipped with holes (124 and 128) (the symbols are omitted in the drawing) which can receive the respective ampules (104 and 108). A cover (102) is constituted in such a manner that the cover-constituting member (111) is located on the cover-constituting member (112) (i.e., at the opposite side of the container (101)) and an ampule (104) is placed in a hole (124) in the cover-constituting member (111) while another ampule (108) is placed in another hole (128). In the cover-constituting member (112), the ampules (104 and 108) placed as such are located so as to encounter to the protrusion (113) as in (a) of FIG. 16.

When, for example, the upper cover-constituting member (111) is rotated to an extent of 90 degrees in an anticlockwise direction, a tension would occur at the contacting part (115) of the ampule with the protrusion (113) whereupon the ampule (104) is broken and the medium contained therein flows out. The medium coming out as such comes into a container (101) through one or more perforated holes (not shown) at the engaging portion of the cover (102) with the container (101) by gravity and contacts with the microorganism-collecting end (106b). When the above cover-constituting member (111) is further rotated in an anticlockwise direction (totally rotated to an extent of 180 degrees), a tension would occur at the contacting part of the ampule (108) (not shown) with the protrusion (113) whereby the ampule (108) is broken and the disinfectant contained therein flows out. The disinfectant discharged as such comes into the container (101) by gravity through the perforated hole (not shown) at the engaging portion (joint) of the cover (102) with the container (101) and disinfects/sterilizes the apparatus including the incubated microorganism. Alternatively, when the above cover-constituting member (111) is rotated in a clockwise direction instead of rotating it to an extent of 180 degrees in an anticlockwise direction as mentioned above, a tension would occur at a contacting part (116) of the ampule (108) with the protrusion (113) where by the ampule (108) is broken and the disinfectant contained therein flows out.

The microorganism-detecting apparatus of the present invention can be made (i) in such a structure that a mechanism for breaking the bag-shaped member such as an ampule does not work by being equipped with a pawl or the like so that the bag-shaped member such as the ampule is sustained freely from breakage and the contents in the ampule is not released until there is a need of releasing the medium or the disinfectant or (ii) in such a structure that an arrangement is made wherein, unless a certain force is applied, rotation or pushing is not possible so that the mechanism for breaking the bag-shaped member such as the ampule does not work. The microorganism-detecting apparatus of the present invention may also be in such a manner that a protector such as a cap is applied to the mechanism for breaking the bag-shaped member so that the content therein is not released by breakage of the bag-shaped member such as the ampule until there is a need of releasing the medium or the disinfectant.

FIGS. 17 to 33 illustrate other representative specific examples of the microorganism-detecting apparatus of the present invention for their fundamental constitution, particularly the fundamental constitution as a structure for disinfecting and/or sterilizing the cultured medium, etc. after incubation.

Figure 17:
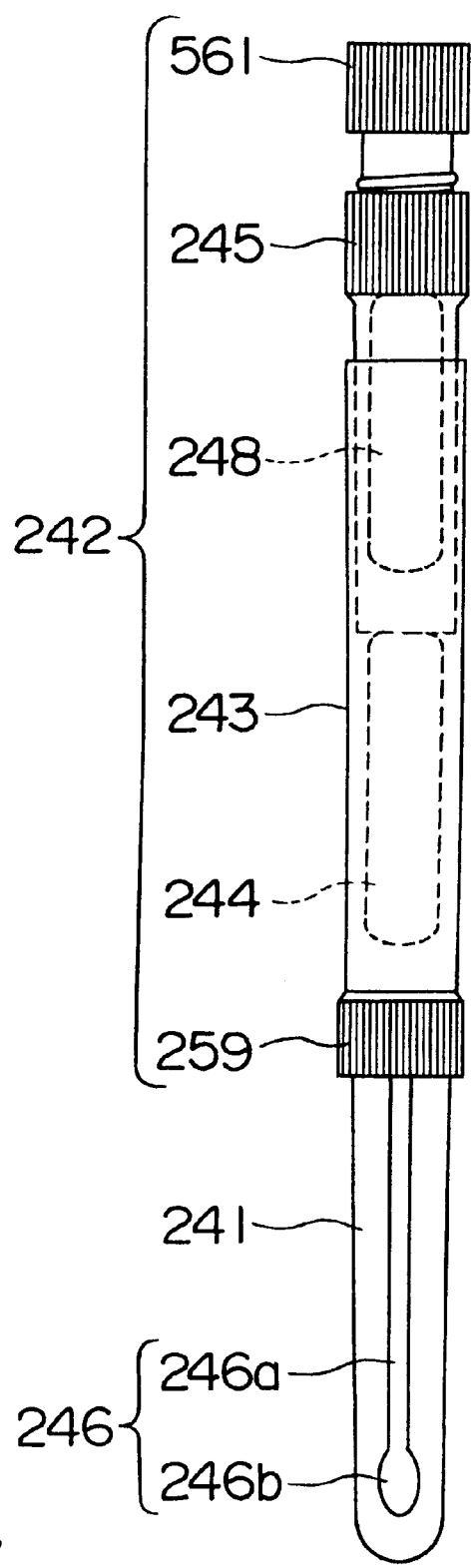
FIG. 17 shows another embodiment of the microorganism-detecting apparatus of the present invention where the outer shape is illustrated.
Figure 18:
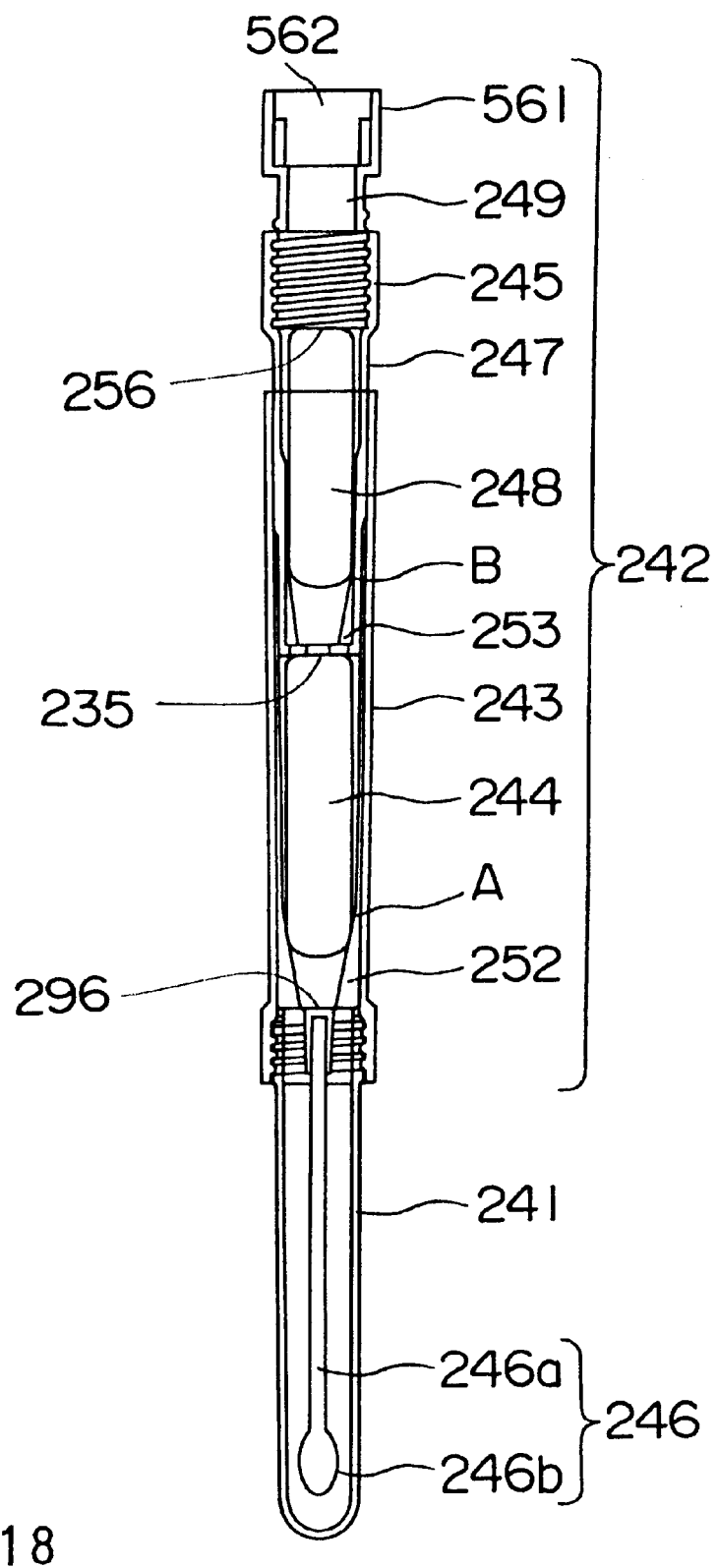
FIG. 18 shows a cross-sectional shape of the apparatus of FIG. 17.

FIG. 17 mainly shows the external appearance and shape of the microorganism-detecting apparatus while its main cross section is shown in FIG. 18.

FIGS. 19 to 33 show each of the elements constituting the microorganism-detecting apparatus in some more detail. Incidentally, in those drawings, a microorganism-collecting part or the like is sometimes omitted for better understanding.

Figure 19:
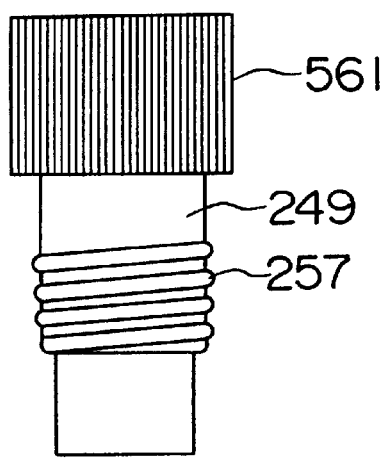
FIG. 19 shows an outer shape of a cap member (561) of the apparatus of FIG. 17.
Figure 20:
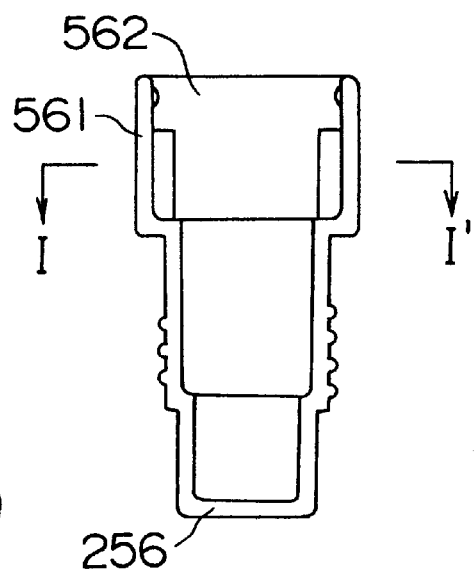
FIG. 20 shows a cross-sectional shape of a cap member (561) of FIG. 19.
Figure 21:
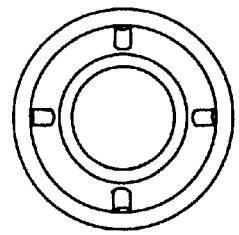
FIG. 21 shows a cross-sectional shape along I–I' of the cross sectional view of FIG. 20.
Figure 26:
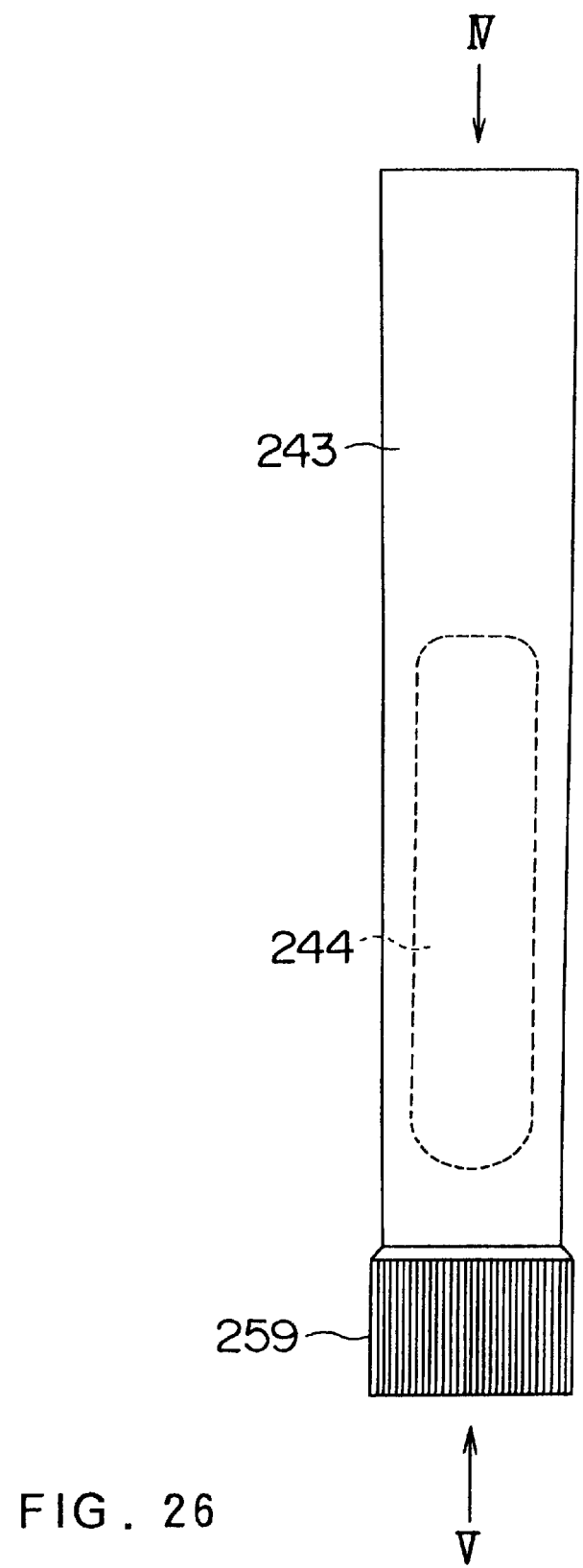
FIG. 26 shows an outer shape of the cover-constituting member (243) of the apparatus of FIG. 17.
Figure 27:
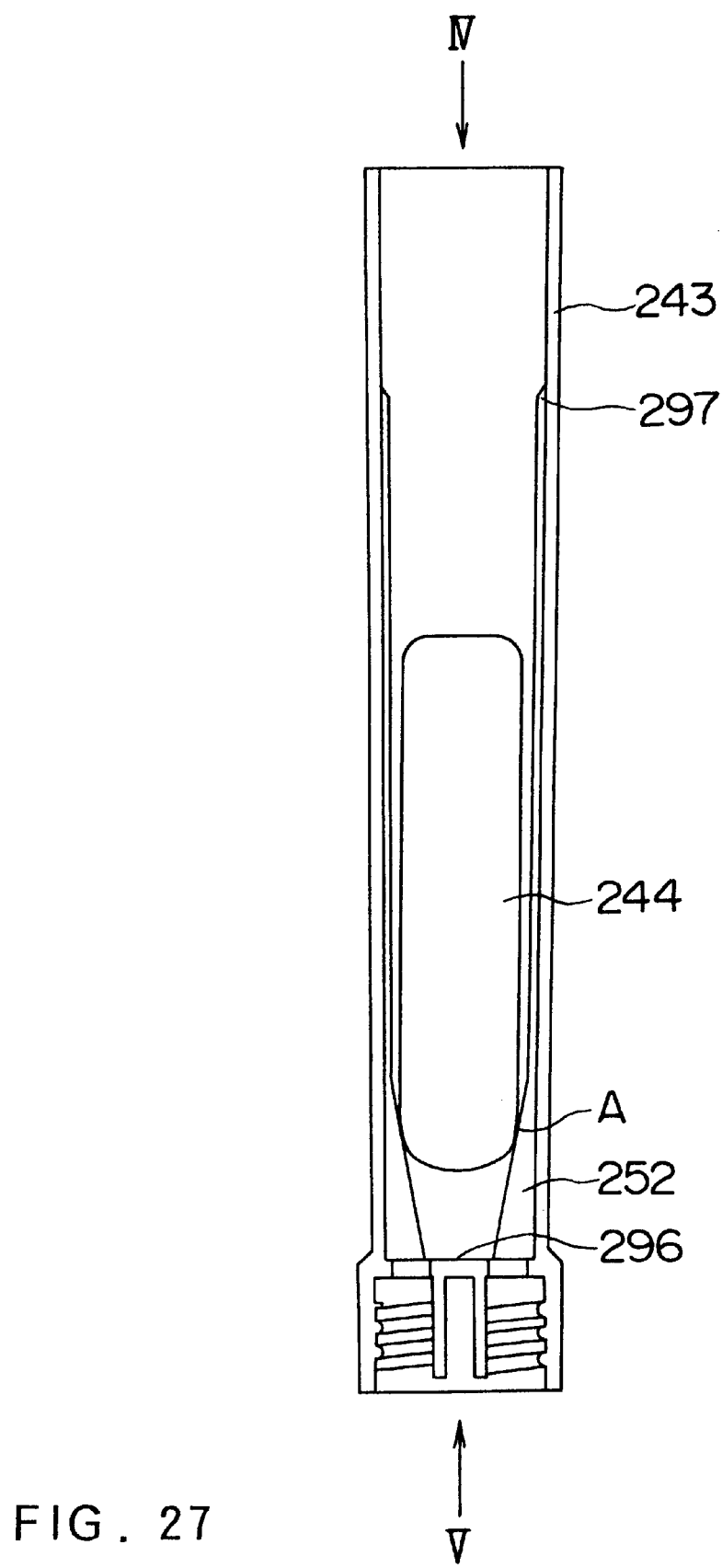
FIG. 27 shows a cross-sectional shape of the cover-constituting member (243) of FIG. 26.
Figure 32:
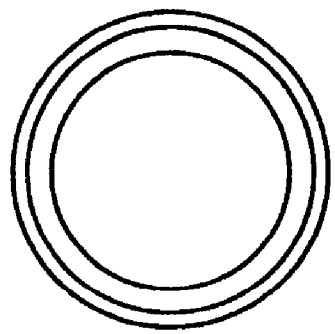
FIG. 32 shows an outer appearance of the container (241) of FIG. 30 from the direction of VI.
Figure 33:
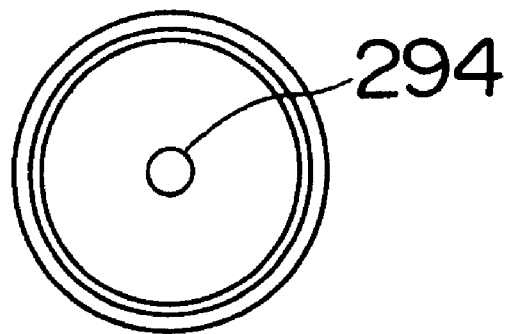
FIG. 33 shows a cross sectional shape along G–G' in the cross section of FIG. 31, wherein a cross section of the microorganism-collecting end (246b) is illustrated at its central portion.

A main appearance of a cap member (561) is shown in FIG. 19 while the cross sectional shape of said cap member (561) is mostly shown in FIG. 20. FIG. 21 is mostly a cross sectionally perspective view of the lower area seen from the section I–I' of the cap member. An appearance of the cover-constituting member (247) of the microorganism-detecting apparatus is mostly shown in FIG. 22 while the cross sectional view of the cover-constituting member (247) is mostly shown in FIG. 23. FIG. 24 mostly shows the appearance of the cover-constituting member (247) from the direction of II while FIG. 25 mostly shows the appearance of said cover-constituting member (247) from the direction of III. FIG. 26 mostly shows the appearance of the cover-constituting member (243) of the microorganism-detecting apparatus, FIG. 27 mostly shows the cross sectional view of the cover-constituting member (243), FIG. 28 mostly shows the appearance of the said cover-constituting member (243) from the direction IV and FIG. 29 mostly shows the appearance of the cover-constituting member (243) from the direction V, respectively. The appearance of the container (241) of the micro-organism-detecting apparatus is mostly shown in FIG. 30, and the cross sectional view of the container (241) is mostly shown in FIG. 31. FIG. 32 mostly shows the appearance of the container (241) from the direction of VI and FIG. 33 mostly shows the cross sectional view of the container (241) at the G–G' section in the microorganism-detecting apparatus equipped with the microorganism-collecting end (246b).

In FIGS. 17 and 18, the cover (242) is mainly composed of (a) a cover-constituting member (243) which is capable of receiving and holding an ampule (244) containing a medium; (b) a cover-constituting member (247) which is capable of receiving and holding an ampule (248) containing a disinfectant; and (c) a cap member (249, 561). A protrusion (252) is installed (formed) at the bottom of the cover-constituting member (243), i.e. at the connecting side (259) with the cylindrical container (241). The protrusion (252) may be placed on the entire circumference of the cover-constituting member (243) whereby the cover-constituting member (243) becomes thick at the connecting part (259) side with the container (241). Alternatively, the protrusion may be placed (formed) in such a manner that the protrusions are located in a projected manner at some places on the inner side of the cover-constituting member (243), e.g. those in a form of a crosspiece (sash bar). In an example shown in the drawing, it is noted that the protrusion is installed (formed) having a wedge-shaped cross section at four sites as given in FIG. 28. Such a shape of the protrusion (252) is effective in giving a big breaking force at the contacting point A with the ampule (244). Other examples of the shape, whereby such a function and merit can be expected, may be suitably selected by anyone skilled in the art from those which have been widely known in the areas of machines and instruments, particularly in the area of containers. In a preferred embodiment, a protrusion (297) is formed at the top side of the cover-constituting member (243), i.e. at the cap member (249) side terminal area, so as to engage with a engaging recess part (299) formed on the cover-constituting member (247) and, when the head part (245) of the cover-constituting member (247) is pushed to the direction of the container (241), the bottom (235) of the cover-constituting member (247) can be pushed against the side of the container (241).

Figure 28:
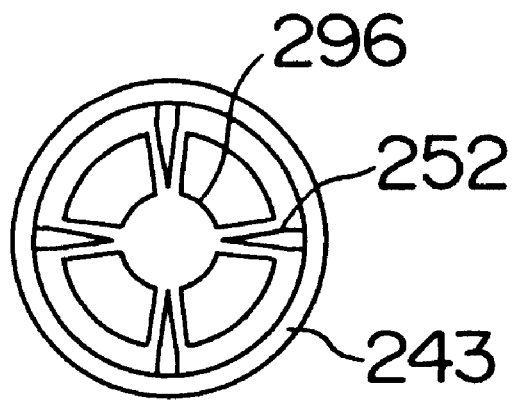
FIG. 28 shows an outer appearance of the cover-constituting member (243) of FIG. 26 from the direction of IV.
Figure 29:
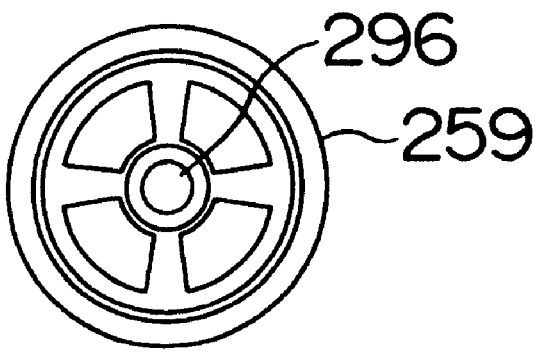
FIG. 29 shows an outer appearance of the cover-constituting member (243) of FIG. 26 from the direction of V.
Figure 30:
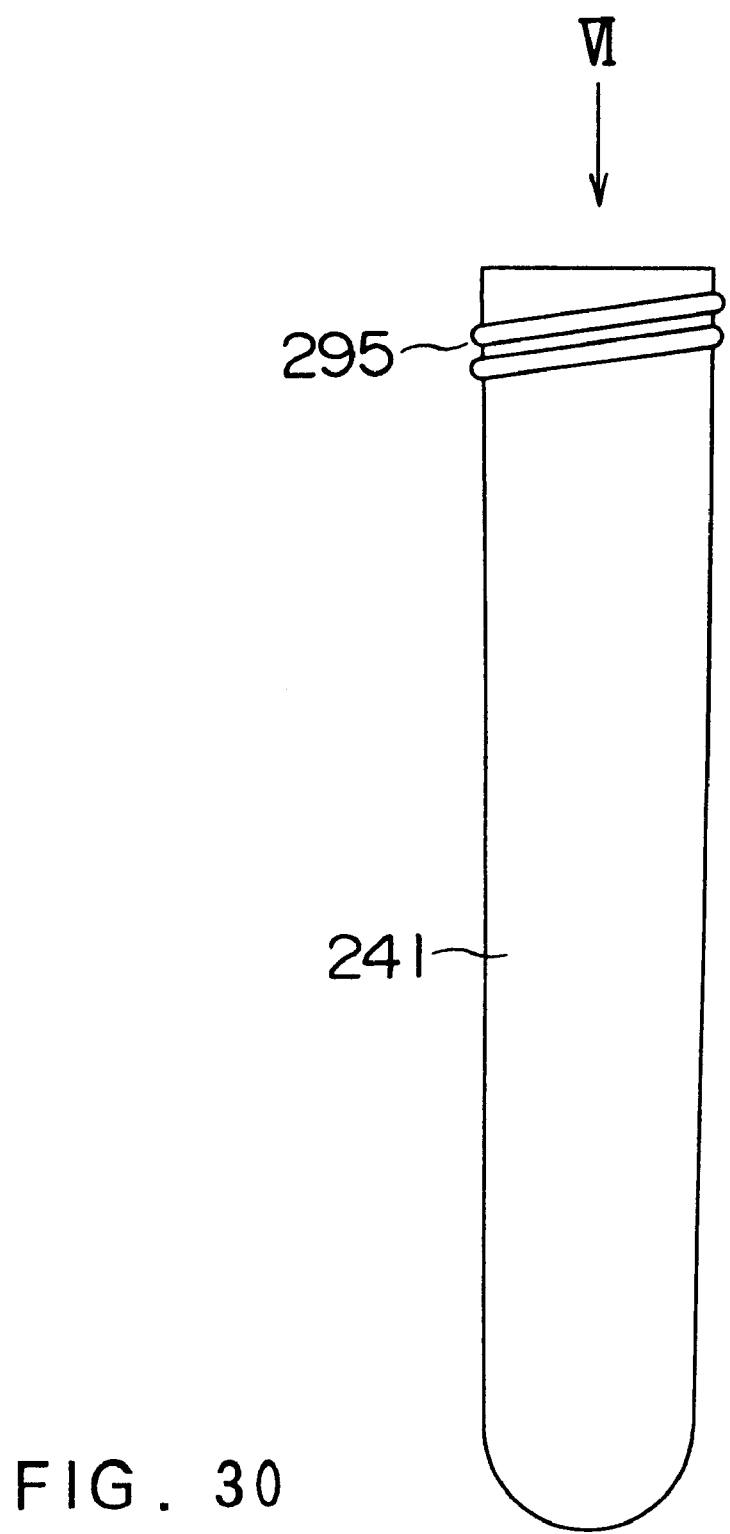
FIG. 30 shows an outer shape of the container (241) of the apparatus of FIG. 17.
Figure 31:
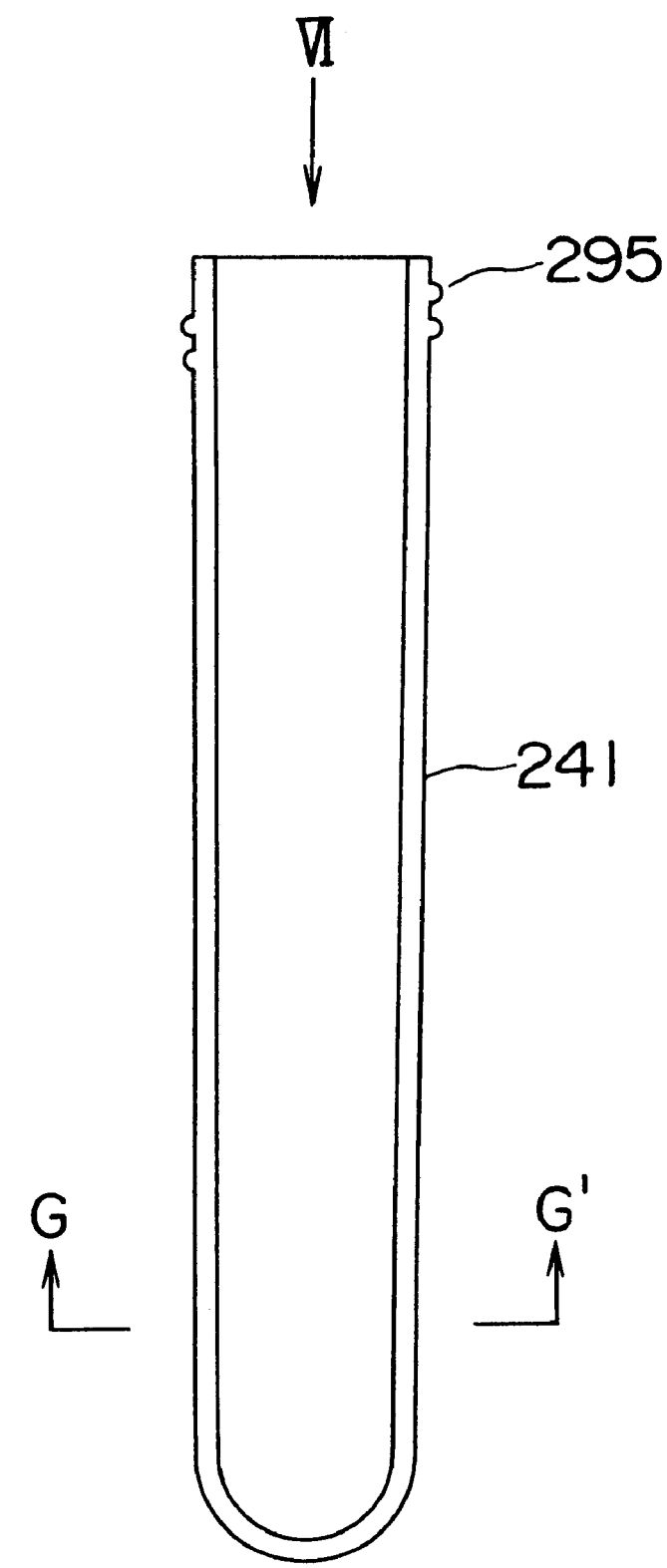
FIG. 31 shows a cross-sectional shape of the container (241) of FIG. 30.

In an example shown in this drawing, the protrusion (297) is formed at four places on the inner wall of a cylindrical member (243), the same as the protrusion (252) which is shown in FIG. 28 and, corresponding to that, the connection recess part (299) is formed at four places on the outer wall of the member (247) at the side of the container (241). There is no particular limitation for their structures in connection with such protrusions (297) and connection recess parts (299) as long as they can engage each other for setting the cover-constituting member (247) at the inner side of the cover-constituting member (243) and the cover-constituting member (247) can slide to the side of the container (241) preferably at the breaking stage of the ampule (244). The shape and structure can be suitably selected from those which are widely known in the areas of machines and instruments, particularly in the area of containers, by anyone skilled in the art provided that the function and the merit as mentioned above can be expected. At the bottom (235) of the cover-constituting member (247), there are one or more through holes (perforated holes) (cf. FIG. 25) so that, when the ampule (248) is broken, the disinfectant contained therein can flow down into the container (241) as mentioned below. At the bottom side of the cover-constituting member (247), i.e. at the inner ampule (244) side, there is a protrusion (253) by the same manner as in the case of the cover-constituting member (243). Like the above-mentioned protrusion (252), the protrusion (253) may be made on the entire circumference of the cover-constituting member (247) whereby the cover-constituting member (247) becomes thick at the bottom of the ampule (244) side thereof. Alternatively, the protrusion (253) may be made in such a manner that the projected parts are partially available at several places on the inner side of the cover-constituting member (247) (such as a protrusion in a form of crosspieces). In an example shown in this drawing, it is noted that, as shown in FIG. 24, the protrusion (253) is installed in such a manner that it has a wedge-like cross section at four sites. In a preferred embodiment, threads are made at the top side of the cover-constituting member (247), i.e. on the end (245) at the cap member (249) side, so as to cooperate with screws (257) made on the cap member (249) and, when the head of the cap member (249) is rotated, the bottom (256) of the cap member (249) can be pushed against the side of the ampule (248).

As well noted by referring to FIG. 18 for example, when the head (245) of the cover-constituting member (247) is first pushed down in the direction of the container (241) and then the cover-constituting member (247) is pushed into the cover-constituting member (243), the bottom (235) of the cover-constituting member (247) pushes down the ampule (244). The pushed-down ampule (244) is then supported by a slope of the protrusion (252) made on the cover-constituting member (243). As such, a tension would occur at the contacting point (A) of the ampule (244) with the slope of the protrusion (252) as the cover-constituting member (247) is pushed down to the side of the container (241) whereby the lower part of the ampule (244) is broken and the contents therein is allowed to release. The contents released from the ampule (244) flows into the container (241) by gravity passing the through hole (perforated hole) (cf. FIG. 29) made in the first partition member (296) and contacts with the microorganism-collecting end (246b). (Incidentally, in FIG. 28, the ampule (244) is omitted and, further, in FIG. 29, the microorganism-collecting part which is to be made at the central site is omitted.) In an example shown in this drawing, there are four through holes in a fan-like shape as will be noted by referring to FIGS. 28 and 29.

During the disinfecting stage after incubation of the microorganism, when the top (561) of the cap member (249) is rotated and the bottom (256) of the cap member (249) is pushed against the side of the ampule (248), the bottom (256) of the cap member (249) pushes down the ampule (248). The pushed-down ampule (248) is then supported by the slope of the protrusion (253) made on the inner side of the cover-constituting member (247). As the cap member (249) is rotated and pushed against the side of the container (241), a tension would occur at the contacting point (B) of the ampule (248) with the slope of the protrusion (253) whereby the lower part of the ampule (248) is broken and the contents therein is allowed to release. The contents coming out from the ampule (248) flows into the container (241) by gravity passing through the perforated holes (cf. FIG. 25) made at the bottom (235) of the cover-constituting member (247) and contacts with the incubated microorganism. (Incidentally, in FIG. 24, the ampule (248) is omitted.) In an example shown in this drawing, there are four perforated holes (through holes) in a sectoral form as will be noted by referring to FIGS. 24 and 25. It is preferred in view of convenient use that the ampule is made of glass, hard plastics, etc. so that it can be easily broken upon application of mechanical force (particularly upon application of a mechanical force partially).

In the microorganism-detecting apparatus shown in the drawings, the ampule containing the medium can be broken by mere sliding and pushing of the cover-constituting member and the cap member (both are screwed and unitedly movable) to supply the medium for incubation to the container while another ampule containing a disinfectant/sterilizer can be broken to release the disinfectant/sterilizer contained therein into a container for incubation only when the cap member screw-fitted with the cover-constituting member accommodating the disinfectant/sterilizer ampule is rotated and pushed thereagainst. Therefore, the microorganism-detecting apparatus is excellent in terms of actual use.

In the microorganism-detecting apparatus of the present invention, it is also possible that a lock function is installed so that initiation of the sliding operation does not take place unless a certain force is applied thereto. It is further possible that initiation of the rotary movement of the cap member does not take place unless a certain force is applied thereto.

With regard to a structure giving such a lock function, those which are known in the area of containers may be selected and used. There is no particular limitation for the size of the microorganism-detecting apparatus but, in terms of portability, the total size will be, for example, about 5 to 40 cm in length (preferably, about 10 to 30 cm or, more preferably, about 15 to 25 cm) and about 3 to 50 mm in diameter (preferably, about 6 to 30 mm or, more preferably, about 8 to 25 mm). The size of the microorganism-detecting apparatus may be other than those given hereinabove and freely selected and designed by anyone skilled in the art depending upon the object and operability and also by taking the quality, etc. of the material constituting the apparatus into consideration.

FIGS. 34 to 51 illustrate other representative specific examples of the microorganism-detecting apparatus of the present invention for their fundamental constitution, particularly the fundamental constitution as a structure for disinfecting and/or sterilizing the cultured medium, etc. after incubation.

Figure 34:
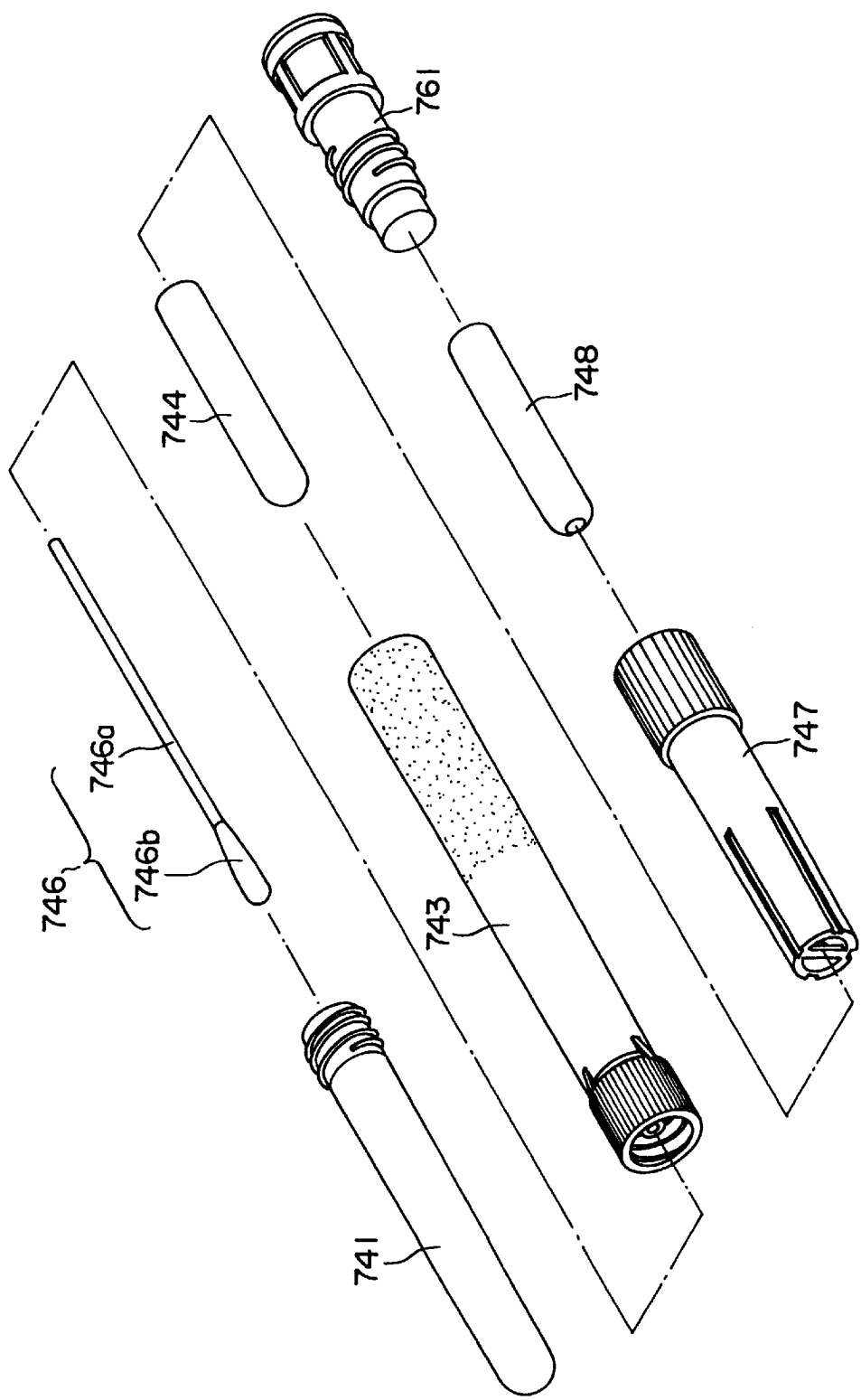
FIG. 34 is a schematic view of composition of the members which constitute the microorganism-detecting apparatus of the present invention.

FIG. 34 illustrates the assembling of the parts which constitute the microorganism-detecting apparatus according to the present invention. FIG. 34 shows a cap member (761), an ampule (748) wherein a disinfectant is contained, a cover-constituting member (747) capable of receiving and holding the ampule (748), an ampule (744) containing a medium, a cover-constituting member (743) capable of receiving and storing the ampule (744), a microorganism-collecting member (746) (comprising a rod-shaped element (746a) and a microorganism-collecting end (746b)) and a container (741). The assembling concept as shown in FIG. 34 is applicable to the microorganism-detecting apparatus of the present invention shown in FIGS. 17 to 33 as well.

Figure 22:
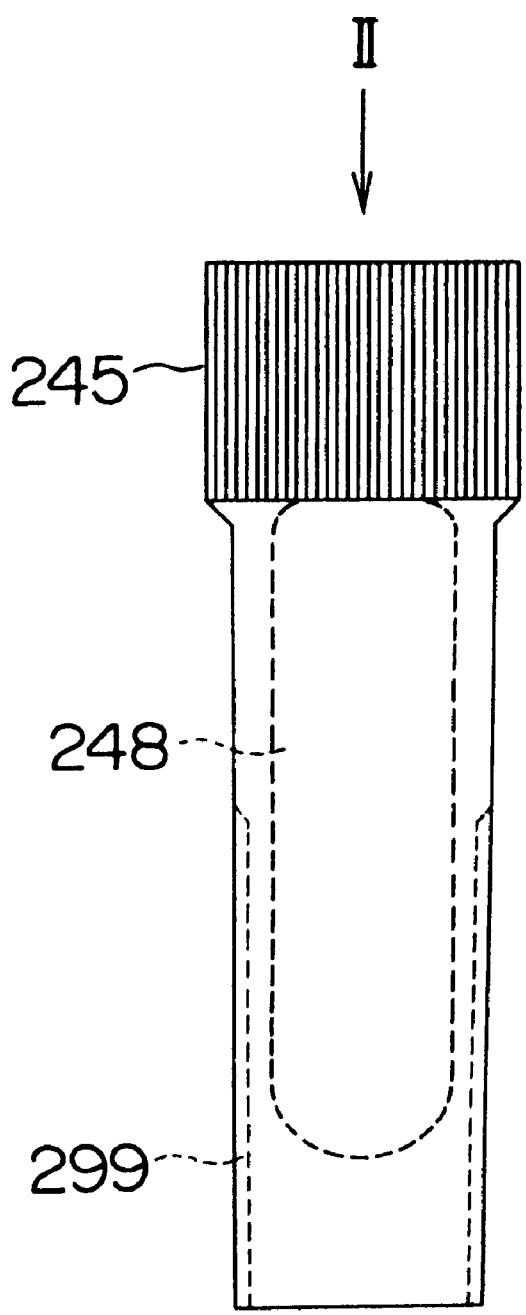
FIG. 22 shows an outer shape of the cover-constituting member (247) of the apparatus of FIG. 17.
Figure 35:
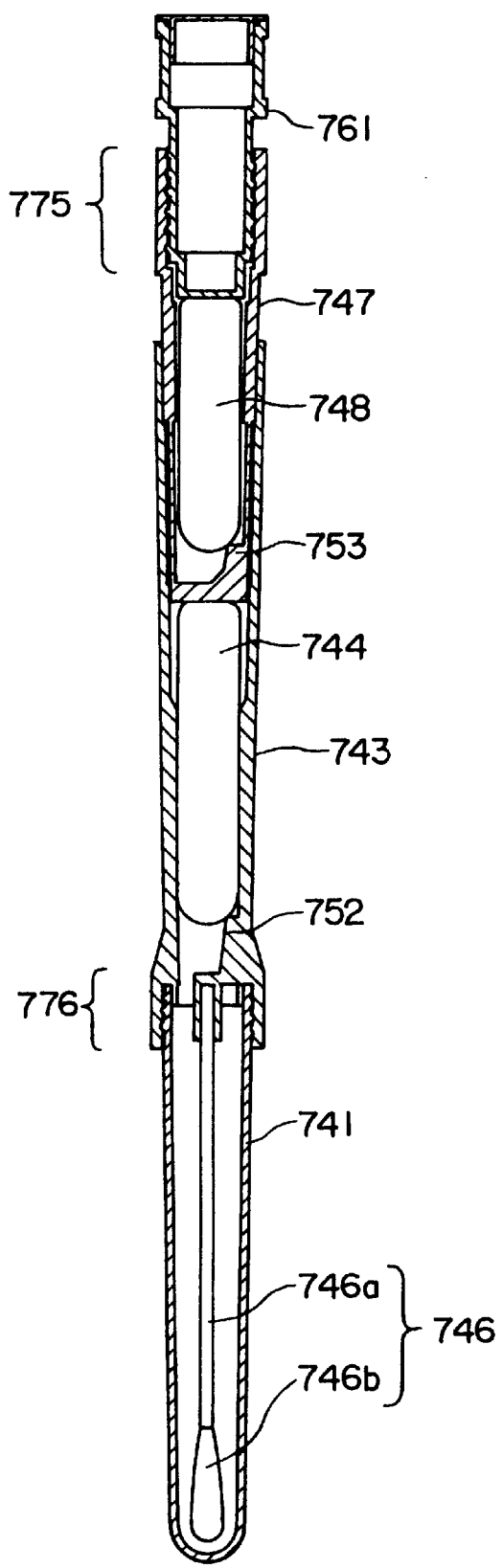
FIG. 35 shows an embodiment of the microorganism-detecting apparatus of the present invention and a cross-sectional shape is shown here.
Figure 36:
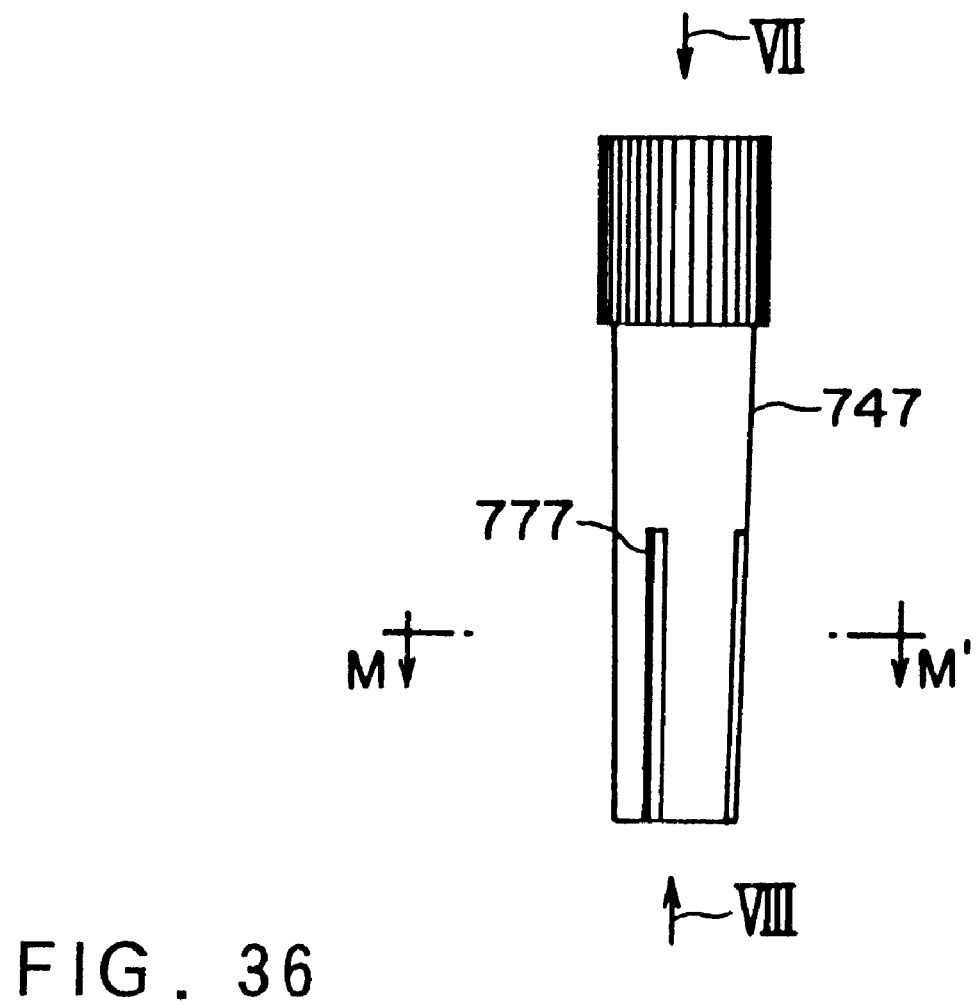
FIG. 36 shows an outer shape of the cover-constituting member (747) of FIG. 35.
Figure 37:
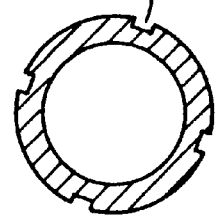
FIG. 37 is a cross-sectional view taken along lines M–M' of the cover-constituting member (747) of FIG. 36.
Figure 38:
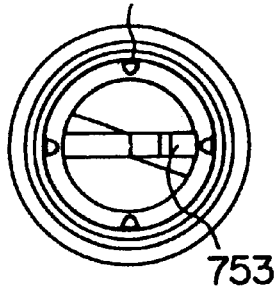
FIG. 38 shows an outer shape of the cover-constituting member (747) of FIG. 36 from the direction of VII.
Figure 39:
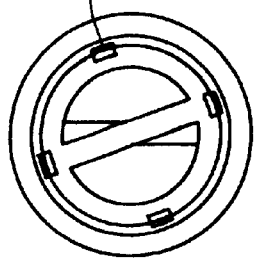
FIG. 39 shows an outer shape of the cover-constituting member (747) of FIG. 36 from the direction of VIII.

FIG. 35 mostly shows the cross-sectional shape of the microorganism-detecting apparatus. FIG. 36 mostly shows the appearance of the cover-constituting member (747) of the microorganism-detecting apparatus which is similar to that as shown in FIG. 22. FIG. 37 mostly shows the cross-sectional view of the cover-constituting member (747) along the line M–M'; FIG. 38 mostly shows the appearance of the cover-constituting member (747) observed from the direction of VII; and FIG. 39 mostly shows the appearance of the cover-constituting member (747) observed from the direction of VIII (In FIGS. 38 and 39, a bridge part at the end of the cover-constituting member (747) and at the container side, connecting to the protrusion (753), is observed wherein the thing which is shown as if obliquely crossing to the bridge is a "flash" which is incidentally formed upon molding of the plastic resin and, preferably, such a flash is to be detached in the actual product.)

Figure 23:
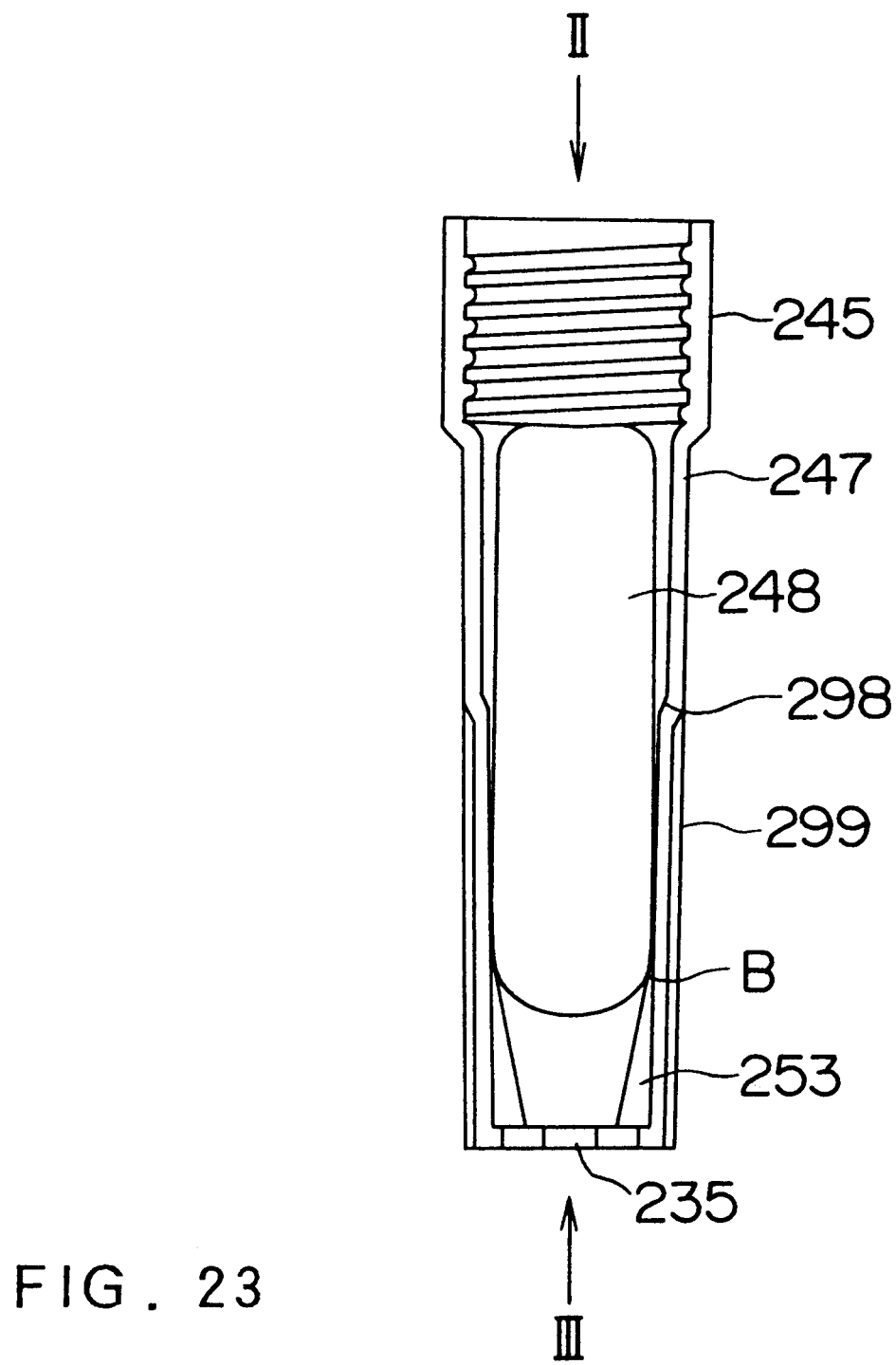
FIG. 23 shows a cross-sectional shape of the cover-constituting member (247) of FIG. 22.
Figure 24:
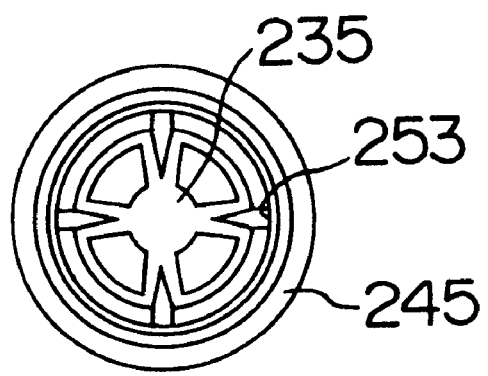
FIG. 24 shows an outer appearance of the cover-constituting member (247) of FIG. 22 from the direction of II.
Figure 25:
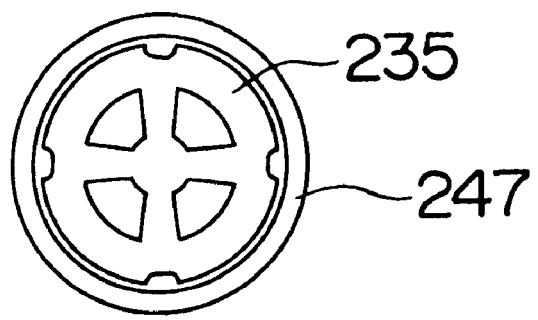
FIG. 25 shows an outer appearance of the cover-constituting member (247) of FIG. 22 from the direction of III.
Figure 40:
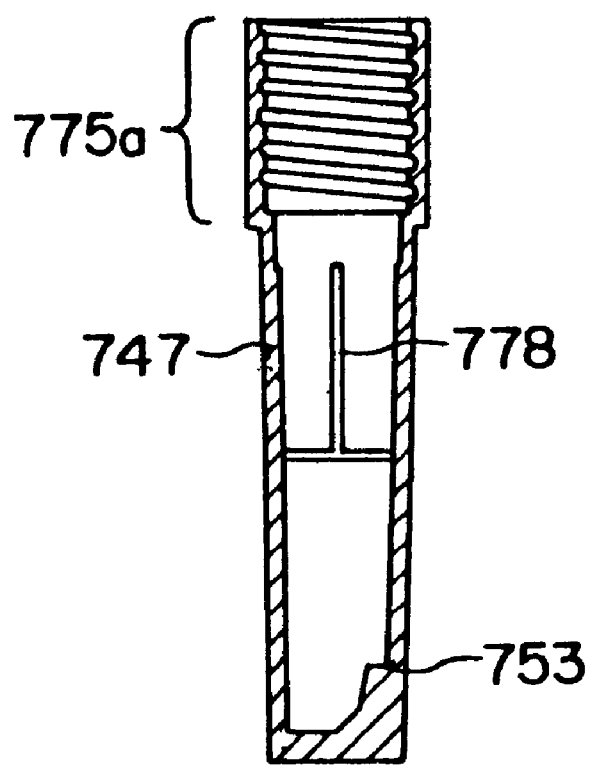
FIG. 40 shows a cross-sectional shape of the cover-constituting member (747) of FIG. 36.

FIG. 40 mostly shows the cross-sectional shape of the cover-constituting member (747) of the microorganism-detecting apparatus similar to that shown in FIG. 23 wherein (778) is a small convex ridge formed on the inner wall of the cover-constituting member (747) while (753) is a protrusion for breaking the ampule (748). Unlike the (253) shown in FIG. 23 (and also in FIG. 24), this (753) is formed only at one place (cf. FIG. 38) and, in addition, the shape is different (cf. FIG. 40). In the microorganism-detecting apparatus, such an ampule-breaking function and a structure for enabling this function are also characteristic features of the present invention. Accordingly, an apparatus and materials (members) having such a function constitute a part of the present invention.

As will be noted from FIG. 37, there is a concave (凹) and shallow groove (777) in this cover-constituting member (747). The groove (777) is formed in such a manner that, as will be illustrated later, it can be engaged with a small convex ridge (781, 782, 783, etc.) formed on the inner wall of the cover-constituting member (743) of the microorganism-detecting apparatus whose cross-sectional shape is mostly shown by FIG. 44. Although, in an example as shown in the drawing, length of all of four grooves (777) is the same, numbers and length of the groove may be suitably changed upon necessity. In FIG. 40, no perforated hole is illustrated through which a disinfectant (liquid) contained in the ampule (748) flows down by gravity when the ampule (748) is broken, but such a perforated hole (through hole) can be easily understood by referring to FIGS. 38 and 39.

In FIGS. 35 and 40, it is shown that the inner diameter of the about one-third portion of the cover-constituting member (747) at the side of the container (741) is either broader than or the same as the inner diameter at the side of its cap member (761), although it is also preferred that the inner diameter is narrower than that at the side of its cap member (761) so that the movement of the receiving ampule (748) is restricted.

Figure 41:
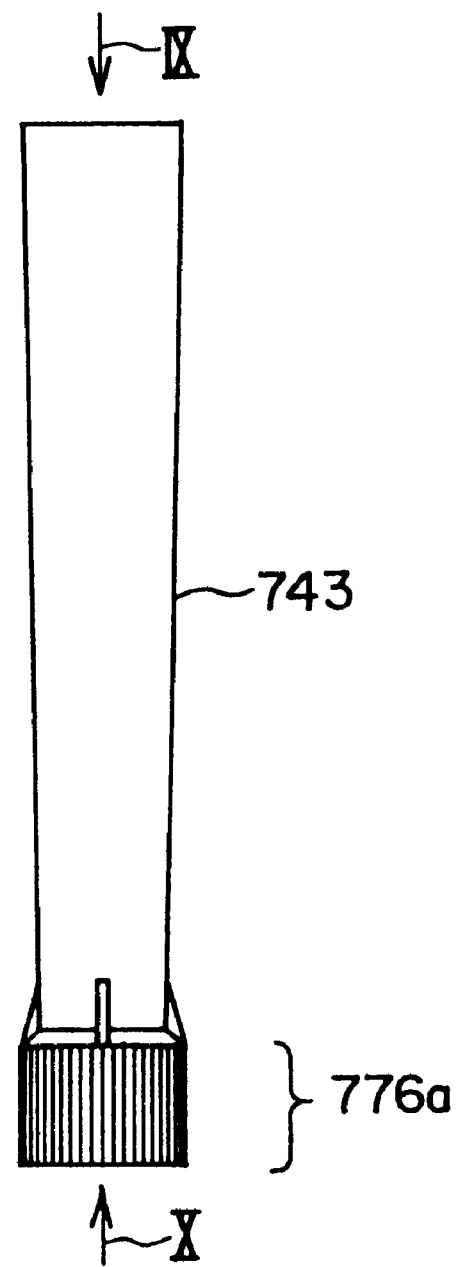
FIG. 41 shows a cross-sectional shape of the cover-constituting member (743) of FIG. 35.
Figure 42:
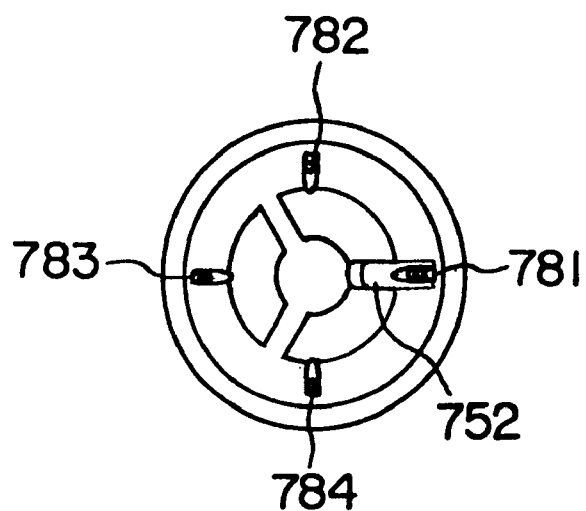
FIG. 42 shows an outer shape of the cover-constituting member (743) of FIG. 41 from the direction of IX.
Figure 43:
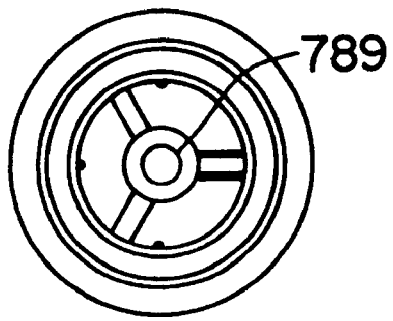
FIG. 43 shows an outer shape of the cover-constituting member (743) of FIG. 41 from the direction of X.

FIG. 41 mostly shows the appearance of the cover-constituting member (743) of the microorganism-detecting apparatus which is the same as that as shown in FIG. 26. FIG. 42 mostly shows the appearance of the cover-constituting member (743) observed from the direction of IX; and FIG. 43 mostly shows the appearance of the cover-constituting member (743) from the direction of X. By referring to FIGS. 35, 42 and 43, the presence of the through holes (perforated holes) through which the medium (liquid) contained in the ampule (744) flows down by gravity can be easily understood. In this example, there are three perforated holes (through holes) in a shape of a fan. When the ampule (748) is broken, the disinfectant (liquid) contained in the ampule (748) flows down by gravity through the perforated holes and comes into the container (741).

Figure 44:
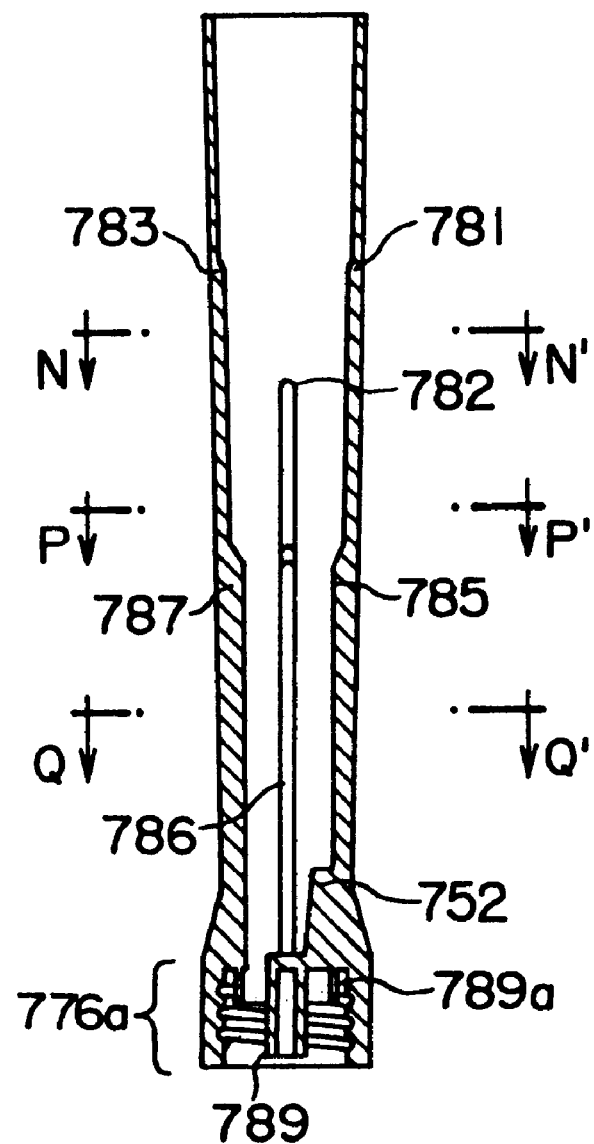
FIG. 44 shows a cross-sectional shape of the cover-constituting member (743) of FIG. 41.
Figure 45:
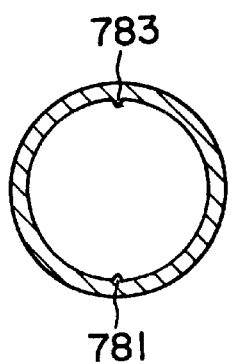
FIG. 45 is a cross-sectional view taken along lines N–N' of the cover-constituting member (743) of FIG. 44.
Figure 46:
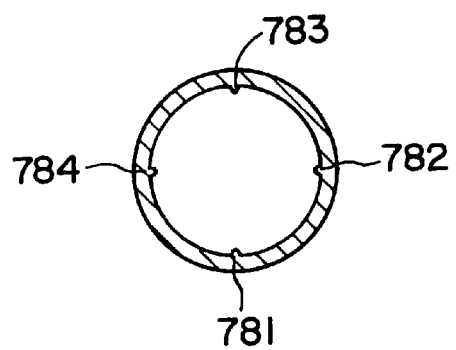
FIG. 46 is a cross-sectional view taken along lines P–P' of the cover-constituting member (743) of FIG. 44.
Figure 47:
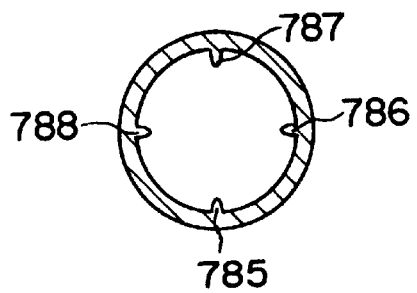
FIG. 47 is a cross-sectional view taken along lines Q–Q' of the cover-constituting member (743) of FIG. 44.

There are small convex ridges (781, 782, 783 and 784) on the inner wall of the cover-constituting member (743). In FIG. 44, there are two small convex ridges (781 and 783) in the plane N–N' (cf. FIG. 45 which illustrates a cross section along the plane N–N') but, in the P–P' plane, there are four (781, 782, 783 and 784) (cf. FIG. 46 which illustrates a cross section along the plane P–P'). FIG. 47 shows a cross section along the plane Q–Q'. The small convex ridge (781) ranges consecutively to (785) and further extends to (752) while, among others such as (782), it ranges to (786) but has no protrusion such as (752). Unlike (252) shown in FIG. 27, there is only one (752) in the present microorganism-detecting apparatus and its shape is different as well.

In the microorganism-detecting apparatus of the present invention, such an ampule-breaking function and a structure which makes it possible are also the characteristic features of the present invention and apparatus and materials (members) having such functions also constitute a part of the present invention.

Figure 48:
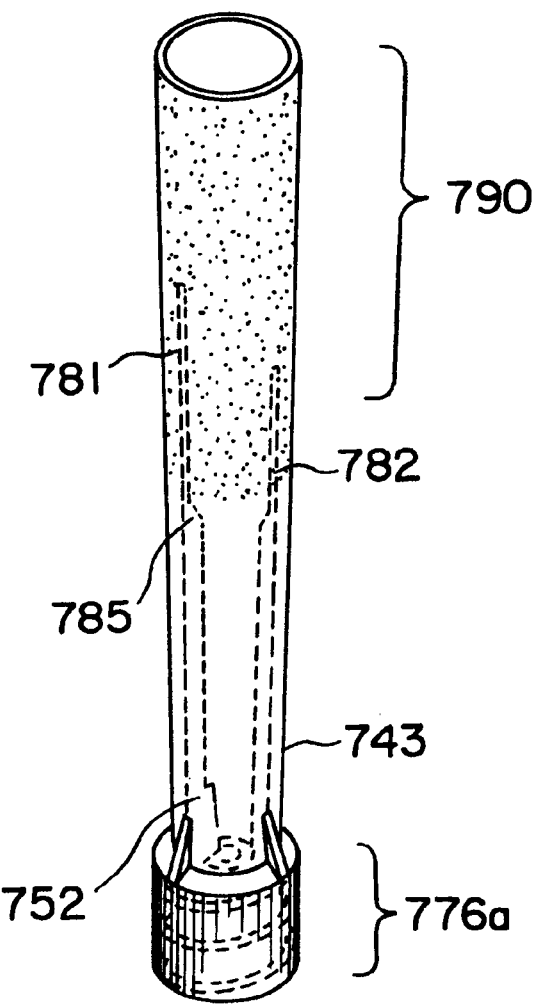
FIG. 48 is an oblique outer view of the cover-constituting member (743) of FIG. 41 which is made of a transparent (or translucent) material.

FIG. 48 shows the oblique outer view of the cover-constituting member (743) made up of a transparent (or translucent) material in a partly perspective manner. In the drawing, the arrangement of small convex ridges (781, 782 and also 785 and 752 ranging therefrom) formed on the inner wall of the cover-constituting member (743) is visible and understandable. (781) extends to the cover-constituting member (747)-receiving side longer than (782). The small convex ridges may be made in such a manner that the convex is made larger (i.e. projected to a higher extent) from the place (785) ranging therefrom for allowing the received ampule (744) to be loosely fixed. The area (790) at the outer wall of the cover-constituting member (743) is made hardly slippery by forming a finely indented surface, like a frosted glass. Such a finely indented surface, like a frosted glass, may be at either a part of or whole of the cover-constituting member (743).

The basic shape of the apparatus shown in FIGS. 34 to 51 is the same as that of the microorganism-detecting apparatus of the present invention shown in FIGS. 17 to 33 but its characteristic feature is as follows:

Until an initiation of incubation, the cover-constituting member (747) is set free by means of a locking mechanism from pushing into the cover-constituting member (743) to break the ampule (744) received in the cover-constituting member (743), while, upon the initiation of incubation, the engagement is easily unlocked by merely rotating the cover-constituting member (747) against the cover-constituting member (743) whereby the cover-constituting member (747) can be pushed into the cover-constituting member (743) so that the ampule (744) is broken and the medium can be supplied to the container (741).

Figure 49:
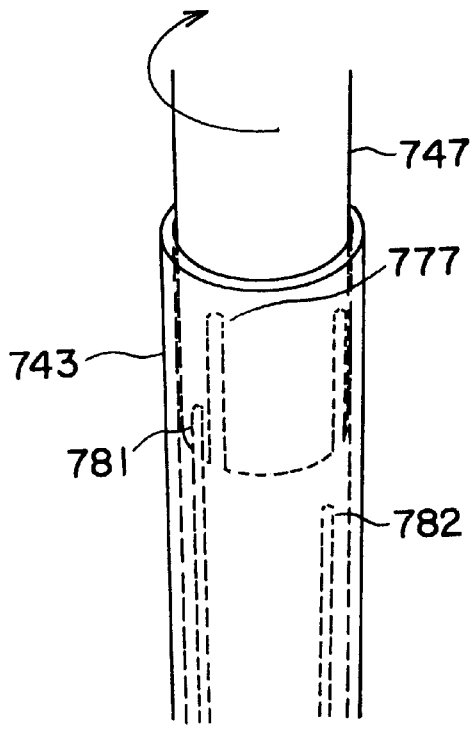
FIG. 49 is a conceptional view showing the relationship between the cover-constituting member (743) and that (747) shown in FIG. 35 by showing a small convex ridge (781) and a shallow concave groove (777). This is a state before incubation is started.
Figure 50:
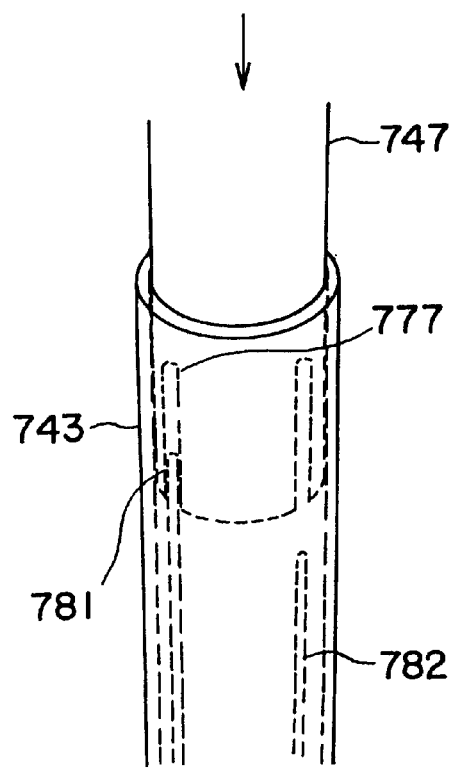
FIG. 50 is a conceptional view showing the relationship between the cover-constituting member (743) and that (747) shown in FIG. 35 by showing a small convex ridge (781) and a shallow concave groove (777). This shows an operation when incubation is started.
Figure 51:
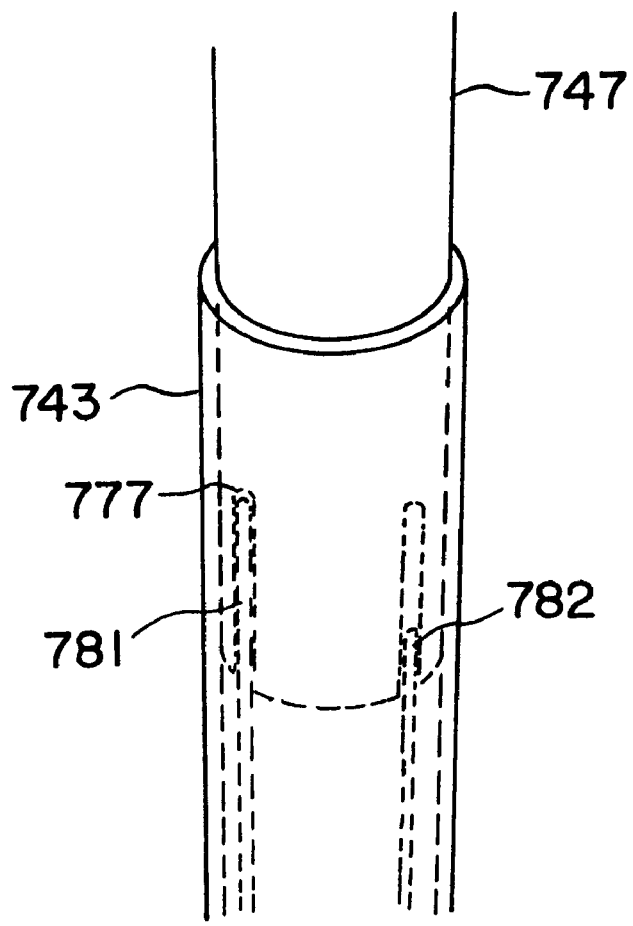
FIG. 51 is a conceptional view showing the relationship between the cover-constituting member (743) and that (747) shown in FIG. 35 by showing a small convex ridge (781) and a shallow concave groove (777). This is a state when the cover-constituting member (747) is pushed until a position where an ampule (744) is broken.

FIGS. 49 to 51 illustrate the conceptual outlines of the locking mechanism and unlocking thereof. At the state prior to use of the microorganism-detecting apparatus, when the cover-constituting member (747) is inserted into the cover-constituting member (743) in such a manner that (i) a long and convex (⊔) small ridge (781) formed on the inner side of the cover-constituting member (743) and (ii) a concave (⊓) and shallow groove (777) formed on the inner side of the cover-constituting member (747) are not engaged each other, both the cover-constituting members are fixed due to a big frictional engaging force between the convex small ridge (781) and the outer surface of the member (747). As a result, each member stays nearly at the position as shown by FIG. 49. In other words, the fixation is in such a manner that the member (747) cannot be pushed into the member (743) (i.e. against the side of the container) beyond the stopping position.

When, upon breaking the ampule (744), for example, the cover-constituting member (747) is rotated to the direction as shown by an arrow in FIG. 49, (i) the convex small ridge (781) and (ii) the concave and shallow groove (777) are engaged with each other as shown in FIG. 50, so that the frictional engaging force generated between the convex small ridge (781) and the outer surface of the cover-constituting member (747) disappears whereupon the cover-constituting member (747) can now be pushed in the direction further as shown by an arrow in FIG. 50. Then, when the cover-constituting member (747) is inserted as shown in FIG. 51, the bottom of the cover-constituting member (747) pushes the head of the ampule (744) whereupon the ampule is pushed to the protrusion (752) followed by breakage. In this example, (i) the convex ridges (four in total) formed on the inner side of the cover-constituting member (743) and (ii) the concave shallow grooves (four in total) (recessing parts) formed at the outer side of the cover-constituting member (747) are engaged with each other at the end. Simultaneously, the engaging surface of the cover-constituting member (743) and that of the cover-constituting member (747) are tightly engaged each other at the side of the cap member (761). Thus, the inner wall of the cover-constituting member (743) and the outer wall of the cover-constituting member (747) are tightly contacted with each other, thereby achieving a tight sealing to some extent. In the microorganism-detecting apparatus, such a locking mechanism and a structure for making it possible or available are a part of the characteristic features of the present invention and the apparatus having such a mechanism (or function) and materials (members) thereof constitute a part of the present invention.

The microorganism-detecting apparatus of the present invention as shown in FIGS. 34 to 51 are the same as those shown in FIGS. 17 to 33 in terms of basic shape, size, etc. and, accordingly, details of other materials will be and is to be understood similarly.

Figure 52:
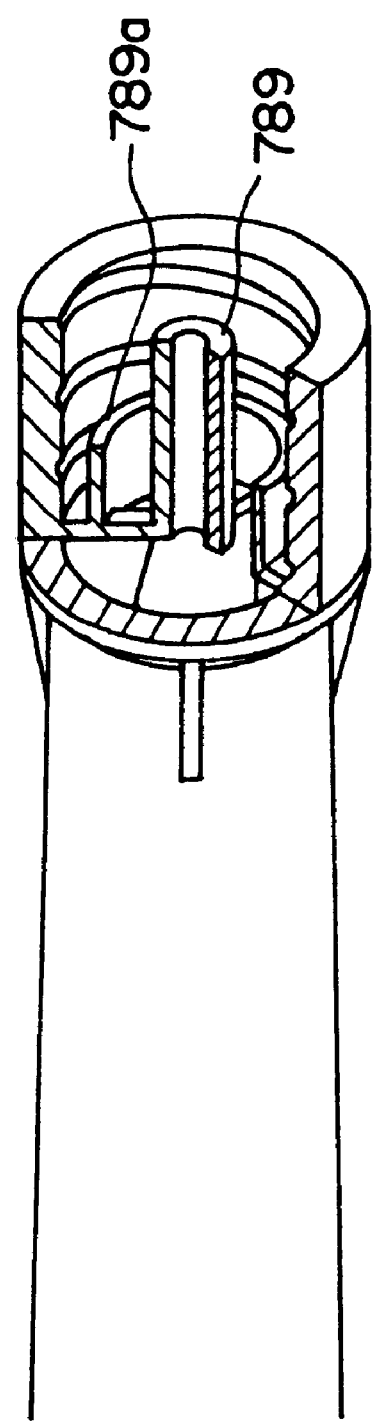
FIG. 52 shows a partial cross sectional view structure of a connecting part with a container in a cover-constituting member (e.g., 743).

FIG. 52 partly shows a partial cross sectional view of the connecting part (776a) of the cover-constituting member (743) with the container (741). It is understood that an end of the microorganism-collecting member (746) can be inserted into and fixed with the inlet (789) for the microorganism-collecting part (member). At the basement of the inlet (789), there is one or more perforating holes for communicating a medium and a disinfectant. As will be noted by referring to FIG. 52, a protrusion (789a) is formed in a manner surrounding the inlet (789). When an end of the container (741) is screwed into a connecting part (776a) of the cover-constituting member (743), the protrusion (789a) assists a close engagement (connection) of the cover-constituting member (743) with the container (741). In other words, when a plastic resin such as polypropylene is used as a constituting material for the engaging portions connecting between the cover-constituting member (743) and the container (741), it is possible to tightly seal it through utilizing the elasticity of the material of the members. In the microorganism-detecting apparatus according to the present invention, the structure of such a engaging part (776a) of the cover-constituting member (743) with the container (741) is also one of the characteristic features of the present invention and the apparatus having such a function and materials thereof also constitute a part of the present invention.

FIGS. 53 to 69 illustrate other representative specific embodiments of the microorganism-detecting apparatus according to the present invention for their fundamental constitution, particularly the fundamental arrangements suitable for disinfecting and/or sterilizing the cultured medium, etc. after incubation.

In these drawings, the microorganism-detecting apparatus according to the present invention is shown which has a mechanism for allowing a person to keep and carry it securely and which is designed in a manner that the person can avoid the breakage of (i) an ampule containing a disinfectant and (ii) an ampule containing a medium.

Figure 60:
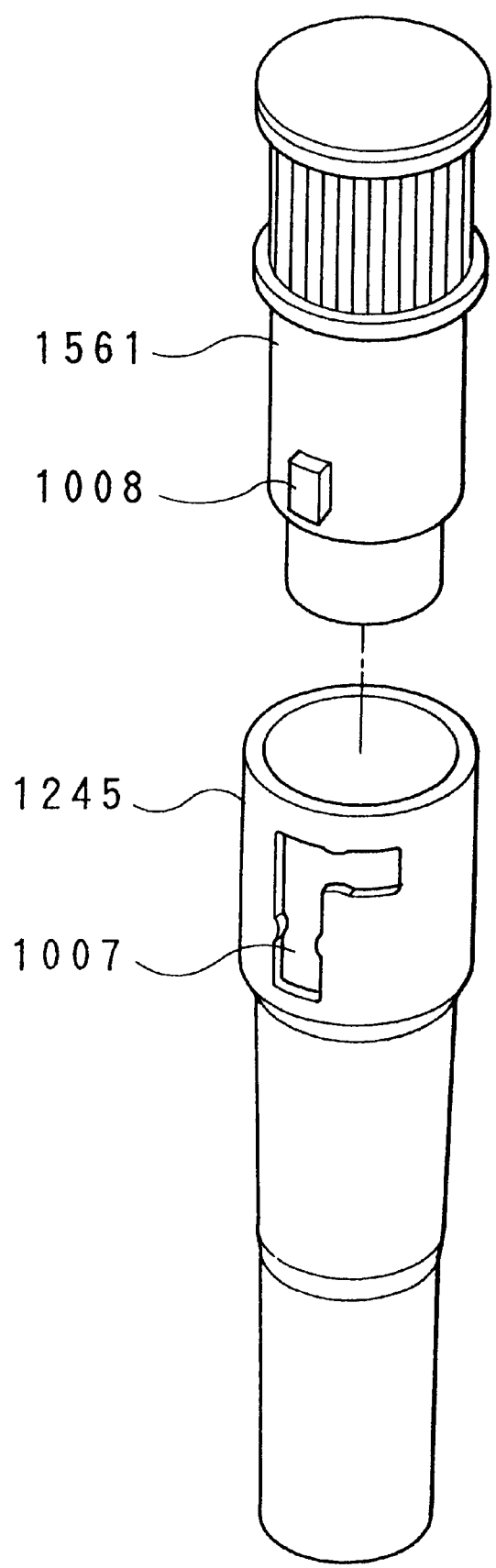
FIG. 60 illustrates perspectively the assembling of the parts 1561 and 1245 for the microorganism-detecting apparatus of FIG. 59.
Figure 61:
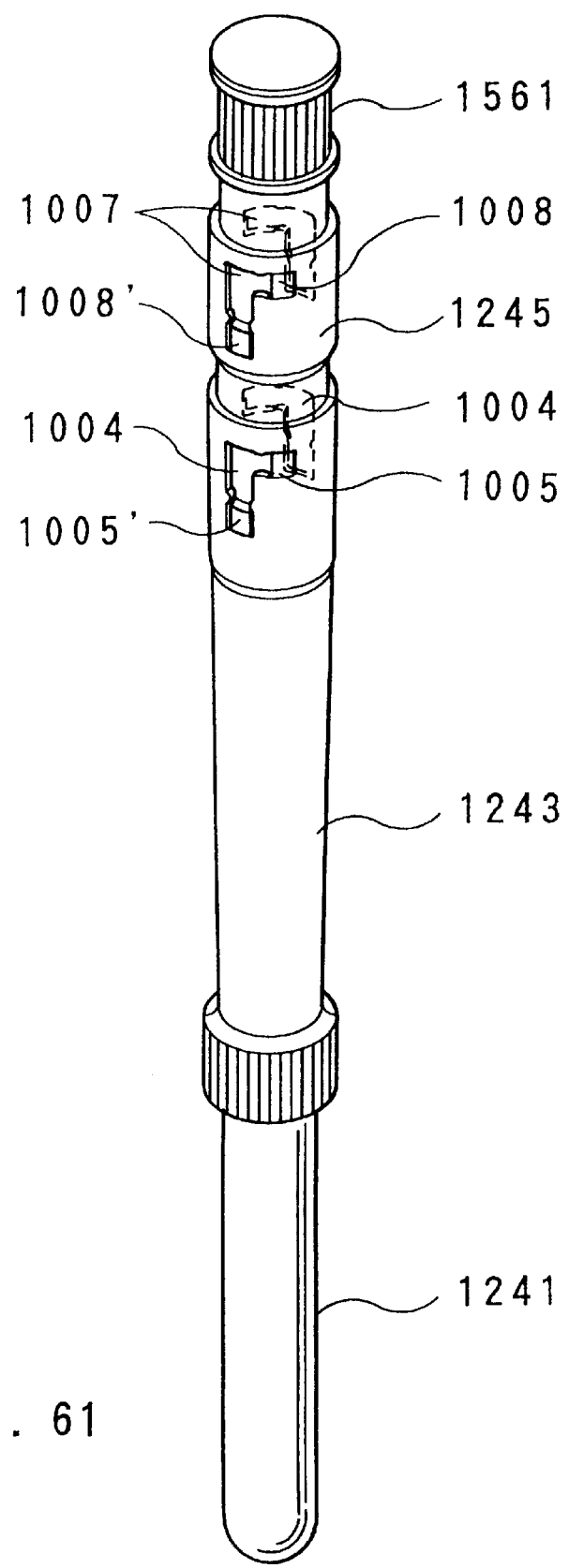
FIG. 61 is a perspective view of an embodiment of the microorganism-detecting apparatus according to the present invention.
Figure 62:
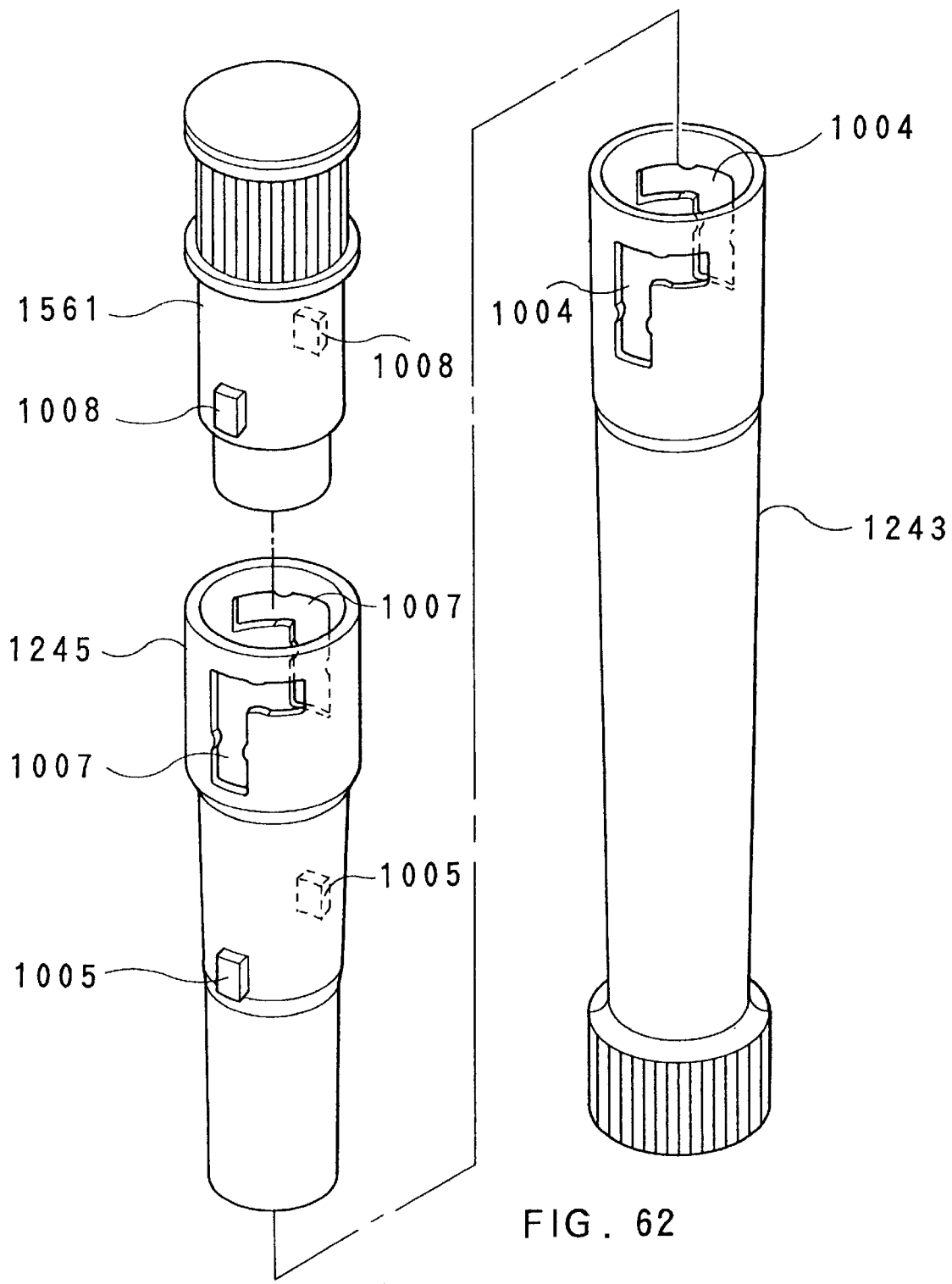
FIG. 62 illustrates perspectively the assembling of the parts 1561, 1245 and 1243 for the microorganism-detecting apparatus of FIG. 61.
Figure 63:
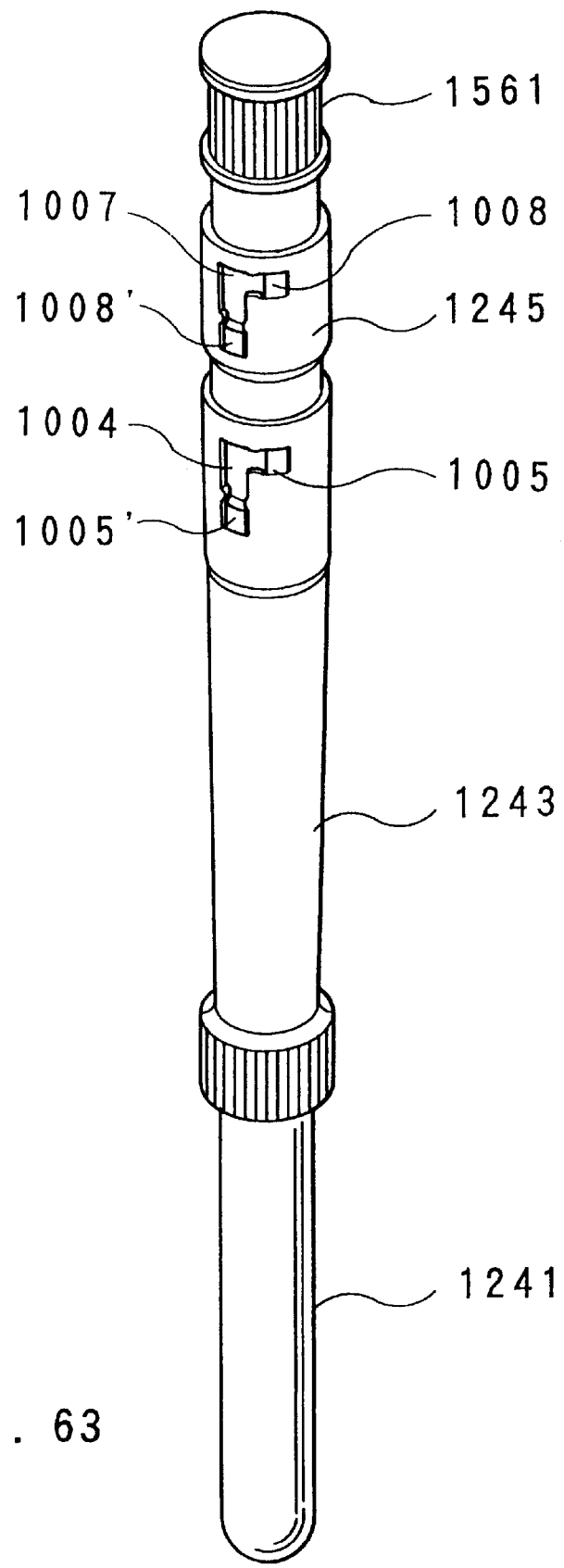
FIG. 63 is a perspective view of an embodiment of the microorganism-detecting apparatus according to the present invention.
Figure 64:
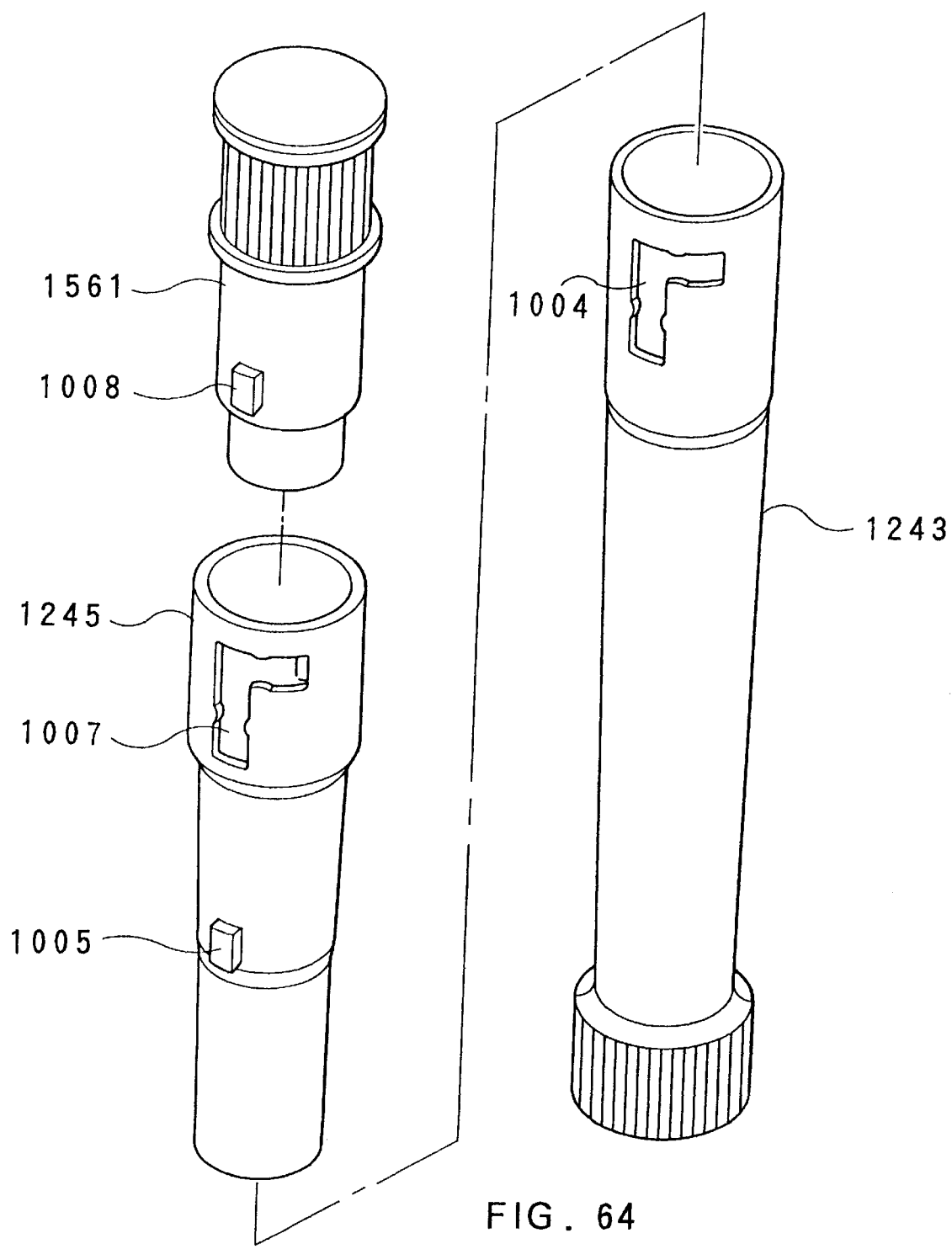
FIG. 64 illustrates perspectively the assembling of the parts 1561, 1245 and 1243 for the microorganism-detecting apparatus of FIG. 63.

FIGS. 53, 55, 57, 59, 61, and 63 show a perspective view of the microorganism-detecting apparatus according to the present invention, respectively. FIG. 54 illustrates the assembling of the parts 1245 (and 1561) and 1243 for the microorganism-detecting apparatus of FIG. 53. FIG. 56 illustrates the assembling of the parts 1245 (and 1561) and 1243 for the microorganism-detecting apparatus of FIG. 55. FIG. 58 illustrates the assembling of the parts 1561 and 1245 for the microorganism-detecting apparatus of FIG. 57. FIG. 60 illustrates the assembling of the parts 1561 and 1245 for the microorganism-detecting apparatus of FIG. 59. FIG. 62 illustrates the assembling of the parts 1561, 1245 and 1243 for the microorganism-detecting apparatus of FIG. 61. FIG. 64 illustrates the assembling of the parts 1561, 1245 and 1243 for the microorganism-detecting apparatus of FIG. 63.

Figure 53:
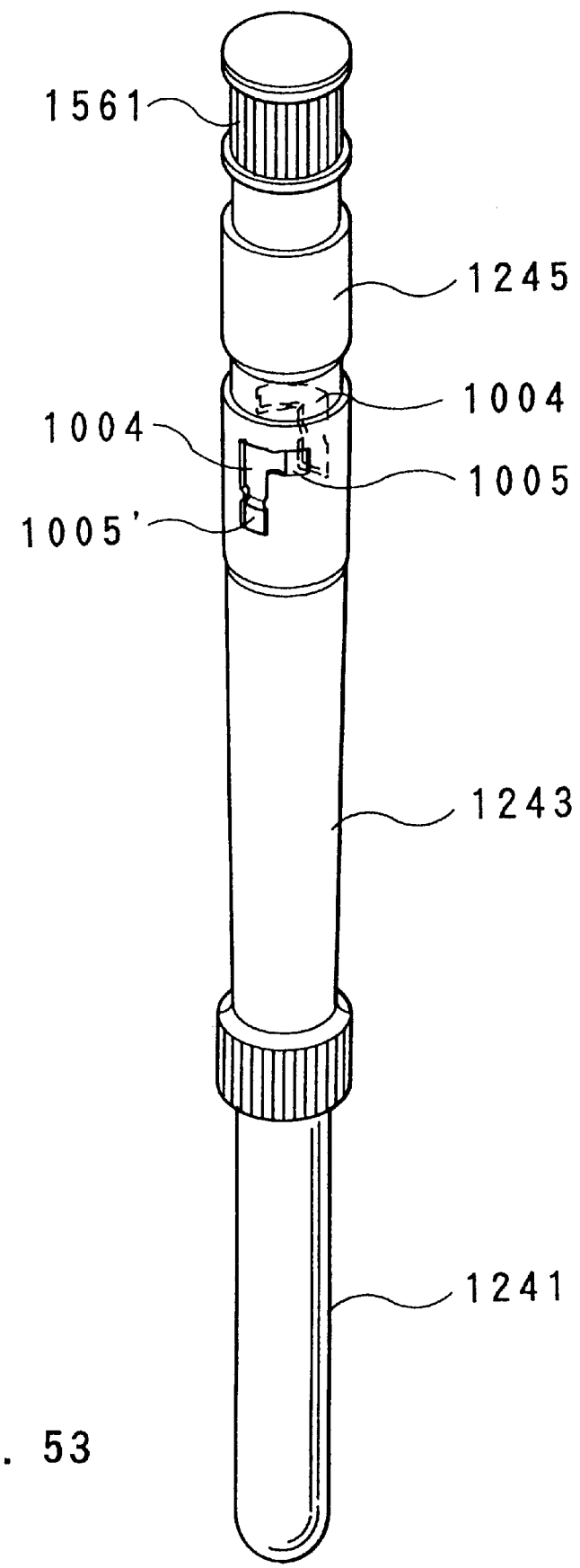
FIG. 53 is a perspective view of an embodiment of the microorganism-detecting apparatus according to the present invention.
Figure 54:
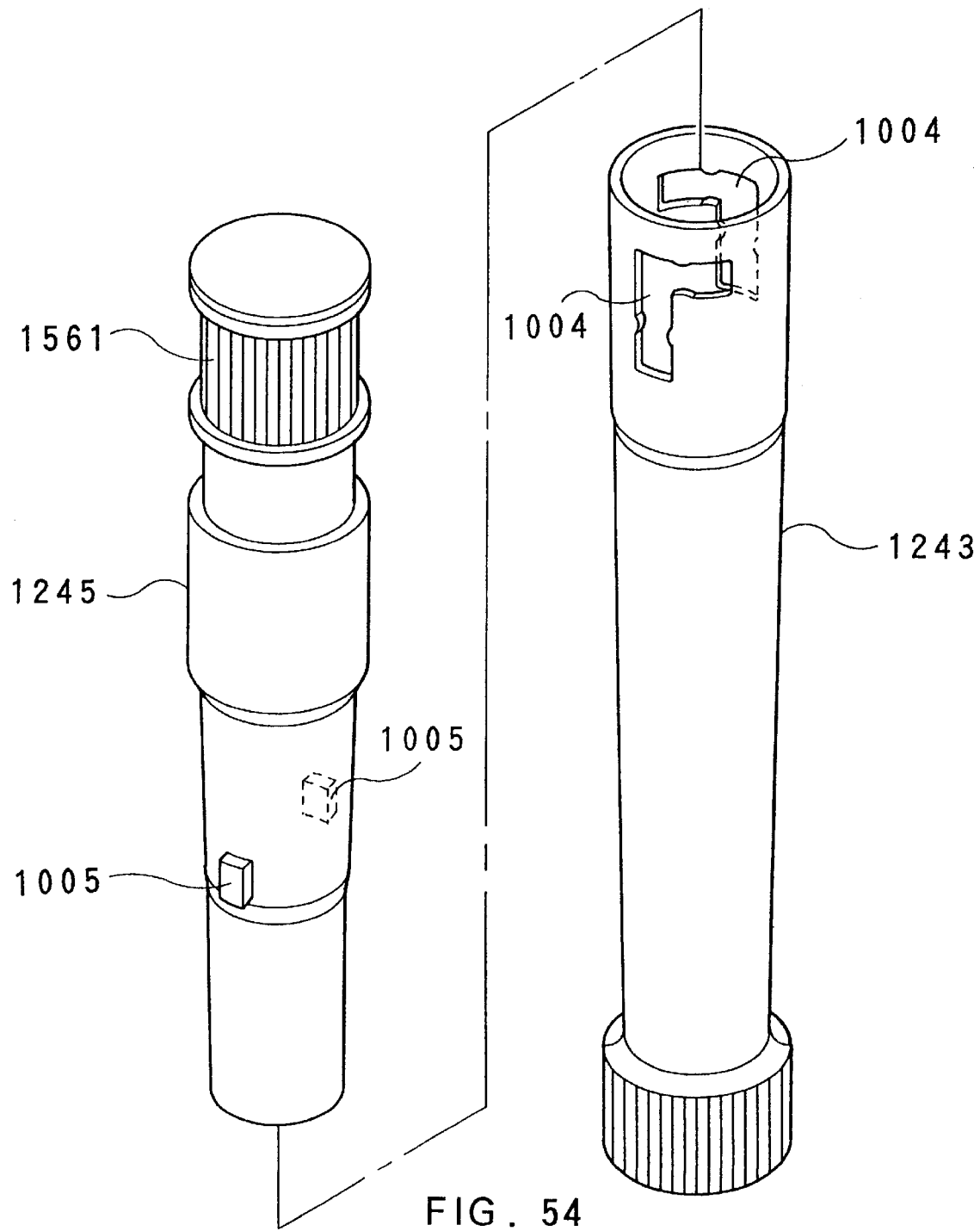
FIG. 54 illustrates perspectively the assembling of the parts 1245 (and 1561) and 1243 for the microorganism-detecting apparatus of FIG. 53.
Figure 55:
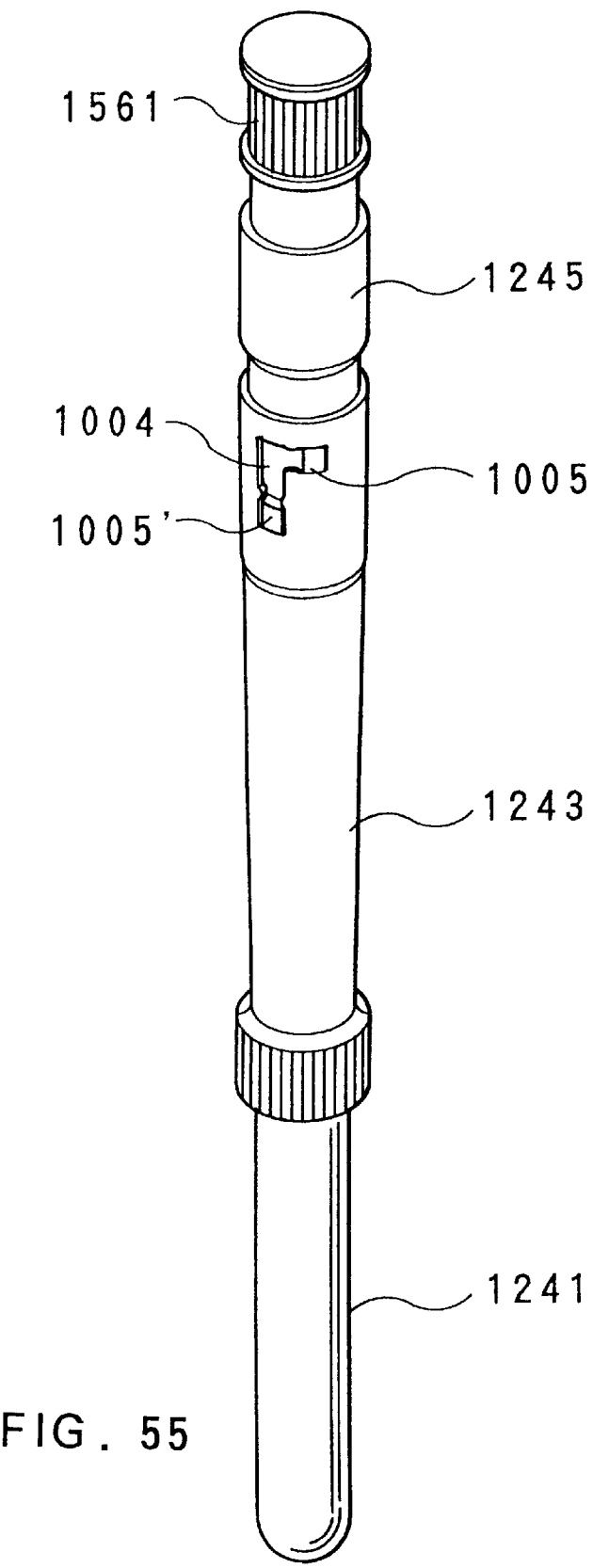
FIG. 55 is a perspective view of an embodiment of the microorganism-detecting apparatus according to the present invention.
Figure 56:
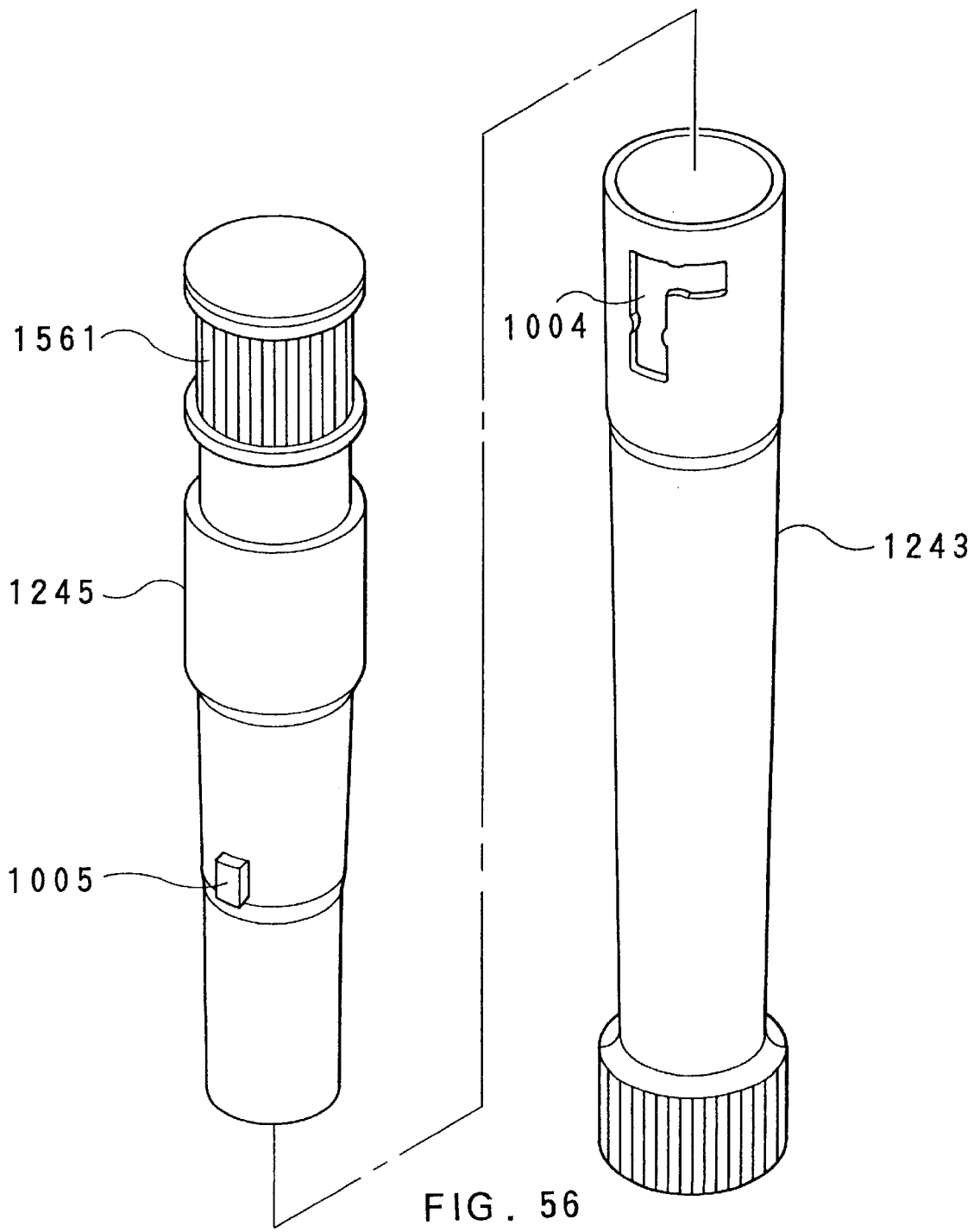
FIG. 56 illustrates perspectively the assembling of the parts 1245 (and 1561) and 1243 for the microorganism-detecting apparatus of FIG. 55.
Figure 57:
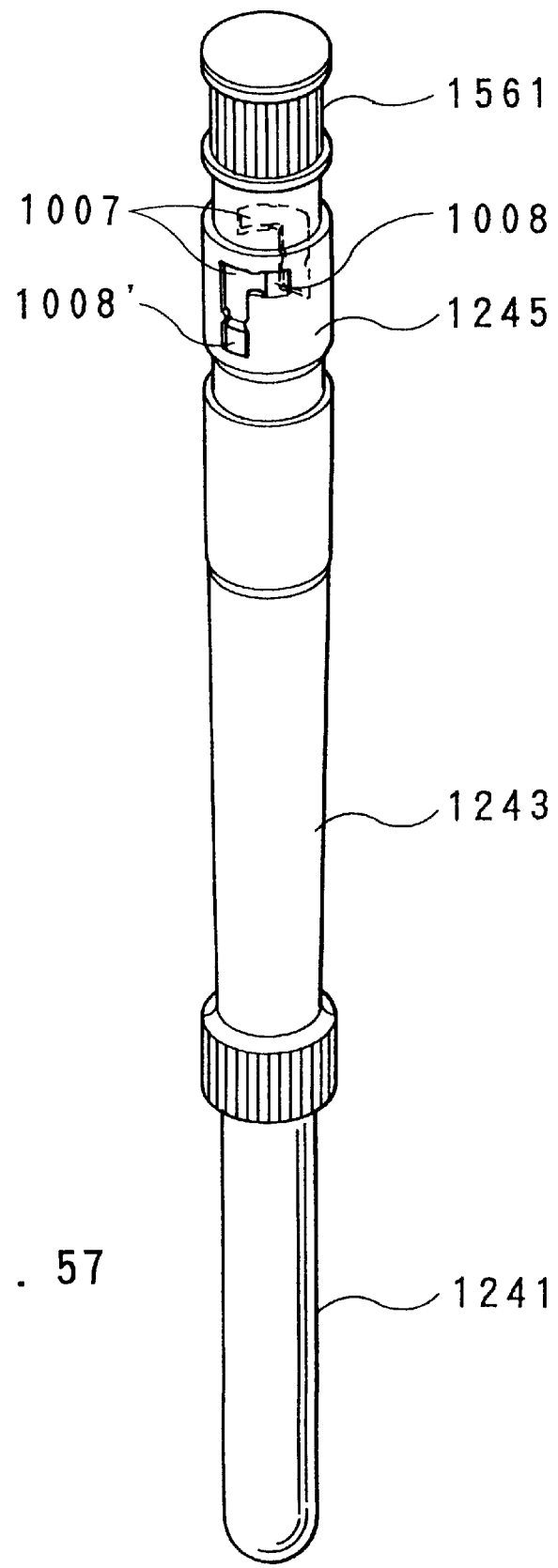
FIG. 57 is a perspective view of an embodiment of the microorganism-detecting apparatus according to the present invention.
Figure 58:
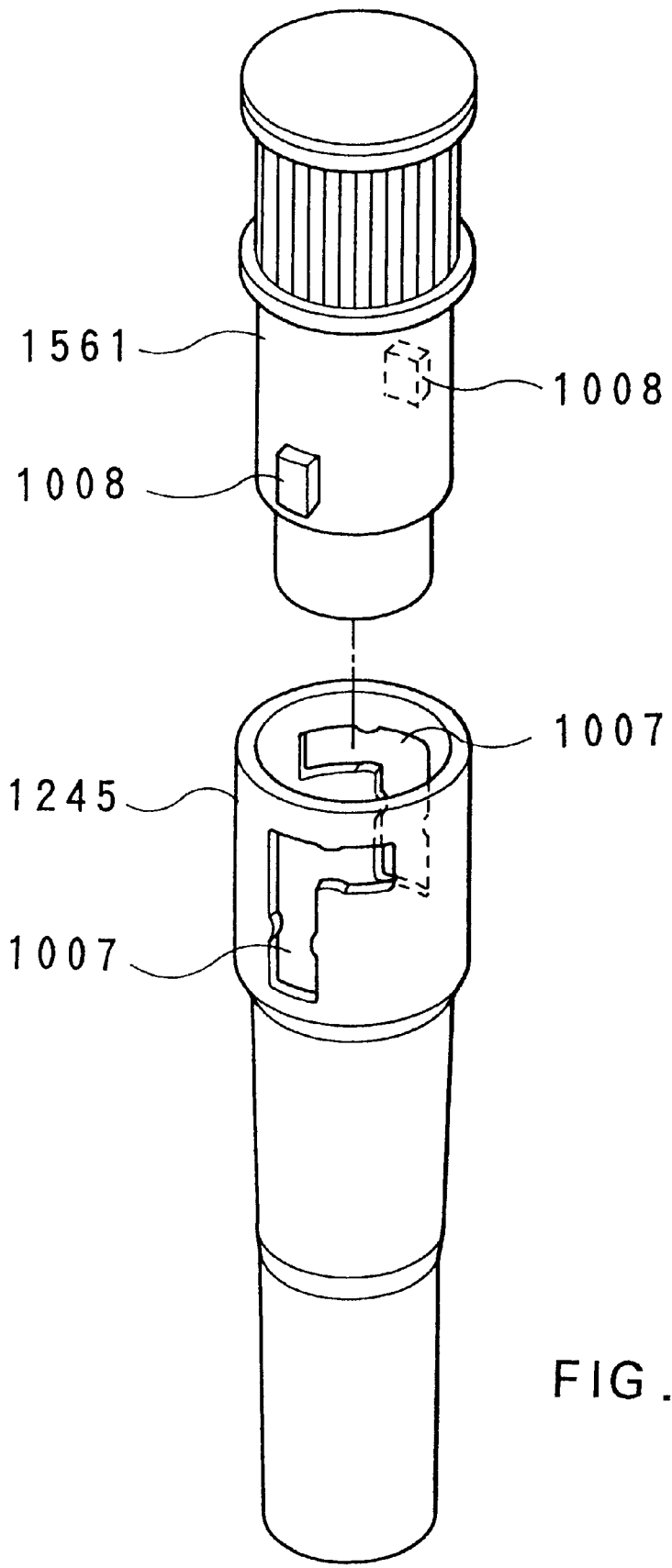
FIG. 58 illustrates perspectively the assembling of the parts 1561 and 1245 for the microorganism-detecting apparatus of FIG. 57.
Figure 59:
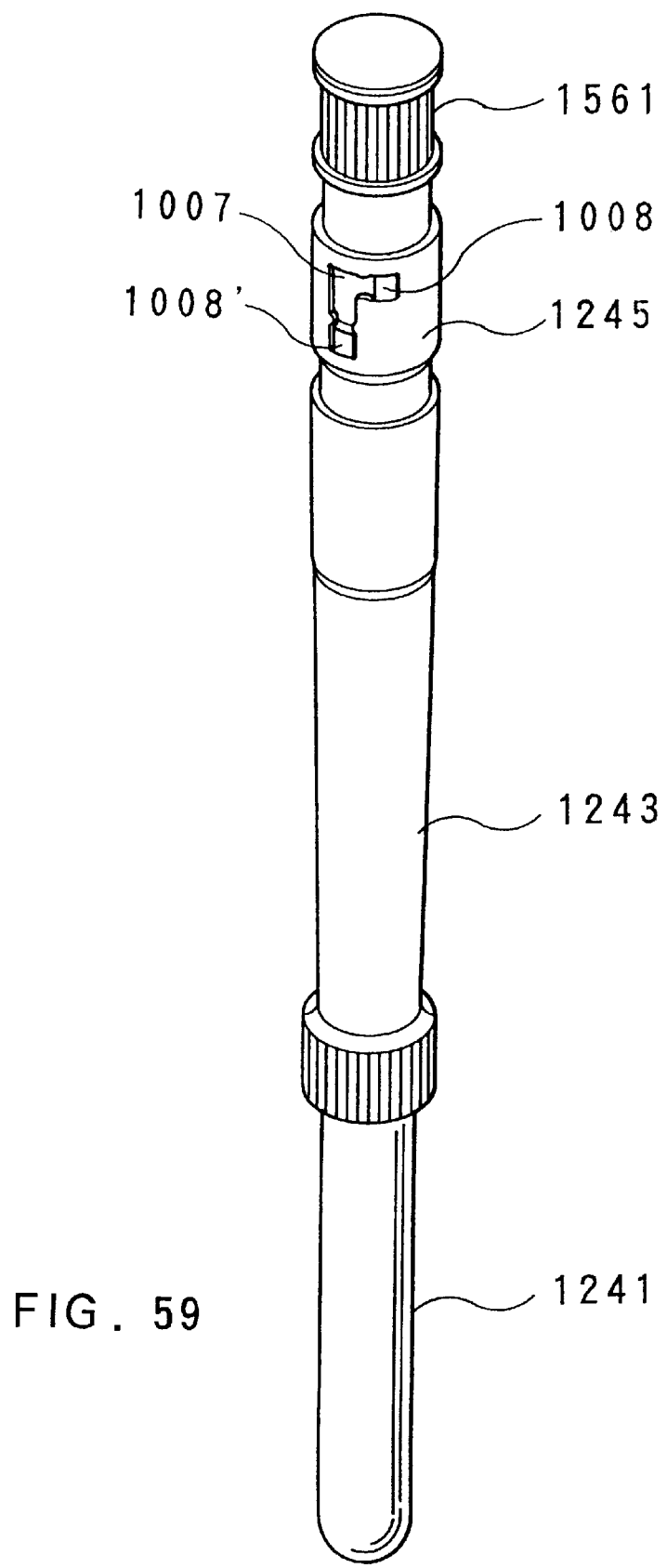
FIG. 59 is a perspective view of an embodiment of the microorganism-detecting apparatus according to the present invention.
Figure 70:
FIG. 70 illustrates various shapes for the guides (1004, 1007) for a protecting and engaging structure in an embodiment of the microorganism-detecting apparatus according to the present invention.

In FIGS. 53 and 57, a guide groove (guide space) (1004, 1007) is formed at two sites while the guide groove (guide space) is formed at one site in FIGS. 55 and 59. In FIG. 61, the member (1243) has two guide grooves (guide spaces) (1004); the member (1245) has two stoppers (1005) and two guide grooves (guide spaces) (1007); and the cap member (1561) has two stoppers (1008)). In FIG. 63, the member (1243) has one guide groove (guide space) (1004); the member (1245) has one stopper (1005) and one guide groove (guide space) (1007); and the cap member (1561) has one stopper (1008). One or optionally more guide grooves (guide spaces) can be formed in each member. Although, in the drawings, the guide portion (1004) is formed through the side wall of the member (1243), it is possible to form a shallow guide groove by reducing the inner side wall of the member (1243) so as to make it partially thin (by cutting the inner side wall thereof) without a through hole. In the drawings, the guide (1004) is formed in the side wall of the member (1243) and a stopper (1005) is formed on the side wall of the member (1245) at the engaging side with the member (1243). Alternatively, the guide (1004) may be formed in the side wall of the member (1245) and a stopper (1005) may also be formed on the side wall of the member (1243). Similarly, a guide portion (1007) and a stopper (1008) can be formed in the members. The shape of the guide groove (guide space) is not limited to but includes a L shape, those as illustrated in FIG. 70 and the like.

Figure 65:
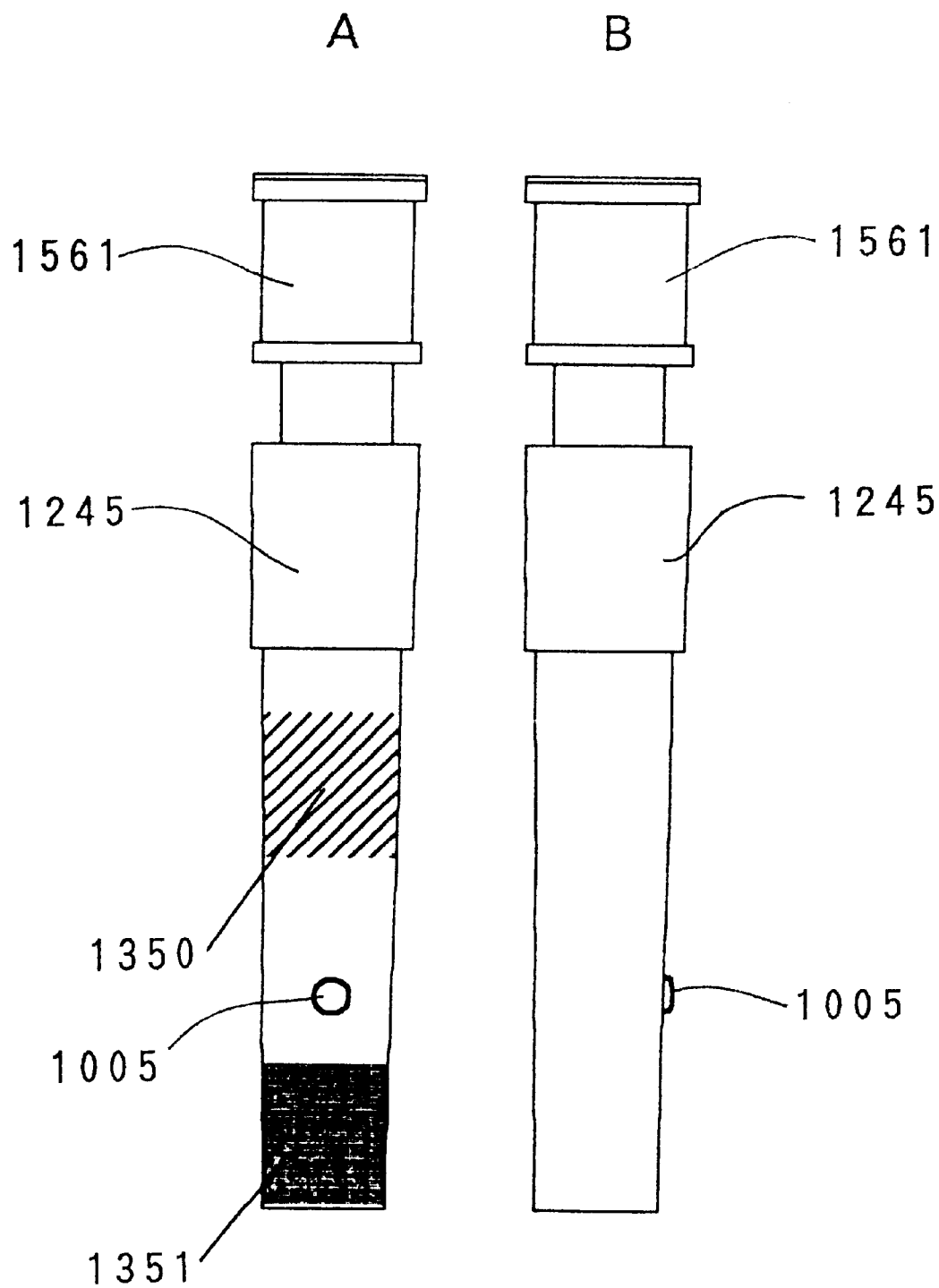
FIGS. 65A and 65B are views of the members (1561, 1245) for an embodiment of the microorganism-detecting apparatus according to the present invention (65A: front view and 65B: side view).
Figure 66:
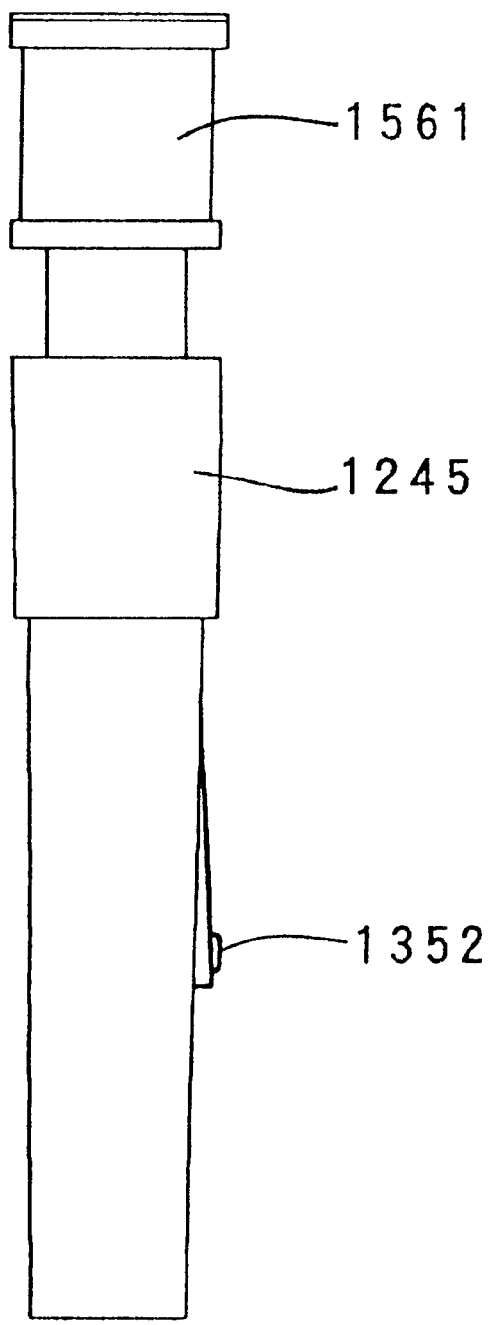
FIG. 66 is a side view of the members (1561, 1245) for an embodiment of the microorganism-detecting apparatus according to the present invention.
Figure 67:
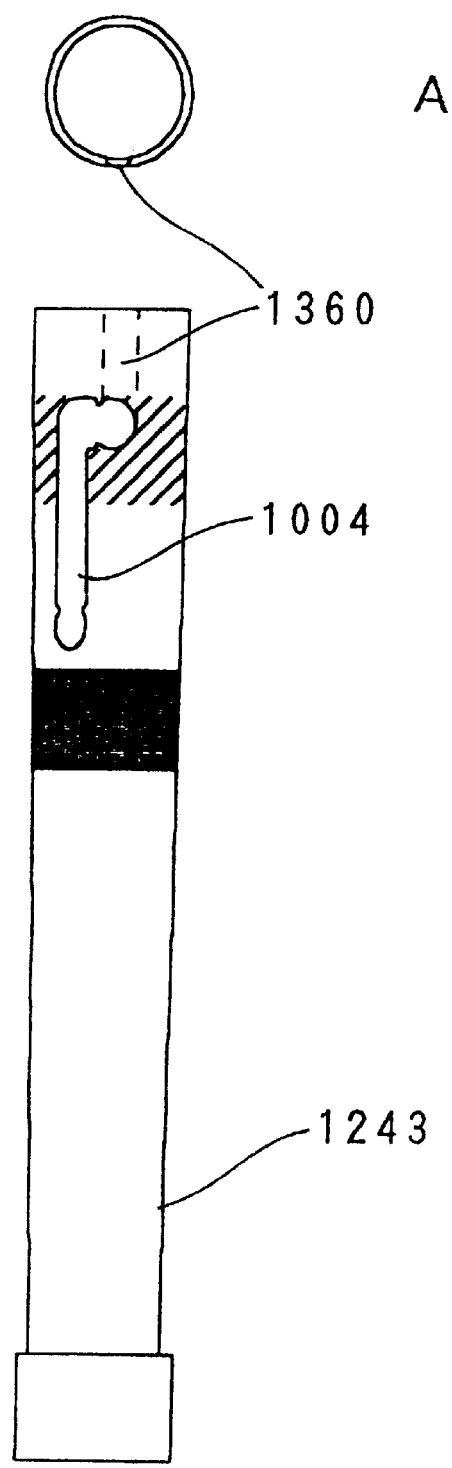
FIGS. 67A and 67B show schematically the member 1243 capable of engaging with the member (1245) as illustrated in FIG. 65 (67A: top view and 67B: front side view).
Figure 68:
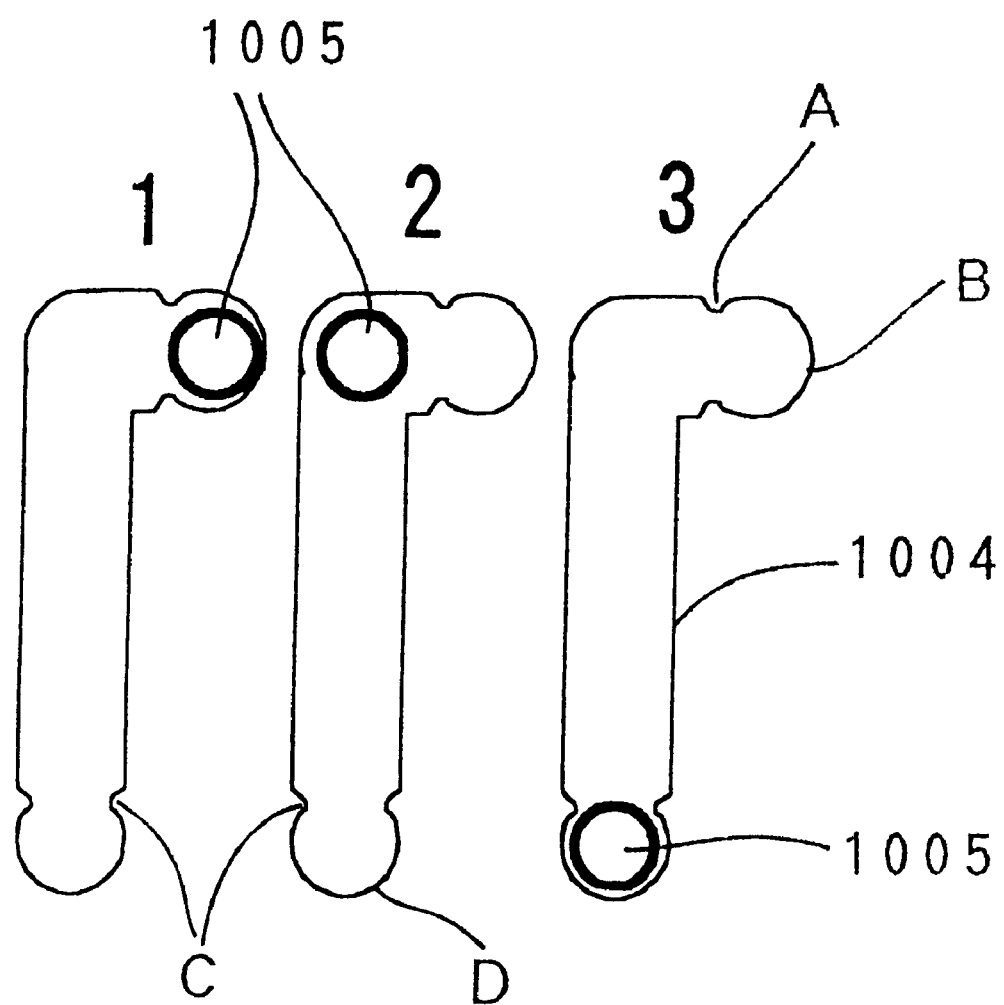
FIG. 68 is a schematic diagram for explaining the relationship between a guide portion (1004) and a stopper (1005) for an embodiment of the microorganism-detecting apparatus according to the present invention.
Figure 69:
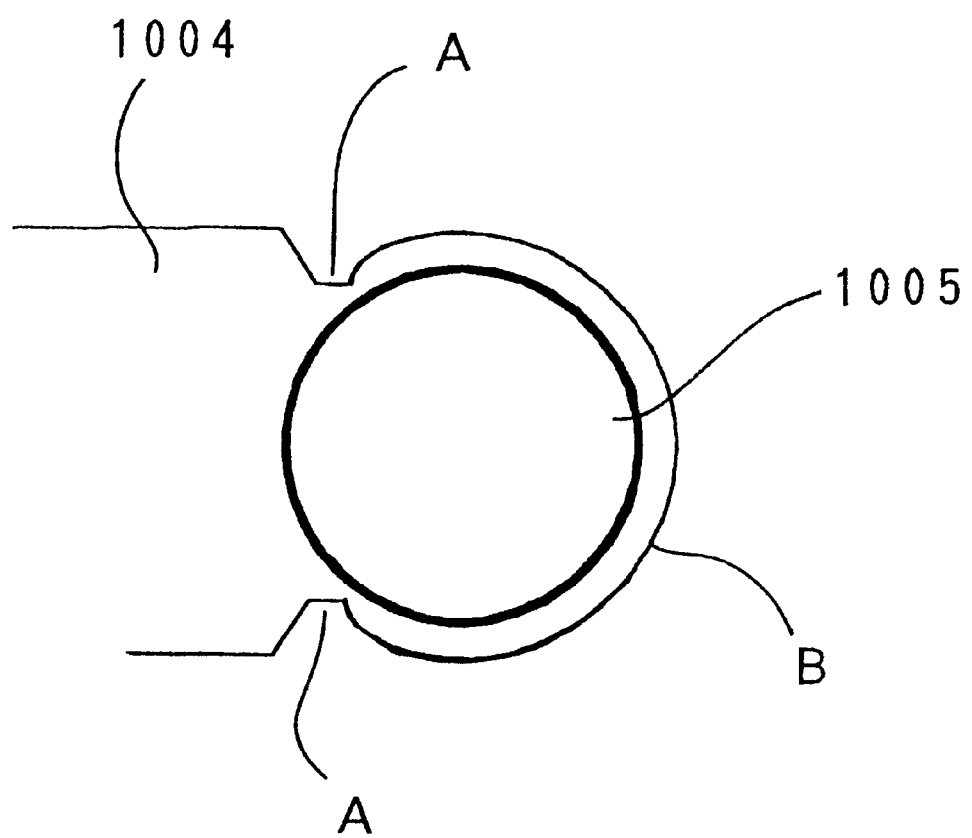
FIG. 69 illustrates schematically the enlarged engagement of a guide portion (1004) with a stopper (1005) at the site B for an embodiment of the microorganism-detecting apparatus according to the present invention.

FIG. 65 shows an appearance of the members (1561, 1245) in another representative embodiment of the microorganism-detecting apparatus according to the present invention. FIG. 66 shows an appearance of the members (1561, 1245) in another representative embodiment of the microorganism-detecting apparatus according to the present invention. FIG. 67 shows the member 1243 capable of engaging with the members (1245 (and 1561)) illustrated in FIG. 65. FIG. 68 is a schematic diagram for explaining the relationship between the guide portion (1004) and the stopper (1005). FIG. 69 is an enlarged partial view in connection with the relationship between the guide portion (1004) and the stopper (1005).

Prior to use of the microorganism-detecting apparatus according to the present invention, the member (1245) is engaged with the member (1243) (FIG. 54) and the stopper (1005) is positioned at the upper side of the guide (1004) (FIG. 53). Referring to FIG. 68, the stopper (1005) is located at the site B in FIG. 68-1.

Upon breaking the ampule (upon use thereof), the stopper (1005) is moved beyond a pawl portion (neck) (A) (FIG. 68-2 and FIG. 69) by turning the member (1245) whereby the member (1245) can be pushed into the member (1243). Thus, the stopper (1005) can be moved to the position (D) (In FIG. 53, it corresponds to the stopper (1005')). If necessary, a pawl portion (neck) (C) may be formed in order to fix the stopper (1005) (FIG. 68-3). In FIGS. 55 to 64, each apparatus has the same mechanism and action.

FIG. 65 shows an embodiment of the microorganism-detecting apparatus according to the present invention wherein a measure for securing the adhesion (sealing) between the member (1243) and the member (1245) is set at the surface region (1351) on the outer wall of the member (1245). The adhesion (sealing) may be achieved by various techniques including frosting of a surface, coating with rubber, etc. and the useful technique can be selected from those known to a person skilled in the art such as the field of container. Although FIG. 65 also shows the possibility that a measure for securing the adhesion between the member (1243) and the member (1245) will be made at the surface region (1350) on the outer wall of the member (1245), this measure is generally disposed at the surface region (1351) when the stopper (1005) -guide (1004) system is formed.

FIG. 67 shows an embodiment of the microorganism detecting apparatus according to the present invention wherein a measure for securing the adhesion between the members (deeply shadowed area) is installed on the inner wall of the member (1243) which corresponds to the surface region (1351) formed on the member (1245). Similarly to FIG. 65, FIG. 67 also show the possibility that a measure for securing the adhesion will be made on the slantingly lined area. In FIG. 67, a shallow groove (1360) is formed so as to facilitate an insertion of the stopper (1005) into the guide portion (1004).

In FIG. 66, the stopper (1352) has a structure capable of being flexibly pressed down against the outer wall side of the member (1245) upon insertion of the member (1245) into the member (1243). The stopper (1352) is movable inwardly and outwardly by a deflecting force. In addition, the mechanism required in keeping and carrying the apparatus without the breakage of (a) the ampule for a medium and (b) the ampule for a disinfectant may include an engagement of a convex portion formed on one member with a concave portion formed on another member for (i) the members (1245) and (1243) and for (ii) the members (1561) and (1245), a combination of a stopper removable from the detecting apparatus therewith. The mechanism may comprise a mark attached thereto, which indicates a position for fixing each member.

In accordance with the present invention, it has been found that it is possible to measure how many viable microorganism cells are present prior to an initiation of incubation, substantially in a closed system, such as the microorganism-detecting apparatus of the present invention. Utilization of the microorganism-detecting apparatus of the present invention enables a person to easily, securely and portably estimate the number of viable microorganism cells present in foods, cooking tools and the like. Accordingly, it is possible to estimate a degree of pollution quickly for various samples including cooking utensils, e.g. kitchen knife and chopping board, foods, and beverages or surroundings, by using the microorganism-detecting apparatus of the present invention. Through the use of the apparatus of the present invention, a person can easily, conveniently, securely and safely judge what kind or species of microorganism it is and/or determine the amount of microorganisms present.

The measurement of viable cells can be carried out by culturing the cell in a liquid medium contained in the apparatus of the present invention followed by measuring absorbance, turbidity, etc. for the medium without taking it out of the apparatus. The measurement may be carried out by a measuring instrument or machine, by visual observation including a comparison with a symbol mark and the like, or by a combination thereof. The visual observation may include a technique employing labels such as characters, lines, pictures and dots wherein a recognition degree is estimated. The label for recognition may be attached to or marked (painted) on a swab (microorganism-collecting member), an inner wall of the container receiving the medium for culturing cells, or an outer wall thereof. The label for recognition may be suitably selected in view of its shape, color, depth and lightness. For the quantitative measurement, it is preferred to avoid a pigment in a medium for culturing microorganisms. In the present measurement, it is possible to estimate the number of cells present at a starting point.

Incidentally, in FIG. 1 and in FIGS. 3 to 70, illustrations are made for concentrating an the characteristic points of the microorganism-detecting apparatus according to the present invention. It is to be understood that some of the details may be omitted there. Consequently, it is to be understood that the apparatus having the characteristic features of the apparatus according to the present invention shown in this specification, drawings, and the attached claims including those wherein various modifications are made and each of the constituting parts or members is connected each other in more detailed manner are also included in the coverage of the present invention.

Merit of the Invention

As mentioned hereinabove, the present invention provides a selective microorganism-detecting apparatus where certain microorganisms (particularly pathogenic ones and, more particularly, those for food poisoning) can be easily, securely and simply detected and/or identified. The apparatus can be expected to be stored for a long period and is in such a shape (arrangement) that it can be immediately used at any time when necessary and that it can be easily and conveniently carried. Thus, the present invention provides a selective microorganism-detecting apparatus which is especially suitable for private and domestic use where toxic microorganisms such as those for food poisoning can be easily, securely and simply detected/identified and, even after use, is able to be disposed safely, surely and easily.

The microorganism-detecting apparatus of the present invention can be very easily used privately and domestically and, therefore, it is now possible to detect the microorganism and also to establish a preventing measure against food poisoning by a self-active basis not performed by professionals such as those in public health centers. After incubation of the microorganism, the microorganism-detecting apparatus of the present invention is not made into an open system, for instance, by opening a cover. Even if a pathogenic microorganism is contained therein, therefore, it is easy to change the used apparatus to a disposable form and then to discard it. Moreover, there is no need that the apparatus used for incubation is opened and disinfected by adding a disinfectant to the microorganism-containing culture liquid with a tool such as a pipette. Accordingly, troublesome operations can be eliminated and there is no danger. No professional technique, skillfulness and apparatus is necessary to operate the apparatus of the present invention for detecting microorganisms. Further, in the microorganism-detecting apparatus of the present invention, it is unnecessary to prepare a disinfectant solution at all times separately from the container for incubation. Therefore, the apparatus is quite good in terms of portability and easy handling.

EXAMPLES

Described below are examples of the present invention which are provided only for illustrative purposes, and not to limit the scope of the present invention. In light of the present disclosure, it should be understood that numerous embodiments within the scope of the claims will be apparent to those of ordinary skill in the art.

Example 1

(Apparatus for Detection of *Staphylococcus aureus* and Preparation Thereof)

By referring to FIG. 5, the following materials were used to construct the microorganism-detecting apparatus having the following size:

Container (1): a hollow cylinder having a bottom (inner diameter: 8.5 mm; height: 150 mm) made of polyethylene (thickness: 0.6 mm)

Cover (2): a hollow cylinder having a bottom (inner diameter: 10 mm; length: 53 mm) made of polyethylene (thickness: 0.6 mm)

First bag-shaped member (4): a hollow cylinder having a bottom (inner diameter: 7.5 mm; length: 40 mm) made of glass (thickness: 0.5 mm)

Partition member (5): a disk-shaped body with a diameter of 6 mm made of polyethylene (thickness: 1 mm)

Rod-shaped element (6a): made of polyethylene; diameter: 2 mm; length: 135 mm

Microorganism-collecting end (6b): an end of "swab", made of absorbent cotton (diameter: 5 mm; length: 15 mm)

Disk member (7): filter paper (thickness: 1 mm; diameter: 6 mm)

The antibiotic substances as shown in Table 1 were impregnated in the disk member (7), located between the bottom of the container (1) and the microorganism-collecting end (6b) in such amounts that concentrations of 10 μg/ml of aztreonam, 8 μg/ml of polymyxin B and 5 μg/ml of fluconazole were obtained upon unification with the medium.

Medium (3): a medium having the composition as shown in Table 1 (except the antibiotics).

TABLE 1

| A) Screening Medium for Detection of *Staphylococcus aureus* (Modified Mannitol-Salt Medium) | |
|---|---|
| Myosate Peptone | 2.5 g |
| Polypeptone Peptone | 10.0 g |
| Yeast Extract | 2.5 g |
| D-Mannitol | 10.0 g |
| Lithium Chloride | 5.0 g |
| Sodium Chloride | 40.0 g |
| Phenol Red | 25 mg |
| Distilled Water | 1000 ml |
| pH 7.5 | |
| Sterilized by autoclaving at 115° C. for 15 minutes. | |
| Secondary Test: Disk for detection of phosphatase | |
| Disk:  Aztreonam | 1 to 15 μg/ml |
| Polymyxin B | 1 to 15 μg/ml |
| Fluconazole | 1 to 10 μg/ml |

After preparing a detecting apparatus for *Staphylococcus aureus* having the above composition, it was sterilized by irradiating with gamma-ray at 1 to 30° C. for one minute. The apparatus after the sterilization was stored in a bag made of polyethylene film (thickness: 100 μm) laminated with (vaporized) aluminum for shielding the light until immediately before use.

Example 2

(Detecting Apparatus for *Vibrio parahaemolyticus* and Preparation Thereof)

A detecting apparatus for detecting *Vibrio parahaemolyticus* was prepared, sterilized and stored by the same manner as in Example 1 with an exception that composition for the medium (3) and antibiotics were changed as shown below (Table 2) by referring to FIG. 5. At that time, the antibiotic substances as shown in Table 2 were impregnated in a disk material (7) in such amounts that concentrations of 10 μg/ml of polymyxin B, 5 μg/ml of fluconazole and 5 μg/ml of potassium tellurite were obtained upon unification with the medium.

TABLE 2

B) Screening Medium for Detection of *Vibrio parahaemolyticus*
(Modified Salt-Polymyxin Medium)

| | |
|---|---|
| Polypeptone Peptone | 10.0 g |
| Yeast Extract | 5.0 g |
| Sodium Chloride | 20.0 g |
| Saccharose | 15 g |
| Sodium dodecyl sulfate | 1.0 ml |
| Bromthymol Blue | 40.0 mg |
| Cresol Red | 40.0 mg |
| Distilled Water | 1000 ml |
| pH 7.2 | |
| Sterilized by autoclaving at 115° C. for 15 minutes. | |
| Secondary Test: Disk for detection of cytochrome oxidase | |
| Disk: Polymyxin B | 1 to 15 μg/ml |
| Fluconazole | 1 to 10 μg/ml |
| Potassium tellurite | 1 to 10 μg/ml |

Example 3

(Detecting Apparatus for Salmonella and Preparation Thereof)

A detecting apparatus for detecting Salmonella was prepared, sterilized and stored by the same manner as in Example 1 with an exception that composition for the medium (3) and antibiotics were changed as shown below (Table 3) by referring to FIG. 5. At that time, the antibiotic substances as shown in Table 3 were impregnated in a disk member (7) in such amounts that concentration of 5 μg/ml of fluconazole was obtained upon unification with the medium.

TABLE 3

C) Screening Medium for Detection of Salmonella
(Modified Xylose-Lysine Medium)

| | |
|---|---|
| Yeast Extract | 5.0 g |
| Sodium Chloride | 5.0 g |
| Saccharose | 5.0 g |
| Lactose | 5.0 g |
| Xylose | 4.0 g |
| Lysine | 10.0 g |
| Sodium dodecyl sulfate | 1.0 ml |
| 0.2% Bromocresol Purple | 12.0 ml |
| Ammonium Iron Citrate | 0.5 g |
| Sodium Thiosulfate Pentahydrate | 0.2 g |
| Distilled Water | 1000 ml |
| pH 6.8 | |
| Sterilized by autoclaving at 115° C. for 15 minutes. | |
| Disk: Fluconazole | 1 to 10 μg/ml |

Example 4

(Confirmation of Selectivity of a Detecting Medium for *Staphylococcus aureus*)

Selectivity of the medium for detecting *Staphylococcus aureus* prepared in Example 1 was confirmed to be as follows:

Twenty-two kinds of microorganisms as shown in the following Table 4 were dispersed in 1.5 ml of the medium for detecting *Staphylococcus aureus* prepared in Example 1 to make the concentration about $10^6$ cells/ml at the initiation of the incubation, cultured in air at 37° C. for 24, 48 or 72 hours and, out of the color change (if any) of Phenol Red (a pH indicator contained in the above medium), a judgment was made whether the growth of the microorganism was noted. When the color tone of the medium after the incubation turned yellow or red, the conclusion was done as "positive (+)" (growth of the microorganism was noted) or "negative (−)" (growth of the microorganism was not noted), respectively.

TABLE 4

A) Modified Mannitol Salt Base Medium (Grain-Positive Cocci and Grain-Negative Cocci)

| Gram Positive/ Antibiotics | | S. aureus 209P | S. aureus TEN | S. aureus 003 | S agal-actiae | S. pyo-genes | S. epider-midis 2 | S. epider-midis 5 | S. sapro-phyticus | S. haemo-lyticus | E. faeca-lis 18 | E. faeca-lis 7862 |
|---|---|---|---|---|---|---|---|---|---|---|---|---|
| Aztreonam 10 μg/ml + | 24 hr | + | + | + | − | − | − | − | + | + | − | − |
| Polymyxin B 8 μg/ml + | 48 hr | + | + | + | − | − | − | − | + | + | − | − |
| Fluconazole 5 μg/ml | 72 hr | + | + | + | − | − | − | − | + | + | − | + |
| Gram Negative/ Antibiotics | | Salmo-nella | Serratia | Entero-bacter | Shigella | Escher-ichia | Kleb-siella | Proteus 1 | Proteus 19 | Proteus 20 | Pseudo-monas 1 | Pseudo-monas 2 |
| Aztreonam 10 μg/ml + | 24 hr | − | − | − | − | − | − | − | − | − | − | − |
| Polymyxin B 8 μg/ml + | 48 hr | − | − | − | − | − | − | − | − | − | − | − |
| Fluconazole 5 μg/ml | 72 hr | − | − | − | − | − | − | − | − | − | − | − |

Positive (+): Color of the medium turned yellow;
Negative (−): Color of the medium turned red The result is as shown in Table 4. It is clear from the result of Table 4 that, when the medium for detecting *Staphylococcus aureus* of the present invention was used, proliferation of Gram-negative microorganism and Eumycetes was effectively inhibited by antibiotic and antifungal substances adsorbed with said medium (3) and said disk (7).

in the above medium), a judgment was made whether the growth of the microorganism was noted. When the color tone of the medium after the incubation turned yellow or green, the conclusion was done as "positive (+)" (growth of the microorganism was noted) or "negative (−)" (growth of the microorganism was not noted), respectively.

TABLE 5

B) Modified Polymyxin Salt Base Medium (Gram-Positive Cocci and Gram-Negative Cocci)

| Gram Positive/ Antibiotics | | S. aureus 209P | S. aureus TEN | S. aureus 003 | S agal-actiae | S. pyo-genes | S. epider-midis 2 | S. epider-midis 5 | S. sapro-phyticus | S. haemo-lyticus | E. faeca-lis 18 | E. faeca-lis 7862 |
|---|---|---|---|---|---|---|---|---|---|---|---|---|
| Polymyxin B 10 μg/ml + | 24 hr | − | − | − | − | − | − | − | − | − | − | − |
| Fluconazole 5 μg/ml + | 48 hr | − | − | − | − | − | − | − | − | − | − | − |
| Potassium Tellurite | 72 hr | − | − | − | − | − | − | − | − | − | − | − |

| Gram Negative/ Antibiotics | | Salmonella | Serratia | Enterobacter | Shigella | Escherichia | Klebsiella | Proteus 1 | Proteus 19 | Proteus 20 | Pseudomonas 1 | Pseudomonas 2 |
|---|---|---|---|---|---|---|---|---|---|---|---|---|
| Polymyxin B 10 μg/ml + | 24 hr | − | − | − | − | − | − | − | + | + | − | − |
| Fluconazole 5 μg/ml + | 48 hr | − | − | − | − | − | − | + | + | + | − | − |
| Potassium Tellurite | 72 hr | − | − | − | − | − | − | + | + | + | − | − |

Positive (+): Color of the medium turned yellow;
Negative (−): Color of the medium turned green Among the microorganisms tested hereinabove, *S. epidermidis* did not decompose mannitol contained in the medium (3) and, therefore, there was no change in the color tone of the medium.

According to the experiments conducted by the present inventors, it was found that there were some microorganisms other than *Staphylococcus aureus* which were "positive" in this medium and that they were coagulase-negative Staphylococcus (CNS), *E. faecalis*, *E. faecium*, etc. However, those microorganisms were able to be discriminated from *Staphylococcus aureus* by a phosphatase test or by a coagulase test (cf. "Directions for Hygienic Tests: Staphylococcus").

In a phosphatase test, incubation was conducted by the above-mentioned medium using a disk for detection of phosphatase (filter paper adsorbed with 4-methylumbelliferyl phosphoric acid) and, after that, fluorescence of 4-methylumbelliferone was detected by irradiating with ultraviolet ray (366 nm) whereby its presence was able to be confirmed.

Example 5
(Confirmation of Selectivity of a Detecting Medium for *Vibrio parahaemolyticus*)

Selectivity of the medium for detecting *Vibrio parahaemolyticus* prepared in Example 2 was confirmed to be as follows:

Twenty-two kinds of microorganisms as shown in the following Table 5 were dispersed in 1.5 ml of the medium for detecting *Vibrio parahaemolyticus* prepared in Example 2 to make the concentration about $10^6$ cells/ml at the initiation of the incubation, cultured in air at 37° C. for 24, 48 or 72 hours and, out of the color change (if any) of Bromthymol Blue and Cresol Red (pH indicators contained The result is as shown in Table 5. It is clear from the result of Table 5 that, when the medium for detecting *Vibrio parahaemolyticus* of the present invention was used, growth of Gram-positive microorganisms was inhibited by antibiotic substances while that of Gram-negative microorganism and most of Eumycetes were effectively inhibited by antibiotic substances (polymyxin B, fluconazole and potassium tellurite) adsorbed with said disk (7).

According to the experiments conducted by the present inventors, it was found that there were some microorganisms other than *Vibrio parahaemolyticus* which were "positive" in this medium and that they were *V. cholerae*, *V. vulnificus*, Proteus spp., etc. However, those microorganisms were able to be discriminated from *Vibrio parahaemolyticus* by an oxidase test (a cytochrome oxidase reaction; cf. Kovacs: Nature (London), 178, 703 (1956)).

Example 6
(Confirmation of Selectivity of a Detecting Medium for Salmonella)

Selectivity of the medium for detecting Salmonella prepared in Example 3 was confirmed to be as follows:

Twenty-two kinds of microorganisms as shown in the following Table 6 were dispersed in 1.5 ml of the medium for detecting Salmonella prepared in Example 3 to make the concentration about $10^6$ cells/ml at the initiation of the incubation, cultured in air at 37° C. for 24, 48 or 72 hours and, out of the color change (if any) of Bromcresol Purple (a pH indicator contained in the above medium), a judgment was made whether the growth of the microorganism was noted. When the color tone of the medium after the incubation turned "black" or "purple or yellow", the conclusion was done as "positive (+)" (growth of the microorganism was noted) or "negative (−)" (growth of the microorganism was not noted), respectively. Hydrogen sulfide-producing microorganisms such as Salmonella changed the color of the medium to black by the reaction of thiosulfate contained in the medium with ammonium iron citrate.

ber (4) was made to fall down into the container. As a result, the microorganism-collecting end (6b) in the the microorganism-collecting part (6) dipped into the medium (3) (it was possible to prevent the stuffs other than the

TABLE 6

C) Modified Xylose-Lysine Base Medium (Grain-Positive Cocci and Gram-Negative Cocci)

| Gram Positive/<br>Antibiotics | | S. aureus<br>209P | S. aureus<br>TEN | S. aureus<br>003 | S agal-<br>actiae | S. pyo-<br>genes | S. epider-<br>midis 2 | S. epider-<br>midis 5 | S. sapro-<br>phyticus | S. haemo-<br>lyticus | E. faeca-<br>lis 18 | E. faeca-<br>lis 7862 |
|---|---|---|---|---|---|---|---|---|---|---|---|---|
| Fluconazole | 24 hr | − | − | − | − | − | − | − | − | − | − | − |
| 5 μg/ml | 48 hr | − | − | − | − | − | − | − | − | − | − | − |
| | 72 hr | − | − | − | − | − | − | − | − | − | − | − |
| Gram Negative/<br>Antibiotics | | Salmo-<br>nella | Serratia | Entero-<br>bacter | Shigella | Escher-<br>ichia | Kleb-<br>siella | Proteus<br>1 | Proteus<br>19 | Proteus<br>20 | Pseudo-<br>monas 1 | Pseudo-<br>monas 2 |
| Fluconazole | 24 hr | + | − | − | − | − | − | − | − | − | − | − |
| 5 μg/ml | 48 hr | + | − | − | − | − | − | − | − | − | − | − |
| | 72 hr | + | − | − | − | − | − | + | − | − | − | − |

Escherichia coli  
Citrobacter spp  
Kiebsiella spp } color of the medium: yellow  
Enterobacter spp  
Proteus spp Shigella spp  
Serratia spp } color of the medium: purple  
Pseudomonas spp Positive (+): Color of the medium turned yellow;  
Negative (−): Color of the medium turned purple or yellow  
Salmonella . . . color of the medium: black The result is as shown in Table 6. It is clear from the result of Table 6 that, when the medium for detecting Salmonella of the present invention was used, growth of Gram-positive microorganisms was inhibited by the antibiotic substances while that of Eumycetes was effectively inhibited by the antibiotic substances (fluconazole) adsorbed with said disk (7).

According to the experiments conducted by the present inventors, it was found that there were some Gram-negative microorganisms changed the color tone of this medium from purple to yellow. Examples of such a color change were as follows:

Microorganism which changed the color to black color: Salmonella;

Microorganisms which changed the color to yellow: Escherichia coli, Citrobacter spp., Klebsiella spp., Enterobacter spp. and Proteus spp.; and Microorganisms which changed the color to purple: Shigella spp., Serratia spp. and Pseudomonas spp.

Example 7

(Use of the Apparatus for Detecting Staphylococcus aureus)

A bag for the apparatus for detecting Staphylococcus aureus prepared in Example 1 was broken to take out said apparatus, then a cover (2) (and a microorganism-collecting part (6)) were taken out from the apparatus (cf. FIG. 2(a)) and the microorganism-collecting end (6b) was rubbed for several times against the surface of a cooking device (such as a chopping board) (cf. FIG. 2(b)).

After that, the above cover (2) was inserted into the apparatus again, the microorganism-collecting end (6b) was kept at a predetermined position in the container, the first bag-shaped member (4) was broken by strongly compressing from outside of the cover (2) using a compressing device ("a breaking device" in a broad clip-like shape) (not shown) and the medium (3) enclosed in said first bag-shaped memmedium (such as broken pieces of the first bag-shaped member (4)) from falling-down into the container).

Incubation was then conducted at 37° C. for 16 to 24 hours in such a state that the microorganism-collecting end (6b) of the microorganism-collecting part (6) was dipped in a medium (3) whereupon the color tone of the medium (3) changed from red to yellow in some of the cooking device (chopping board). Thus, the presence of Staphylococcus aureus was confirmed. The cooking device where the presence of Staphylococcus aureus was confirmed as such was wiped for several times with a gauze moisturized with a 0.2 to 0.5% aqueous chlorohexidine solution ("Hibiden" (trade name); manufactured by SUMITOMO PHARMACEUTICALS CO. LTD., Japan) followed by washing for ten minutes with tap water. The cooking device (chopping board) which was treated by cleaning with invert soap and washing with water as such was subjected to a test for detecting Staphylococcus aureus as same as above whereupon the color tone of the medium (3) was unchanged but was still in yellow.

This meant that no Staphylococcus aureus was detected. Thus, it was confirmed that Staphylococcus aureus could be effectively removed by the above-mentioned disinfecting treatment.

(Disinfecting/Sterilizing Treatment in the Used Apparatus for Detecting Staphylococcus aureus)

The second bag-shaped member (8) was broken by strongly compressing its cover (2) from outside using a compressing device (a "breaking device" in a broad clip-shaped one) (not shown) whereby a disinfectant/sterilizer (9) (a 5 to 10% aqueous solution of chlorohexidine (trade name: "Hibiden"; manufactured by SUMITOMO PHARMACEUTICALS CO. LTD., Japan)) enclosed in said second bag-shaped member (8) was released down into the container. As a result, it is now possible that a disinfecting/sterilizing treatment of the inner side of the container (1) including the medium is conducted without detaching the cover (2) from the container (1).

Example 8

(Use of Apparatus for Detecting *Vibrio parahaemolyticus* and Salmonella)

The same operation as in Example 7 was conducted except that the apparatuses for detecting *Vibrio parahaemolyticus* and for Salmonella prepared in Examples 2 and 3, respectively, were used to confirm the presence of food poisoning microorganism in cooking devices whereupon, in some cooking devices, presence of *Vibrio parahaemolyticus* or Salmonella was confirmed.

When those cooking devices were wiped with invert soap and washed with water by the same manner as in Example 7, the presence of *Vibrio parahaemolyticus* and Salmonella was not noted after said disinfecting treatment. Thus, it was now confirmed that *Vibrio parahaemolyticus* or Salmonella could be effectively removed by the above-mentioned disinfecting treatment.

(Disinfecting/Sterilizing Treatment of Used Apparatus for Detecting *Vibrio parahaemolyticus* and Salmonella)

The second bag-shaped member (8) was broken by strongly compressing its cover (2) from outside using a compressing device (a "breaking device" in a broad clip-shaped one) (not shown) whereby a disinfectant/sterilizer (9) (a 5 to 10% aqueous solution of chlorohexidine (trade name: "Hibiden"; manufactured by SUMITOMO PHARMACEUTICALS CO. LTD., Japan)) enclosed in said second bag-shaped member (8) was released down into the container. As a result, it is now possible that a disinfecting/sterilizing treatment of inner side of the container (1) including the medium is conducted without detaching the cover (2) from the container (1).

Example 9

The same operation as in Example 7 was conducted for confirming the presence of food poisoning microorganism in cooking devices except that the detecting apparatuses having basic structures as shown in FIGS. 12 to 16 were used and that the screening media for *Staphylococcus aureus,* for *Vibrio parahaemolyticus* and for Salmonella mentioned in Examples 1, 2 and 3, respectively, and the antibiotic substances mentioned therein were jointly used whereupon, in some cooking devices, presence of *Staphylococcus aureus, Vibrio parahaemolyticus* or Salmonella was confirmed.

When those cooking devices were wiped with invert soap and washed with water by the same manner as in Example 7, the presence of *Staphylococcus aureus, Vibrio parahaemolyticus* and Salmonella was not noted after said disinfecting treatment. Thus, it was now confirmed that *Staphylococcus aureus, Vibrio parahaemolyticus* or Salmonella could be effectively removed by the above-mentioned disinfecting treatment.

(Disinfecting/Sterilizing Treatment of the Used Detecting Apparatus)

The second bag-shaped members (48, 64 (or 68), 88, 108) were broken by strongly compressing their covers (42, 62, 82, 102) from outside using a breaking function of the apparatus as shown in FIGS. 12 to 16 (such as 49, 461, 56, 53; 73, 74, 77; 93; 113) whereby a disinfectant/sterilizer (9) (a 5 to 10% aqueous solution of chlorohexidine (trade name: "Hibiden"; manufactured by SUMITOMO PHARMACEUTICALS CO. LTD., Japan)) enclosed in said second bag-shaped members (48, 64 (or 68), 88, 108) was fallen down into the container. As a result, it is now possible that a disinfecting/sterilizing treatment of the inner side of the container (41, 61, 81, 101) including the medium is conducted without detaching the cover (42, 62, 82, 102) from the container (41, 61, 81, 101).

Example 10

By referring to FIGS. 17 to 33, the following materials were used to construct the microorganism-detecting apparatus having the following size:

Thus, the size from the bottom of the container (241) of the microorganism-detecting apparatus shown by FIGS. 17 and 18 to the top of a cap member (249) thereof (i.e. length of the microorganism-detecting apparatus) was about 201 mm.

Container (241): a hollow cylinder having a bottom (inner diameter: about 9.0 mm; height: about 73 mm) made of polypropylene (thickness: about 1.0 mm) (At the outside near the opening, there were screw threads for connection.)

Rod-shaped part (member) (246): made of polypropylene; diameter: about 2.5 mm; length: about 77 mm Microorganism-collecting end (246b): made of absorbent cotton; an end of "swab" having a maximum diameter of about 5 mm and a length of about 15 mm Cover (243): The hollow cylindrical body (inner diameter: about 13.0 mm; length: about 96 mm; length of the engaging portion (259): about 10 mm) was made of polypropylene (thickness: about 1.0 mm). Inner side of the connecting part (259) had screw threads.

Partition member (296): a disk with a diameter of about 13 mm made of polypropylene (thickness: about 1 mm). At its center a connecting structure for a rod-shaped member of the microorganism-collecting part was placed. There were four perforated holes (through holes) in a shape of a fan. The partition member (296) was engaged with the connecting part (259) of the cover (243).

Cover (247): This (inner diameter: about 10 mm; length: about 57 mm; length of the head (245) (a connecting part with a cap (249)): about 13 mm) was made of polypropylene (thickness: about 1 mm). Inner side of the connecting part had screw threads. Ridge (or protruding portion) (297) placed on the inner side of the cover (243) (the protruding portion ranges to a protrusion (252)) and the groove (299) located at the outside of the cover (247) were made in such a manner that they were engaged (or geared) each other whereby, when the cover (247) was inserted into the cover (243), they were tightly joined.

Partition member (235): This was made of polypropylene (thickness: about 1 mm) and its diameter was about 9 mm. There were four perforated holes (through holes) in a shape of a fan. The partition member (235) was engaged with an end of the side of the container (241) of the cover (247).

Cap material (249): made of polypropylene (thickness: about 1 mm). Diameter of the top side (561) which was opposite to the container (241) was about 15 mm. A cover (562) for a cap member was engaged therewith where diameter of the screw thread (257) was about 11 to 13 mm and diameter of the bottom (256) at the side of the container (241) was about 9 mm. The screw threads (257) engaged with the grooves made inside of said connecting part (245). The screw threads formed at the inside of said connecting part (245) had a sufficient width (length of an axial direction of the cover (247)) so that the cap member (249) was able to be rotated and pushed thereinto.

First bag-shaped member (244): an ampule (inner diameter: about 9 mm; length: about 43 mm) made of glass (thickness: about 0.5 mm). It received, for example, the improved media as shown in Example 11 mentioned later and was made into an apparatus for detecting *Staphylococcus aureus, Vibrio parahaemolyticus,* Salmonella or *Escherichia coli* accordingly.

Second bag-shaped member (248): An ampule made of glass (thickness; about 0.5 mm) having inner diameter of about 9 mm and length of about 36 mm and receiving a disinfectant/bactericide as shown in Example 7 therein.

After manufacturing the microorganism-detecting apparatus having the above-mentioned constitution, it was sterilized by a sterilizer using ethylene oxide. The sterilization was conducted, for example, at the temperature of 30 to 50° C. in a gas consisting of about 20% of ethylene oxide and about 80% of carbon dioxide gas under the pressure of about 0.3 kg/m² for about five hours. The apparatus after the sterilization was placed in a bag made of polyethylene film (thickness: about 100 μm) evaporated with aluminum for shielding the light and stored until immediate before use. A medium of the following Example 11 was used by placing into the above-mentioned ampule (the first bag-shaped material (244)) followed by sealing.

Similarly were prepared the microorganism-detecting apparatuses by referring to FIGS. 34 to 51.

Example 11
(Preparation of a Microorganism-Detecting Apparatus Using Improved Medium)

(i) For a purpose of taking out from an ampule, a liquid medium is suitable and, from such a viewpoint, an improvement in media was conducted. Further, with an object of improving the specificity to the microorganism and of improving the operability of the microorganism-detecting apparatus, the composition for the medium was investigated whereby there will be no need of using a disk member (7) holding the antibiotics and an improvement was conducted for giving a selectivity to the medium. At the same time, investigation was made on pH indicators as well for such an improvement. As a result, the media having the following compositions were found to be appropriate:

(a) Improved Medium for Salmonella (1) Composition

| Base Medium: | |
| --- | --- |
| Tryptone (DIFCO) | 5 g |
| Yeast extract (DIFCO) | 3 g |
| L-(+)-Lysine monohydrochloride (WAKO; special grade) | 10 g |
| Glucose (anhydrous) (WAKO; special grade) | 1 g |
| Sodium chloride (WAKO; special grade) | 8 g |
| Monopotassium dihydrogen phosphate (WAKO; sp gr) | 1.6 g |
| Sodium thiosulfate pentahydrate (WAKO; special gr) | 0.2 g |
| Ammonium iron(III) citrate (brown) (WAKO; extra pure gr) | 0.3 g |
| Magnesium chloride hexahydrate (WAKO; special gr) | 20.3 g |
| Bromcresol Purple (WAKO; special grade) | 0.02 g |
| 0.4% Malachite Green solution | 30 ml |
| (Malachite Green oxalate (WAKO; special grade) was added to a small amount of pure alcohol, the mixture was well ground and pure water was added thereto to make the total volume 100 ml) | (0.4 g) |

(2) Method of Preparation

Each of the components in the above basic medium was weighed and 1000 ml of pure water was added thereto followed by well shaking and the resulting homogeneous floating liquid was mixed with 30 ml of a 0.4% Malachite Green solution followed by dissolving with heating (at 100° C. for 20 minutes). The medium was adjusted to pH 5.3 to 5.7. After cooling, the medium was filtered through a filter of 0.2μ.

(b) Improved Medium for *Vibrio parahaemolyticus*

| Base Medium: | |
| --- | --- |
| Salt-polymyxin broth (NISSUI SEIYAKU) | 33 g |
| D-(-)-Mannitol (WAKO; special grade) | 20 g |
| Sodium citrate dihydrate (WAKO; special grade) | 8 g |
| Sodium thiosulfate pentahydrate (WAKO; special gr) | 0.2 g |
| Bromocresol Purple (WAKO; special grade) | 0.02 g |

(2) Method of Preparation

Each of the components for the above basic medium was weighed and 1000 ml of pure water was added thereto followed by well shaking to prepare a homogeneous floating liquid. The medium was adjusted to pH 7.0 to 7.4 and sterilized at 121° C. for 15 minutes. Immediately after sterilization, it was cooled rapidly.

(c) Improved Medium for *Escherichia coli* Group

| Base Medium: | |
| --- | --- |
| Lauryl tryptose broth (DIFCO) | 35.6 g |
| Lactose monohydrate (WAKO; special grade) | 5 g |
| Bromthymol Blue (WAKO; special grade) | 0.04 g |

(2) Method of Preparation

Each of the components for the above basic medium was weighed and 1000 ml of pure water was added thereto followed by well shaking to prepare a homogeneous floating liquid. The medium was adjusted to pH 6.75 to 7.25 and sterilized at 121° C. for 15 minutes. Immediately after sterilization, it was cooled rapidly.

(d) Improved Medium for Staphylococci

| Basic Medium: | |
| --- | --- |
| Tryptone (DIFCO) | 10 g |
| Yeast extract (DIFCO) | 5 g |
| D-(-)-Mannitol (WAKO; special grade) | 10 g |
| Dipotassium monohydrogen phosphate (WAKO; sp gr) | 5 g |
| Lithium chloride monohydrate (WAKO; special grade) | 5.5 g |
| Glycine (WAKO; special grade) | 16.5 g |
| Sodium pyruvate (WAKO; special grade) | 12 g |
| Phenol Red (WAKO; special grade) | 0.025 g |
| 1% Aqueous solution of potassium tellurite | 15 ml |
| Potassium tellurite (WAKO) | 1 g |
| (Pure water (100 ml) was added to 1 g of potassium tellurite and the mixture was dissolved) | |

(2) Method of Preparation

Each of the components in the above basic medium was weighed and 1000 ml of pure water was added thereto followed by well shaking to prepare a homogeneous floating liquid. The medium was adjusted to pH 7.25 to 7.75 and sterilized at 121° C. for 15 minutes. When it was cooled down to 50° C. or lower, 15 ml of 1% aqueous solution of potassium tellurite was added. After well mixing, the mixture was sterilized by filtering through a filter of 0.2μ.

(ii) Measurement of Microorganism-Detecting Sensitivity and Specificity for Microorganism of Each Medium Control strains, i.e. Salmonella (amount: $10^9$ cells), *Vibrio parahaemolyticus* (amount: $10^9$), *Escherichia coli* group (amount: $10^9$) and Staphylococcus (amount: $10^8$), were dispersed in 1.5 ml of each medium to make the initial amount as shown in Tables 8 to 11 followed by incubating at 37° C. for 24 hours in air.

Growth of each microorganism was judged by means of changes in color after the incubation. Incidentally, all of the above-mentioned control stains were the clinically separated strains and were identified by API 20 E (trade name; bioMerieux-Vitek Japan, Ltd., Japan) for *Escherichia coli*, Salmonella and Vibrio and by API Staph (trade name; bioMerieux-Vitek Japan, Ltd., Japan) for Staphylococcus.

In API 20 E (trade name; bioMerieux-Vitek Japan, Ltd., Japan), the following is exemplified in a positive rate table under the incubating conditions of 35 to 37° C. for 24 or 48 hours:

They are *Escherichia coli* 1 and *Escherichia coli* 2 for *Escherichia coli*; *Salmonella arizonae*, *Salmonella choleraesuis*, *Salmonella paratyphi* A, *Salmonella* spp. and *Salmonella typhi* for Salmonella; and *Vibrio alginolyticus*, *Vibrio cholerae*, *Vibrio hollisae*, *Vibrio metschnikovii*, *Vibrio mimicus*, *Vibrio parahaemolyticus* and *Vibrio vulnificus* for Vibrio.

In API Staph (trade name; bioMerieux-Vitek Japan, Japan), the following is exemplified in a positive rate table under incubating condition of 35 to 37° C. for 18 to 24 hours for Staphylococcus:

They are *Staphylococcus aureus*, *Staphylococcus auriculans*, *Staphylococcus capitis*, *Staphylococcus caprae*, *Staphylococcus carnosus*, *Staphylococcus chromogenes*, *Staphylococcus cohnii*, *Staphylococcus epidermidis*, *Staphylococcus haemolyticus*, *Staphylococcus hominis*, *Staphylococcus hyicus*, *Staphylococcus lentus*, *Staphylococcus lugdunensis*, *Staphylococcus saprophyticus*, *Staphylococcus schleiferi*, *Staphylococcus sciuri*, *Staphylococcus simulans*, *Staphylococcus warneri* and *Staphylococcus xylosus*.

TABLE 7

(unit: CFU/ml)

| Microorganism-Detecting Apparatus | Sensitivity | |
|---|---|---|
| | Before Improvement | After Improvement |
| Kit for Staphylococcus | $3.0 \times 10^3$ | $1.9 \times 10^2$ |
| Kit for Salmonella | $3.0 \times 10^4$ | $1.4 \times 10^2$ |
| Kit for *Vibrio parahaemolyticus* | $3.0 \times 10^5$ | $3.1 \times 10^2$ |
| Kit for *Escherichia coli* group | $3.0 \times 10^4$ | $1.5 \times 10^2$ |

It is understood from Table 7 that, in the improved media, improvement in sensitivity was achieved in all microorganisms. A significant improvement was achieved especially in *Vibrio parahaemolyticus*. The following Tables 8 to 11 show the result of judgment of each of the media for the improved ones having the above-mentioned compositions as compared with the media before the improvement. In the tables, "Food Stamp" is a conventional name for a device for detecting microorganisms, for example, available from EIKEN KIZAI CO., LTD., Japan (trade name: "PETAN CHECK"), DENKA SEIKEN K. K., Japan (trade name: "DD CHECKER "SEIKEN"") and NISSUI PHARMACEUTICAL CO., LTD (trade name: "SHOKUZAI CHECK "NISSUI""), and "San Coli" is a trade name for "Coli forms Detection Paper" available from SAN KAGAKU K. K., Japan.

TABLE 8

Kit for Staphylococcus

| | Rate : 10 x | −3 | −4 | −5 | −6 | −7 | −8 |
|---|---|---|---|---|---|---|---|
| Dilution | Amount of Microorganism | $10^5$ | $10^4$ | $10^3$ | $10^2$ | $10^1$ | $10^0$ |
| Media before Improvement | Change in Color | (+) | (+) | (+) | (±) | (−) | (−) |
| | Colony Numbers | Numerous | Numerous | Numerous | Negative | Negative | Negative |
| Media after Improvement | Change in Color | (+) | (+) | (+) | (+) | (−) | (−) |
| | Colony Numbers | Numerous | Numerous | Numerous | Numerous | Negative | Negative |
| Food Stamp | | Numerous | Numerous | Numerous | Negative | Negative | Negative |
| "San-Coli" | | (−) | (−) | (−) | (−) | (−) | (−) |

TABLE 9

Kit for Salmonella

| | Rate : 10 x | −3 | −4 | −5 | −6 | −7 | −8 |
|---|---|---|---|---|---|---|---|
| Dilution | Amount of Microorganism | $10^6$ | $10^5$ | $10^4$ | $10^3$ | $10^2$ | $10^1$ |
| Media before Improvement | Change in Color | (+) | (+) | (+) | (−) | (−) | (−) |
| | Colony Numbers | Numerous | Numerous | Numerous | Negative | Negative | Negative |
| Media after Improvement | Change in Color | (+) | (+) | (+) | (+) | (+) | (−) |
| | Colony Numbers | Numerous | Numerous | Numerous | Numerous | Numerous | Negative |
| Food Stamp | | Numerous | Numerous | Numerous | Negative | Negative | Negative |
| "San-Coli" | | (−) | (−) | (−) | (−) | (−) | (−) |

TABLE 10

Kit for *Vibrio parahaemolyticus*

| | Rate : 10 × | −3 | −4 | −5 | −6 | −7 | −8 |
|---|---|---|---|---|---|---|---|
| Dilution | Amount of Microorganism | $10^6$ | $10^5$ | $10^4$ | $10^3$ | $10^2$ | $10^1$ |
| Media before Improvement | Change in Color | (+) | (+) | (−) | (−) | (−) | (−) |
| | Colony Numbers | Numerous | Negative | Negative | Negative | Negative | Negative |
| Media after Improvement | Change in Color | (+) | (+) | (+) | (+) | (+) | (−) |
| | Colony Numbers | Numerous | Numerous | Numerous | Numerous | Numerous | Negative |
| Food Stamp "San-Coli" | | Numerous (−) | Numerous (−) | Numerous (−) | Negative (−) | Negative (−) | Negative (−) |

TABLE 11

Kit for *Escherichia coli* group

| | Rate : 10 × | −3 | −4 | −5 | −6 | −7 | −8 |
|---|---|---|---|---|---|---|---|
| Dilution | Amount of Microorganism | $10^6$ | $10^5$ | $10^4$ | $10^3$ | $10^2$ | $10^1$ |
| Media before Improvement | Change in Color | (+) | (+) | (+) | (−) | (−) | (−) |
| | Colony Numbers | Numerous | Numerous | Numerous | Negative | Negative | Negative |
| Media after Improvement | Change in Color | (+) | (+) | (+) | (+) | (+) | (−) |
| | Colony Numbers | Numerous | Numerous | Numerous | Numerous | Few | Negative |
| Food Stamp "San-Coli" | | Numerous (−) | Numerous (−) | Numerous (−) | Negative (−) | Negative (−) | Negative (−) |

*Staphylococcus aureus* (MRSA), *Staphylococcus aureus* (MSSA), *Staphylococcus epidermidis*, *Staphylococcus saprophyticus*, *Staphylococcus haemolyticus*, Enterococcus sp., Bacillus sp., *Salmonella typhimurium*, *Salmonella typhi*, *Proteus vulgaris*, *Proteus mirabilis*, *Citrobacter freundii*, *Citrobacter diversus*, *Klebsiella pneumoniae*, *Klebsiella oxytoca*, *Enterobacter aerogenes*, *Enterobacter cloacae*, *Serratia marcescens*, *Hafnia alvei*, *Morganella morganii*, *Vibrio parahaemolyticus*, *Vibrio fluvialis*, *Vibrio vulnificus*, Aeromonas sp., *Plesiomonas shigelloides*, *Escherichia coli* (O-157 EHRC), *Escherichia coli* (O-55 EPEC), *Escherichia coli* (O-124 EIEC), *Escherichia coli* (O-25 ETRC), Pseudomonas sp., Acinetobacter Sp., Flavobacterium sp., etc. were used and their detection was conducted whereupon good results were obtained. Relation between the microorganisms showing positive result and the changes in color of the medium is given in Table 12. It was noted that coloration was good and the resulting color had an excellent discriminating ability.

TABLE 12

Microorganism showing Positive Reaction and Color Change

| Microorganism-Detecting Apparatus | Microorganisms showing Positive Reactions | | Before Improvement | | After Improvement | |
|---|---|---|---|---|---|---|
| | | | ※Negative | Positive | ※Negative | Positive |
| Kit for Detecting Staphylococcus | | *Staphylococcus aureus* | pink | (weak) orange (strong) yellow | red | yellow |
| | | Others | pink | yellow | red | |
| Kit for Detecting Salmonella | | Salmonella | purple | dark purple | blue | purple |
| | Others | genera Citrobacter and Enterobacter | purple | yellow | blue | purple |
| | | genera Klebsiella, Proteus and *E. coli* group | purple | yellow | blue | |
| Kit for Vibrio parahaemolyticus | | *Vibrio parahaemolyticus* | bluish purple | yellowish green | purple | yellow |
| | Others | genera Enterococcus and Serratia | bluish purple | yellow | purple | yellow |
| | | genera Klebsiella, Proteus and Citrobacter | bluish purple | yellow | purple | |
| Kit for Escherichia coli Group | | *Escherichia coli* group | purple | yellow | green | yellow |
| | | Others | purple | yellow or white (transparent) | green | |

Others: refer to the above-mentioned test microorganisms
※Negative: the same color as before the test An improved medium for *Escherichia coli* group mentioned in the above Example 11(i)(c) where Bromcresol Purple was substituted for Bromthymol Blue gave a good result in detecting the microorganisms in food and food materials. For example, a good result was obtained in the detection of a microorganism in milk products by the use of a microorganism-detecting apparatus (containing the improved medium for *Escherichia coli*) constituted according to Example 10 (particularly by referring to FIGS. 34 to 51). The coloration was good and the resulting color had an excellent discriminating ability.

Example 12

By utilizing a microorganism-detecting apparatus as shown in FIG. 35 wherein a medium suitable for measuring numbers of viable cells is used, target microorganisms are cultured. After incubation for a determined period, the cultured medium is measured for turbidity. In the experimentation, it is checked whether or not the number of viable microorganism cells prior to the incubation can be estimated from the resultant turbidity data.

(1) To a medium for measuring the number of viable cells was added a solution of microorganisms with a predetermined concentration ($10^8$ to $10^1$ cells) and the medium was incubated at 37° C. for a certain time (3, 5, and 6 hours, respectively).

| Medium for measuring the number of viable cells Composition per 1 liter of medium | |
| --- | --- |
| Meat extract | 3.0 g |
| Casein peptone | 15.0 g |
| Yeast extract | 5.0 g |
| Glucose | 1.0 g |

Figure 71:
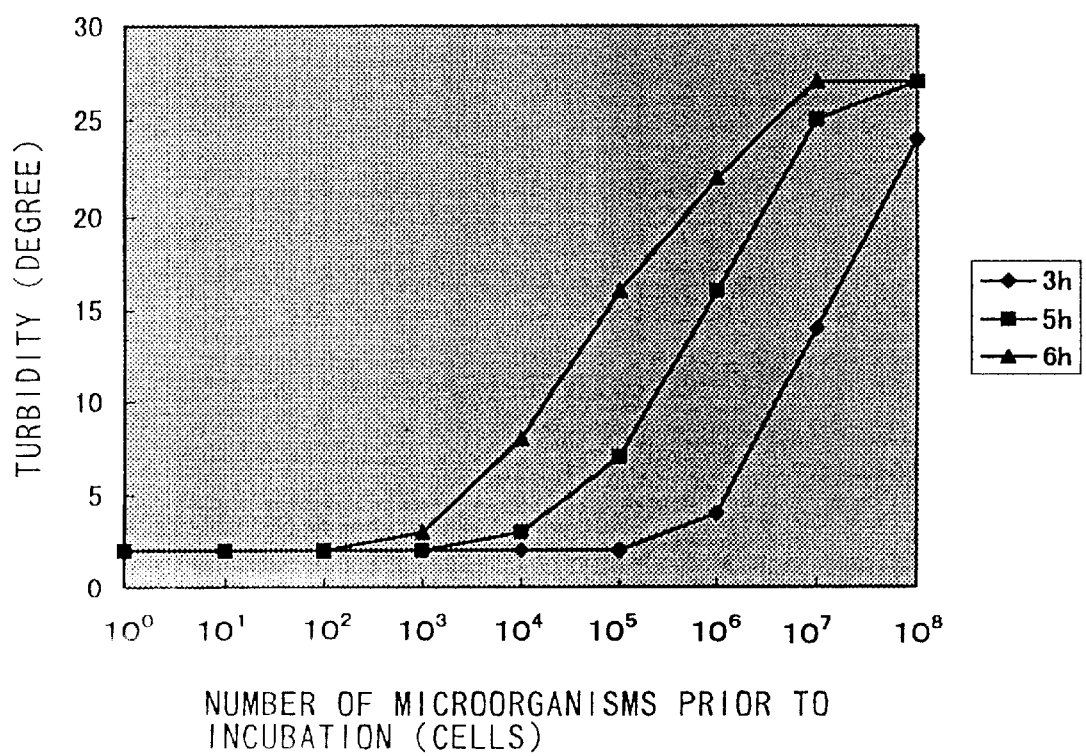
FIG. 71 is a graph showing the relationship between the number of viable *Staphylococcus aureus* cells and measured turbidity data when the microorganism was cultured in an embodiment of the microorganism-detecting apparatus according to the present invention.
Figure 72:
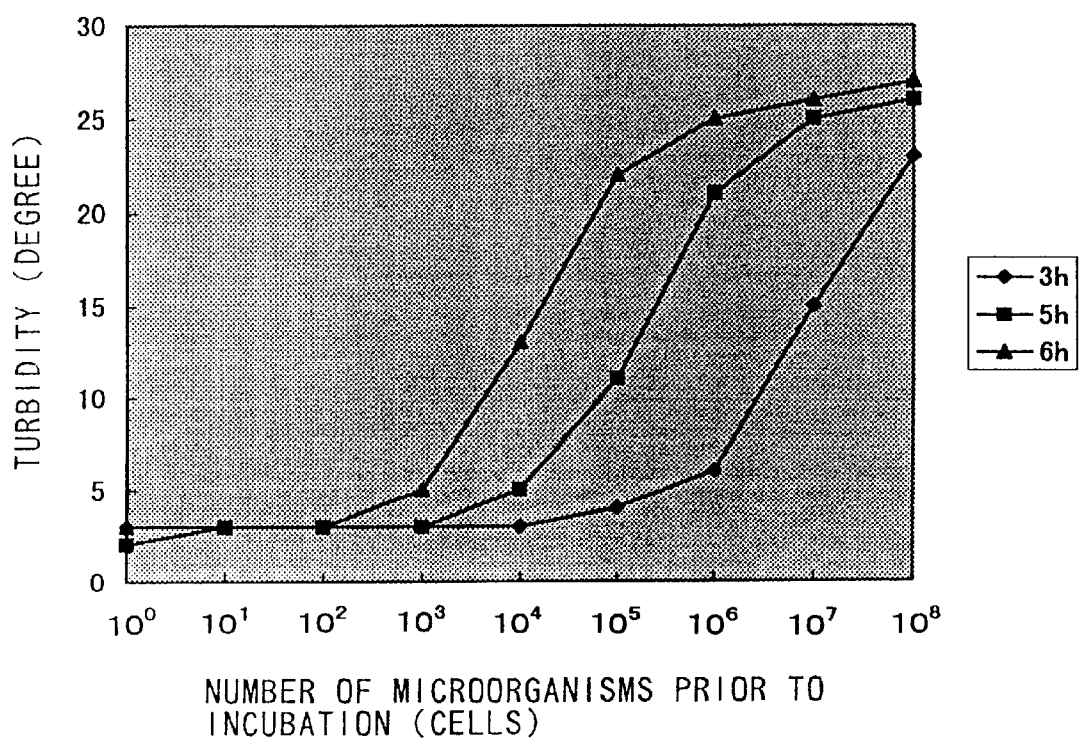
FIG. 72 is a graph showing the relationship between the number of viable *Escherichia coli* cells and measured turbidity data when the microorganism was cultured in an embodiment of the microorganism-detecting apparatus according to the present invention.

(2) The cultured medium was diluted with a physiological saline solution to a 2-fold dilution. Then, said 2-fold diluted medium was applied to a terbidimeter (such as a device designed to measure the bacterial density in a liquid medium), McFarland turbidimeter (available from bioMerieux-Vitek Japan, Ltd., Japan; ATB1550) and measured for turbidity. The results are shown in FIGS. 71 and 72. FIG. 71 is the relation between the number of viable *Staphylococcus aureus* cells and the measured turbidity data. FIG. 72 is the relation between the number of viable *Escherichia coli* cells and the measured turbidity data.

In this experimentation, the number of the viable cells ranges from $10^3$ to $10^8$ cells after incubation for 5 to 6 hours and it is confirmed that there is a proportional relationship between the number of viable cells and turbidity data. Thus, it is understood that it is possible to estimate the number of viable microorganism cells prior to incubation by utilizing the microorganism-detecting apparatus according to the present invention.

Further, when a suitable incubation time and turbidity is selected, it would enable a person to estimate the the number of viable microorganism cells prior to incubation. A concentration of medium for measuring the number of viable cells may be suitably selected in order to give a suitable turbidity value.

While the best mode for carrying out the invention has been described in detail, those familiar with the art to which this invention relates will recognize various alternative designs and embodiments for practicing the invention as defined by the following claims.

What is claimed is:

1. An apparatus for detecting a microorganism, comprising:
   a container to hold both the microorganism and a medium for culturing the microorganism during an incubation period of the microorganism;
   a microorganism-collecting part, locatable within said container, to collect the microorganism and then transfer the microorganism into said container;
   a first member to hold the medium and then release the medium such that the medium is deposited into said container and into contact with the microorganism-collecting part during the incubation period; and
   a second member to hold a disinfectant and then release the disinfectant such that the disinfectant is deposited into said container and into contact with the medium and the microorganism after the incubation period.

2. The apparatus according to claim 1, wherein said first member comprises a first vessel and said second member comprises a second vessel.

3. The apparatus according to claim 1, wherein said first member is to release the medium by applying a first external force to said first member and said second member is to release the disinfectant by applying a second external force to said second member.

4. The apparatus according to claim 1, wherein said first member is to release the medium by applying an external force to said first member.

5. The apparatus according to claim 1, wherein said container is open at one end and said microorganism-collecting part is locatable within said container by being passed through the open end of said container, and further comprising a medium for culturing the microorganism contained within said first member and a disinfectant contained within said second member.

6. The apparatus according to claim 5, and further comprising an antibiotic substance to be added to said medium during the incubation period.

7. The apparatus according to claim 6, wherein said antibiotic substance is located within said container prior to release of the medium from said first member.

8. The apparatus according to claim 7, wherein said first member is to release said medium by applying an external force to said first member.

9. The apparatus according to claim 8, wherein said second member is to release said disinfectant by applying an external force to said second member.

10. The apparatus according to claim 7, wherein said antibiotic substance is located within said container prior to release of the medium from the first member by one of being located at a discrete location within said container, being located on said microorganism-collecting member, and being coated on an inner wall of said container.

11. The apparatus according to claim 10, wherein said microorganism-collecting member comprises a rod and an end member connected to an end of said rod, and said antibiotic substance is located on said microorganism-collecting member by being located on said end member.

12. The apparatus according to claim 6, wherein said antibiotic substance is to be added to said medium during said incubation period by being mixed with said medium in said first member, such that upon release of said medium from said first member said antibiotic substance is also released from said first member.

13. The apparatus according to claim 5, wherein said medium includes a substance capable of changing colors in response to growth of the microorganism.

14. The apparatus according to claim 5, wherein said medium for culturing the microorganism is selected from the group consisting of:
  (a) a medium for culturing Salmonella having a composition substantially containing 3 to 7 grams of tryptone, 1 to 6 grams of a yeast extract, 5 to 15 grams of lysine, 0.5 to 2 grams of glucose, 7 to 9 grams of sodium chloride, 1 to 2 grams of monopotassium dihydrogen phosphate, 0.1 to 0.3 grams of sodium thiosulfate, 0.2 to 0.4 grams of ammonium iron citrate, 15 to 25 grams of magnesium chloride, 27 to 33 milliliters of a 0.4% Malachite Green solution, and 0.01 to 0.03 grams of Bromcresol Purple per 1,000 milliliters of the medium, with the pH of the medium being about 5.3 to 5.7;
  (b) a medium for culturing *Vibrio parahaemolyticus* having a composition substantially containing 15 to 25 grams of mannitol, 5 to 10 grams of sodium citrate, 0.1 to 0.3 grams of sodium thiosulfate, 0.01 to 0.03 grams of Bromocresol Purple per 1,000 milliliters of the medium, and 25 to 40 grams of a salt polymyxin broth containing a yeast extract, peptone, sodium chloride and polymyxin B, with the pH of the medium being about 7.0 to 7.4;
  (c) a medium for culturing *Escherichia coli* group having a composition substantially containing 3 to 8 grams of lactose, 0.03 to 0.05 grams of Bromthymol Blue or Bromocresol Purple per 1,000 milliliters of the medium, and 26 to 43 grams of a lauryl sulfate broth containing tryptose, lactose, monopotassium dihydrogen phosphate, dipotassium monohydrogen phosphate, sodium chloride and sodium lauryl sulfate, with the pH of the medium being about 6.75 to 7.25; and
  (d) a medium for culturing Staphylococcus having a composition substantially containing 5 to 15 grams of tryptone, 2 to 8 grams of a yeast extract, 5 to 15 grams of mannitol, 2 to 8 grams of dipotassium monohydrogen phosphate, 5 to 6 grams of lithium chloride, 12 to 20 grams of glycine, 10 to 14 grams of sodium pyruvate, 12 to 18 milliliters of a 1% aqueous solution of potassium tellurite, and 0.02 to 0.03 grams of Phenol Red per 1,000 milliliters of the medium, with the pH of the medium being about 7.25 to 7.75.

15. The apparatus according to claim 5, wherein said first member and said second member are spaced from each other, and further comprising a cover for housing said first member and said second member, wherein said housing is attachable to said container, and wherein said first member is to release said medium by applying a first external force to said first member and said second member is to release said disinfectant by applying a second external force to said second member.

16. The apparatus according to claim 1, and further comprising a cover attachable to said container, wherein said first member comprises first a vessel contained within said cover.

17. The apparatus according to claim 16, and further comprising a perforated plate located between said first vessel and said container when said cover is attached to said container.

18. The apparatus according to claim 17, and further comprising a guide member located between said perforated plate and said container when said cover is attached to said container, wherein said guide member is to guide the medium released from said first vessel into said container.

19. The apparatus according to claim 1, wherein said apparatus is to detect a microorganism selected from the group consisting of enteropathogenic *Escherichia coli*, *Staphylococcus aureus*, *Vibrio parahaemolyticus* and Salmonella.

20. The apparatus according to claim 1, and further comprising a cover attachable to said container, wherein said second member is contained within said cover such that the disinfectant is released from said second member when said cover is attached to said container.

21. The apparatus according to claim 20, wherein said container is transparent.

22. The apparatus according to claim 1, wherein said first member comprises a first vessel, and further comprising a cover attachable to said container, with said first vessel located within said cover.

23. The apparatus according to claim 1, wherein said second member comprises a second vessel, and further comprising a cover attachable to said container, with said second vessel located within said cover.

24. The apparatus according to claim 1, wherein said first member comprises a first vessel and said second member comprises a second vessel, and further comprising a cover to support and house said first vessel and said second vessel.

25. The apparatus according to claim 24, wherein said cover comprises a first portion and a second portion, with said first vessel located within said first portion and said second vessel located within said second portion.

26. The apparatus according to claim 1, and further comprising a first cover portion housing said first member and a second cover portion housing said second member, with said first cover portion and said second cover portion being slidable relative to one another, and further comprising structure on said first cover portion and said second cover portion to prevent unwanted sliding of said first cover portion relative to said second cover portion.

27. The apparatus according to claim 26, wherein said structure comprises at least one projection carried by one of said first cover portion and said second cover portion and at least one slot in the other of said first cover portion and said second cover portion, with said at least one projection being receivable within said at least one slot.

28. The apparatus according to claim 26, and further comprising a cap member slidably attached to said second cover portion and structure on said cover member and said second cover portion to prevent unwanted sliding of said second cover portion relative to said cap member.

29. The apparatus according to claim 28, wherein said structure comprises at least one projection carried by one of said second cover portion and said cap member and at least one slot in the other of said second cover portion and said cap member, with said at least one projection being receivable within said at least one slot.

30. An apparatus for detecting a microorganism, comprising:
  a first member having a first perforated partition to receive and hold a first vessel containing a disinfectant;
  a second member having a second perforated partition to receive and hold a second vessel containing a medium, with said second member being attachable to a container and said first member being slidably attachable to said second member; and
  a cap member movably attached to a first end of said first member;
  such that the second vessel is broken by sliding said first member relative to said second member whereby the medium is released from said second vessel and deposited into the container during an incubation period, and the first vessel is broken by moving said cap member relative to said first member whereby the disinfectant is released from said first vessel and deposited into the container after the incubation period.

31. The apparatus according to claim 30, and further comprising a second vessel containing a medium for culturing the microorganism, wherein said medium is selected from the group consisting of:
   (a) a medium for culturing Salmonella having a composition substantially containing 3 to 7 grams of tryptone, 1 to 6 grams of a yeast extract, 5 to 15 grams of lysine, 0.5 to 2 grams of glucose, 7 to 9 grams of sodium chloride, 1 to 2 grams of monopotassium dihydrogen phosphate, 0.1 to 0.3 grams of sodium thiosulfate, 0.2 to 0.4 grams of ammonium iron citrate, 15 to 25 grams of magnesium chloride, 27 to 33 milliliters of a 0.4% Malachite Green solution, and 0.01 to 0.03 grams of Bromcresol Purple per 1,000 milliliters of the medium, with the pH of the medium being about 5.3 to 5.7;
   (b) a medium for culturing *Vibrio parahaemolyticus* having a composition substantially containing 15 to 25 grams of mannitol, 5 to 10 grams of sodium citrate, 0.1 to 0.3 grams of sodium thiosulfate, 0.01 to 0.03 grams of Bromocresol Purple per 1,000 milliliters of the medium, and 25 to 40 grams of a salt polymyxin broth containing a yeast extract, peptone, sodium chloride and polymyxin B, with the pH of the medium being about 7.0 to 7.4;
   (c) a medium for culturing *Escherichia coli* group having a composition substantially containing 3 to 8 grams of lactose, 0.03 to 0.05 grams of Bromthymol Blue or Bromocresol Purple per 1,000 milliliters of the medium, and 26 to 43 grams of a lauryl sulfate broth containing tryptose, lactose, monopotassium dihydrogen phosphate, dipotassium monohydrogen phosphate, sodium chloride and sodium lauryl sulfate, with the pH of the medium being about 6.75 to 7.25; and
   (d) a medium for culturing Staphylococcus having a composition substantially containing 5 to 15 grams of tryptone, 2 to 8 grams of a yeast extract, 5 to 15 grams of mannitol, 2 to 8 grams of dipotassium monohydrogen phosphate, 5 to 6 grams of lithium chloride, 12 to 20 grams of glycine, 10 to 14 grams of sodium pyruvate, 12 to 18 milliliters of a 1% aqueous solution of potassium tellurite, and 0.02 to 0.03 grams of Phenol Red per 1,000 milliliters of the medium, with the pH of the medium being about 7.25 to 7.75.58.

32. The apparatus according to claim 30, wherein said cap member is movably attached to said end of said first member by being rotatably attached to said end of said first member, and the first vessel is broken by rotating said cap member relative to said first member.

33. The apparatus according to claim 30, wherein said cap member is movably attached to said end of said first member by being slidably attached to said end of said first member, and the first vessel is broken by sliding said cap member relative to said first member, and further comprising structure on said first member and said cap member to prevent sliding of said cap member relative to said first member until after the second vessel has been broken by sliding said first member relative to said second member.

34. The apparatus according to claim 33, wherein said structure comprises at least one projection carried by one of said first member and said cap member and at least one slot in the other of said first member and said cap member, with said at least one projection being receivable within said at least one slot.

35. The apparatus according to claim 30, and further comprising structure on said first member and said second member to prevent unwanted sliding of said first member relative to said second member.

36. The apparatus according to claim 35, wherein said structure comprises at least one projection carried by one of said first member and said second member and at least one slot in the other of said first member and said second member, with said at least one projection being receivable within said at least one slot.

37. A method for quantitatively measuring the amount of viable microorganism cells in a sample, comprising:
   inserting a sample collected with a microorganism collecting part into a container;
   associating with said container a first member containing a culturing medium, and a second member containing a disinfectant;
   releasing said culturing medium from said first member onto said sample during an incubation period; and
   releasing said disinfectant from said second member onto said sample after said incubation period.

38. The method according to claim 37, wherein the inserting includes inserting the microorganism collecting part along with said sample into said container, the associating includes attaching to an open end of said container a cover containing said first member and said second member, the releasing of said culturing medium includes applying a first external force to said first member, and the releasing of said disinfectant includes applying a second external force to said second member.

39. The method according to claim 38, wherein said first member is a first vessel and said second member is a second vessel, and wherein the applying of the first external force breaks said first vessel and the applying of the second external force breaks said second vessel.

40. The method according to claim 37, and further comprising adding an antibiotic substance to said sample during said incubation period.

41. The method according to claim 37, wherein the viable microorganism cells to be quantitatively measured are of a microorganism selected from the group consisting of enteropathogenic *Escherichia coli, Staphylococcus aureus, Vibrio parahaemolyticus* and Salmonella.

42. The method according to claim 41, wherein said culturing medium is selected from the group consisting of:
   (a) a medium for culturing Salmonella having a composition substantially containing 3 to 7 grams of tryptone, 1 to 6 grams of a yeast extract, 5 to 15 grams of lysine, 0.5 to 2 grams of glucose, 7 to 9 grams of sodium chloride, 1 to 2 grams of monopotassium dihydrogen phosphate, 0.1 to 0.3 grams of sodium thiosulfate, 0.2 to 0.4 grams of ammonium iron citrate, 15 to 25 grams of magnesium chloride, 27 to 33 milliliters of a 0.4% Malachite Green solution, and 0.01 to 0.03 grams of Bromcresol Purple per 1,000 milliliters of the medium, with the pH of the medium being about 5.3 to 5.7;
   (b) a medium for culturing *Vibrio parahaemolyticus* having a composition substantially containing 15 to 25 grams of mannitol, 5 to 10 grams of sodium citrate, 0.1 to 0.3 grams of sodium thiosulfate, 0.01 to 0.03 grams of Bromocresol Purple per 1,000 milliliters of the medium, and 25 to 40 grams of a salt polymyxin broth containing a yeast extract, peptone, sodium chloride and polymyxin B, with the pH of the medium being about 7.0 to 7.4;
   (c) a medium for culturing *Escherichia coli* group having a composition substantially containing 3 to 8 grams of lactose, 0.03 to 0.05 grams of Bromthymol Blue or Bromocresol Purple per 1,000 milliliters of the medium, and 26 to 43 grams of a lauryl sulfate broth containing tryptose, lactose, monopotassium dihydrogen phosphate, dipotassium monohydrogen phosphate, sodium chloride and sodium lauryl sulfate, with the pH of the medium being about 6.75 to 7.25; and (d) a medium for culturing Staphylococcus having a composition substantially containing 5 to 15 grams of tryptone, 2 to 8 grams of a yeast extract, 5 to 15 grams of mannitol, 2 to 8 grams of dipotassium monohydrogen phosphate, 5 to 6 grams of lithium chloride, 12 to 20 grams of glycine, 10 to 14 grams of sodium pyruvate, 12 to 18 milliliters of a 1% aqueous solution of potassium tellurite, and 0.02 to 0.03 grams of Phenol Red per 1,000 milliliters of the medium, with the pH of the medium being about 7.25 to 7.75.

43. A method for quantitatively measuring the amount of viable microorganism cells in a sample, comprising:

inserting a sample into a container;

depositing a culturing medium onto said sample during an incubation period by breaking a first vessel containing said culturing medium, wherein said first vessel is contained within a first member attached to an open end of said container with a first perforated member positioned between said first vessel and said sample, such that when said first vessel is broken said culturing medium flows through said first perforated member and into contact with said sample while the broken first vessel is prevented by said first perforated member from being deposited onto said sample; and after said incubation period, depositing a disinfectant onto said sample by breaking a second vessel containing said disinfectant, wherein said second vessel is contained within a second member attached to said first member with a second perforated member positioned between said second vessel and said sample, such that when said second vessel is broken said disinfectant flows through said second perforated member and into contact with said sample while the broken second vessel is prevented by said second perforated member from being deposited onto said sample.

44. The method according to claim 43, wherein said second member is slidably attached to said first member and a cap member is movably attached to said second member, such that the breaking of said first vessel results from sliding said second member relative to said first member and the breaking of said second vessel results from moving said cap member relative to said second member.

45. The method according to claim 44, wherein the moving of said cap member includes rotating said cap member relative to said second member.

46. The method according to claim 44, wherein the moving of said cap member includes sliding said cap member relative to said second member.

47. The method according to claim 43, and further comprising adding an antibiotic substance to said sample during said incubation period.

48. The method according to claim 43, wherein the viable microorganism cells to be quantitatively measured are of a microorganism selected from the group consisting of enteropathogenic *Escherichia coli, Staphylococcus aureus, Vibrio parahaemolyticus* and Salmonella.

49. The method according to claim 48, wherein said culturing medium is selected from the group consisting of:

(a) a medium for culturing Salmonella having a composition substantially containing 3 to 7 grams of tryptone, 1 to 6 grams of a yeast extract, 5 to 15 grams of lysine, 0.5 to 2 grams of glucose, 7 to 9 grams of sodium chloride, 1 to 2 grams of monopotassium dihydrogen phosphate, 0. 1 to 0.3 grams of sodium thiosulfate, 0.2 to 0.4 grams of ammonium iron citrate, 15 to 25 grams of magnesium chloride, 27 to 33 milliliters of a 0.4% Malachite Green solution, and 0.01 to 0.03 grams of Bromcresol Purple per 1,000 milliliters of the medium, with the pH of the medium being about 5.3 to 5.7;

(b) a medium for culturing *Vibrio parahaemolyticus* having a composition substantially containing 15 to 25 grams of mannitol, 5 to 10 grams of sodium citrate, 0.1 to 0.3 grams of sodium thiosulfate, 0.01 to 0.03 grams of Bromocresol Purple per 1,000 milliliters of the medium, and 25 to 40 grams of a salt polymyxin broth containing a yeast extract, peptone, sodium chloride and polymyxin B, with the pH of the medium being about 7.0 to 7.4;

(c) a medium for culturing *Escherichia coli* group having a composition substantially containing 3 to 8 grams of lactose, 0.03 to 0.05 grams of Bromthymol Blue or Bromocresol Purple per 1,000 milliliters of the medium, and 26 to 43 grams of a lauryl sulfate broth containing tryptose, lactose, monopotassium dihydrogen phosphate, dipotassium monohydrogen phosphate, sodium chloride and sodium lauryl sulfate, with the pH of the medium being about 6.75 to 7.25; and (d) a medium for culturing Staphylococcus having a composition substantially containing 5 to 15 grams of tryptone, 2 to 8 grams of a yeast extract, 5 to 15 grams of mannitol, 2 to 8 grams of dipotassium monohydrogen phosphate, 5 to 6 grams of lithium chloride, 12 to 20 grams of glycine, 10 to 14 grams of sodium pyruvate, 12 to 18 milliliters of a 1% aqueous solution of potassium tellurite, and 0.02 to 0.03 grams of Phenol Red per 1,000 milliliters of the medium, with the pH of the medium being about 7.25 to 7.75.

* * * * *